(12) United States Patent
Caldarelli et al.

(10) Patent No.: US 9,333,205 B2
(45) Date of Patent: *May 10, 2016

(54) ISOXAZOLO-QUINAZOLINES AS MODULATORS OF PROTEIN KINASE ACTIVITY

(75) Inventors: Marina Caldarelli, Milan (IT); Italo Beria, Nerviano (IT); Nicoletta Colombo, Bergamo (IT); Claudia Piutti, Nerviano (IT); Matteo Salsa, Bellinzago Novarese (IT); Gabriella Traquandi, Milan (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/813,200
(22) PCT Filed: Jul. 20, 2011
(86) PCT No.: PCT/EP2011/062453
§ 371 (c)(1),
(2), (4) Date: Jan. 30, 2013
(87) PCT Pub. No.: WO2012/013557
PCT Pub. Date: Feb. 2, 2012

(65) Prior Publication Data
US 2013/0143896 A1    Jun. 6, 2013

(30) Foreign Application Priority Data
Jul. 30, 2010   (EP) .................................... 10171375

(51) Int. Cl.
| | | |
|---|---|---|
| *C07D 498/04* | (2006.01) | |
| *A61K 31/519* | (2006.01) | |
| *C07D 498/02* | (2006.01) | |
| *A61K 45/06* | (2006.01) | |
| *A61N 5/10* | (2006.01) | |

(52) U.S. Cl.
CPC .............. *A61K 31/519* (2013.01); *A61K 45/06* (2013.01); *A61N 5/10* (2013.01); *C07D 498/02* (2013.01); *C07D 498/04* (2013.01)

(58) Field of Classification Search
None
See application file for complete search history.

(56) References Cited

FOREIGN PATENT DOCUMENTS

| WO | WO 03/070706 A1 | 8/2003 |
|---|---|---|
| WO | WO 2004/104007 A1 | 12/2004 |
| WO | WO 2005/037843 A1 | 4/2005 |
| WO | WO 2008/074788 A1 | 6/2008 |
| WO | WO 2009/156315 A1 | 12/2009 |

OTHER PUBLICATIONS

Atkins et al. Cancer Research, pp. 1-13 (author manuscript) published online on Jan. 18, 2013).*
Bursavich et al. Bioorganic & Medicinal Chemistry Letters vol. 23, pp. 6829-6833 (2013).*
Voskoglou-Nomikos et al.Clinical Cancer Research, vol. 9, pp. 4227-4239 (2003).*
Talmadge et al.The American Journal of Pathology, vol. 170, pp. 793-804 (2007).*
Cancer Drug Design and Discovery, Neidle,Stephen,ed. (Elsevier/Academic Press), pp. 427-431 (2008).*
Cohen P., "The Development and Therapeutic Potential of Protein Kinase Inhibitors", Current Opinion in Chemical Biology 3:459-465 (1999).
Velculescu V.E., "Defining the Blueprint of the Cancer Genome", Carcinogenesis 29(6):1087-1091 (2008).
Musacchio A. et al., "The Spindle-Assembly Checkpoint in Space and Time", Nature Reviews—Molecular Cell Biology 8 (5):379-393 (May 2007).
Stucke V.M. et al., "Human Mps1 Kinase is Required for the Spindle Assembly Checkpoint but Not for Centrosome Duplication", The EMBO Journal 21(7):1723-1732 (2002).
Winey M. et al., "MPS1 and MPS2: Novel Yeast Genes Defining Distinct Steps of Spindle Pole Body Duplication", The Journal of Cell Biology 114(4):745-754 (Aug. 1991).
Jones M.H. et al., "Chemical Genetics Reveals a Role for Mps1 Kinase in Kinetochore Attachment During Mitosis", Current Biology 15:160-165 (Jan. 26, 2005).
Weiss E et al., "The *Saccharomyces cerevisiae* Spindle Pole Body Duplication Gene MPS1 is Part of a Mitotic Checkpoint", The Journal of Cell Biology 132(1&2):111-123 (Jan. 1996).
Jelluma N. et al., "Mps1 Phosphorylates Borealin to Control Aurora B Activity and Chromosome Alignment", Cell 132:233-246 (Jan. 25, 2008).
Tighe A. et al., "Mps1 Kinase Activity Restrains Anaphase During an Unperturbed Mitosis and Targets Mad2 to Kinetochores", J. Cell Biol. 181(6):893-901 (2008).
Jelluma N. et al., "Chromosomal Instability by Inefficient Mps1 Auto-Activation Due to a Weakened Mitotic Checkpoint and Lagging Chromosomes", PloS One 3(6):e2415 (Jun. 2008).

(Continued)

*Primary Examiner* — Emily Bernhardt
(74) *Attorney, Agent, or Firm* — Scully, Scott, Murphy & Presser, P.C.

(57) ABSTRACT

The present invention relates to substituted isoxazoloquinazolines which modulate the activity of protein kinases and are therefore useful in treating diseases caused by dysregulated protein kinase activity, in particular human MPS1 and PERK. The present invention also provides methods for preparing these compounds, pharmaceutical compositions comprising these compounds, and methods of treating diseases utilizing such these compounds or the pharmaceutical compositions containing them.

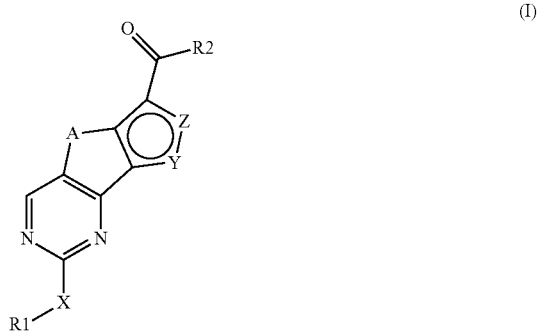

7 Claims, No Drawings

(56) References Cited

OTHER PUBLICATIONS

Schmidt M. et al., "Ablation of the Spindle Assembly Checkpoint by a Compound Targeting Mps1", EMBO reports 6 (9):866-872 (2005).
Ma Y. et al., "Expression of Targeting Protein for Xklp2 Associated with Both Malignant Transformation of Respiratory Epithelium and Progression of Squamous Cell Lung Cancer", Clin Cancer Research 12(4):1121-1127 (Feb. 15, 2006).
Bertheau P. et al., "Exquisite Sensitivity of TP53 Mutant and Basal Breast Cancers to a Dose-Dense Epirubicin-Cyclophosphamide Regimen", PloS Medicine 4(3):e90—(Mar. 2007).
de Cárcer G. et al., "Targeting Cell Cycle Kinases for Cancer Therapy", Current Medicinal Chemistry 14(9):969-985 (2007).
Kops G.J.P.L. et al., "On the Road to Cancer: Aneuploidy and the Mitotic Checkpoint", Nature Reviews Cancer 5:773-785 (Oct. 2005).
Weaver B.A.A. et al., "Aneuploidy Acts Both Oncogenically and as a Tumor Suppressor", Cancer Cell 11(1):25-36 (Jan. 2007).
Harding H.P. et al., "Protein Translation and Folding are Coupled by an Endoplasmic-Reticulum-Resident Kinase", Nature 397:271-274 (Mar. 4, 1999).
Bi M. et al., "ER Stress-Regulated Translation Increases Tolerance to Extreme Hypoxia and Promotes Tumor Growth", The EMBO Journal 24(19):3470-3481 (2005).
Studier F.W., "Protein Production by Auto-Induction in High-Density Shaking Cultures", Protein Expression and Purification 41:207-234 (2005).

Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).
Beria I. et al., "Identification of 4,5-Dihydro-1H-Pyrazolo[4,3-h]Quinazoline Derivatives as a New Class of Orally and Selective Polo-Like Kinase 1 Inhibitors", Journal of Medicinal Chemistry 53(9):3532-3551 (May 13, 2010).
Traquandi G. et al., "Identification of Potent Pyrazole[4,3-h]Quinazoline-3-Carboxamides as Multi-Cyclin-Dependent Kinase Inhibitors", Journal of Medicinal Chemistry 53(5):2171-2187 (Mar. 11, 2010).
Brasca M.G. et al., "Identification of N,1,4,4-Tetramethyl-8-{[4-(4-Methylpiperazin-1-yl)Phenyl]Amino}-4,5-Dihydro-1H-Pyrazolo[4,3-h]Quinazoline-3-Carboxamide (PHA-848125), a Potent, Orally Available Cyclin Dependent Kinase Inhibitor", Journal of Medicinal Chemistry 52(16):5152-5163 (Jul. 15, 2009).
Angiolini M. et al., "Structure-Based Optimization of Potent PDK1 Inhibitors", Bioorganic & Medicinal Chemistry Letters 20(14):4095-4099 (Jul. 15, 2010).
International Search Report dated Nov. 24, 2011, issued in corresponding International Application No. PCT/EP2011/062453.

\* cited by examiner

SEQUENCE LISTING

<160> NUMBER OF SEQ ID NOS: 2

<210> SEQ ID NO 1
<211> LENGTH: 77
<212> TYPE: DNA
<213> ORGANISM: Artificial
<220> FEATURE:
<223> OTHER INFORMATION: Forward oligonucleotide primer

<400> SEQUENCE: 1
ggggacaagt ttgtacaaaa aagcaggctt actggaagtt ctgttccagg ggccccgcag    60
gcttttccat cctcatc    77

```
<210> SEQ ID NO 2
<211> LENGTH: 55
<212> TYPE: DNA
<213> ORGANISM: Artificial
<220> FEATURE:
<223> OTHER INFORMATION: Reverse oligonucleotide primer

<400> SEQUENCE: 2
ggggaccact tgtacaaga aagctgggtt ttaattgctt ggcaaagggc tatgg          55
```

ISOXAZOLO-QUINAZOLINES AS MODULATORS OF PROTEIN KINASE ACTIVITY

The present invention relates to certain substituted isoxazolo-quinazoline compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neuro-degenerative disorders.

For a general reference to PKs malfunctioning or deregulation see, for instance, Current Opinion in Chemical Biology 1999, 3, 459-465 and Carcinogenesis 2008, 29, 1087-1091.

The use of mitotic inhibitors in cancer therapy is a widely accepted clinical strategy for the treatment of a broad range of human cancers. Taxanes (Paclitaxel and Docetaxel) and Vinca Alkaloids (Vincristine and Vinblastine) work by either stabilizing or destabilizing microtubules with catastrophic consequences in cells progressing through mitosis. They are first line therapeutics for several tumour types and second line in cisplatin-refractory ovarian, breast, lung, bladder and esophagus cancers (Taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types.

Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle.

The Spindle Assembly Checkpoint (SAC) is specifically required for proper chromosomal segregation into the two daughter cells upon cellular division. It ensures that sister chromatids aligned at the metaphase plate do not separate prior to the bipolar attachment of all duplicated chromosomes to the mitotic spindle (Reviewed in Musacchio A. and Salmon D. Nat Rev Mol Cell Biol, May; 8(5): 379-93, 2007).

Even a single un-aligned chromosome is sufficient to trigger the SAC signal, it is a tightly regulated pathway that ultimately results into the inhibition of the anaphase promoting complex/cyclosome (APC/C)-mediated polyubiquitylation and degradation of two key mitotic components: cyclin B1 and Securin. Securin specifically is required to get sister chromatids separation and anaphase transition, instead cyclin B1 inactivates the master mitotic kinase CDK1 promoting mitotic exit. (Reviewed in Musacchio A. and Salmon D. Nat Rev Mol Cell Biol, May; 8(5): 379-93, 2007).

A large group of proteins has been already identified to play a role in SAC functions: human MPS1 (monopolar spindle 1) kinase, (also known as TTK) has certainly a major role. MPS1 is a dual Tyrosine and Serine/Threonine kinase highly conserved from yeast to mammals. The human genome encodes for just one MPS1 gene family member, which does not have high sequence similarities with other protein kinases.

MPS1 is a cell cycle regulate enzyme that is upregulated and activated in mitosis upon phosphorylation (Stucke V M, et al., Embo J. 21 (7): 1723, 002).

In *Saccharomyces cerevisiae*, MPS1 controls spindle-pole body duplication (Winey M. et al., J. Cell Biol 114:745, 1991), spindle assembly (Jones, M. H. et al., Curr. Biol. 15: 160, 2005) and the spindle assembly checkpoint (Weiss and Winey, J. Cell. Biol 132:111, 1996). Instead in higher eukaryotes the MPS1 kinase activity is mainly involved in SAC regulation and functions (Jelluma, N. et al., Cell 132: 233, 2008).

RNA interference experiments indicate that in the absence of MPS1 the SAC functions are compromised: mitotic length is reduced and cells divide rapidly without methaphase plate alignment, which ultimately causes aberrant aneuploidization, mitotic catastrophe and is not anymore compatible with cellular survival (Jelluma N. et al., Cell 132: 233, 2008; Tighe A. et al., J Cell Biol 2008; Jelluma N. et al., Plos ONE 3 (6): e2415, 2008). Moreover, to support these results, a small molecule ATP-competitor MPS1 inhibitor was described and despite its not clean selectivity profile, it was shown to be capable to inactivate SAC functions, inactivate nocodazole and taxol mediated mitotic arrest and promote cell death mainly in tumorigenic cell lines (Schmidt et al., EMBO Rep, 6(9): 866, 2005).

Despite that most of the tumors are aneuploid, MPS1 was never found to be mutated in cancer, instead, it has been found upregulated in a number of tumors of different origins like bladder, anaplastic thyroid, breast and prostate cancer (Yuan B. et al, Clin Cancer Res, 12(4): 1121, 2006). Moreover was found in the signature of the top 25 genes over-expressed in CIN and aneuploid tumors which predict clinical outcome in breast and lung cancer, medulloblastoma, glioma, mesothelioma and lymphoma (Carter S L et al., Nat. Genet. 38 (9): 1043, 2006). Finally is highly elevated in metastatic tumors and was found to be over-expressed in p53 mutated breast cancers (Bertheau P. et al., Plos Med 4(3):e90, 2007).

Together with the fact that also other SAC components like MAD2, BUBR1 or BUB1 have been found upregulated in different tumors (deCarcer G. et al., Curr Med Chem 14(9): 969, 2007), it looks that SAC functions could be required and essential to keep tumoral highly aneuploidy cells capable to segregate and tumoral selectivity of SAC inhibitors is foreseen in particular for highly aneuploid tumors like colon, lung and breast carcinomas (Kops G. J. et al., Nat. Rev Cancer, 5:773, 2005).

Finally, massive aneuploidy induction and SAC deregulation have been shown to reduce tumorigenesis in tumour prone mice sustaining the hypothesis that SAC inhibition could confer tumour growth inhibition (Weaver et al., Cancer Cell 11(1): 25, 2007). Thus, for these reasons, pharmacological attenuation of MPS1 function may have a therapeutic benefit in the treatment of several diverse cancers.

Endoplasmic reticulum (ER) homeostasis is essential for normal cell functions including lipids and steroids synthesis, carbohydrates and steroids metabolism, calcium concentration regulation, drug detoxification, secreted protein folding, disulfide bond formation and glycosylation. Many different conditions can disrupt ER homeostasis such as hypoxia, glucose deprivation and mutant protein expression. Perturbation of ER homeostasis impairs protein folding causing accumulation of unfolded proteins inside the ER and activates a survival pathway named Unfolded Protein Response (UPR). UPR activation reduces protein loading in the ER blocking protein synthesis and increasing endoplasmic reticulum associated degradation (ERAD). In addition it induces the synthesis of a series of transcription factors devoted to antioxidant response and ER protein synthesis to re-establish ER homeostasis. It has been reported that UPR is activated in a range of breast cancer cell lines and tumor models (Chen X et al, 2002; Gazit G, et al, 1999; Shen J et al, 1987; Ozawa K, et al, 2001) and may contribute to tumor growth and survival protecting transformed cells from inadequate tumor environment (e.g. Hypoxia, presence of larger amount of unfolded proteins). UPR is regulated by three different effectors; the kinase-ribonuclease IRE 1, the protein kinase PERK (eIF2αK3) and the transcription factor ATF6.

Pancreatic endoplasmic reticulum kinase (PERK eIF2αK3) signaling has been shown to play important role to attenuate cellular protein synthesis during the unfolded protein response via phosphorylation of the α-subunit of the translation initiator factor eIF2 at Ser51 (Ron D. Nature 1999, 397, 271-2749). Phosphorylated eIF2α contribute to pause general protein synthesis and promotes the translation of some selected genes like ATF4, a transcription factor that regulates the expression of genes involved in the amino acid metabolism, in the antioxidant response and promoting the expression of the transcription factor, DNA Damage-inducible Protein, GADD153 (CHOP). ATF4 is overexpressed in human solid tumors and its depletion in cell lines clearly reduces tumor growthours.

Different members of eIF2αK family are able to phosphorylate eIF2α at Serine 51 blocking protein synthesis in response to different stressing conditions. In fact HRI (eIF2αK1) is activated by heme deficiency, PKR (eIF2αK2) is activated after viral infection, GCN2 (eIF2αK4) is activated during aminoacid deprivation while PERK (eIF2αK3) instead responds to ER stress Recent studies reported that depletion or kinase dead expression of PERK or mutation in the phosphorylated site of eIF2α impairs cell survival under extreme hypoxia. In addition, tumors derived from PERK (−/−) MEFcells transfected with KRas are smaller and exhibit higher levels of apoptosis in hypoxic area compared to tumors derived from PERK (+/+) MEF (Koumenis C. The EMBO Journal, 2005, 24, 3470-3481). These finding suggest that this pathway is an attractive target for antitumor modalities.

Tricyclic quinazoline derivatives known in the art as protein kinase inhibitors are disclosed in WO05/037843. Pyrazolo-quinazoline derivatives known in the art as protein kinase inhibitors are disclosed in WO04/104007, in the name of Pharmacia Italia S.P.A.

Despite these developments, there is still need for effective agents for said diseases.

The present inventors have now discovered that compounds of the formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a substituted isoxazolo-quinazoline compound of the formula (I)

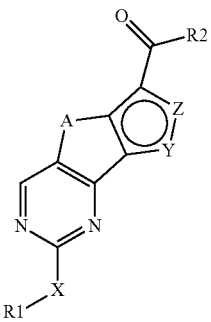

wherein:
Y is O and Z is N, or Y is N and Z is O;
X is O, S, $SO_2$ or NH;
R1 is hydrogen or an optionally substituted group selected from straight or branched $C_1$-$C_6$ alkyl, $C_3$-$C_7$ cycloalkyl, heterocyclyl and aryl;
R2 is —NR'R" or —OR', wherein R' and R" are, each independently, hydrogen or an optionally substituted group selected from straight or branched $C_1$-$C_6$ alkyl, $C_3$-$C_7$ cycloalkyl, cycloalkyl-alkyl, heterocyclyl, heterocyclylalkyl, aryl and arylalkyl, or, together with the nitrogen atom to which they are bonded, R' and R" may form an optionally substituted 5 to 6 membered heteroaryl or heterocyclyl group, optionally containing one additional heteroatom selected from N, O and S;
A is a divalent group selected from —$(CH_2)_2$—, —$CH_2$—$C(CH_3)_2$—, —$C(CH_3)_2$—$CH_2$— and —CH=CH—; and the pharmaceutically acceptable salts thereof.

The present invention also provides methods of synthesizing the substituted isoxazolo-quinazoline compounds, represented by the formula (I), prepared through a process consisting of standard synthetic transformations and isomers, tautomers, hydrates, solvates, complexes, metabolites, prodrugs, carriers, N-oxides.

The present invention also provides a method for treating diseases caused by and/or associated with dysregulated protein kinase activity, particularly human MPS1 (TTK), PLK family members, protein kinase C in different isoforms, Met, PAK-4, PAK-5, PERK, PIM-1, PIM-2, PIM-3, STLK-2, DDR-2, Aurora 1, Aurora 2, Bub-1, Chk1, Chk2, HER2, raft, MEK1, MAPK, EGF-R, PDGF-R, FGF-R, IGF-R, PI3K, weel kinase, Src, Abl, Akt, MAPK, ILK, MK-2, IKK-2, Cdc7, Nek, Cdk/cyclin kinase family, more particularly human MPS1 and PERK, which comprises administering to a mammal, in need thereof, an effective amount of a substituted pyrazolo-quinazoline compound represented by the formula (I) as defined above.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non- Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma and mesothelioma, highly aneuploid tumors and tumors which do overexpress mitotic checkpoint.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

In addition, the method of the present invention also provides tumor angiogenesis and metastasis inhibition as well as the treatment of organ transplant rejection and host versus graft disease.

The present invention also provides a pharmaceutical composition comprising one or more compounds of the formula (I) or a pharmaceutically acceptable salt thereof and a pharmaceutically acceptable excipient, carrier or diluent.

The present invention further provides a pharmaceutical composition comprising a compound of the formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

The present invention further provides an in vitro method for inhibiting protein kinase activity which comprises contacting the kinase with an effective amount of a compound of formula (I) as defined above.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with anticancer activity.

Finally, the invention provides a compound of formula (I) or a pharmaceutically acceptable salt thereof, as defined above, for use in a method of treating cancer.

Unless otherwise specified, when referring to the compounds of the formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

In other words, if easily obtainable from the compounds of the formula (I) as defined above, also their isomers, tautomers, hydrates, solvates, complexes, metabolites, prodrugs, carriers and N-oxides are object of the present invention.

A metabolite of a compound of the formula (I) is any compound into which this same compound of the formula (I) is converted in vivo, for instance upon administration to a mammal in need thereof. Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of the formula (I).

Prodrugs are any covalently bonded compounds, which release in vivo the active parent drug according to the formula (I).

N-oxides are compounds of the formula (I) wherein nitrogen and oxygen are tethered through a dative bond.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

In case wherein Y is O and Z is N, the compound of the present invention has the general formula (Ia), in case wherein Y is N and Z is O, the compound of the present invention has the general formula (Ib) below:

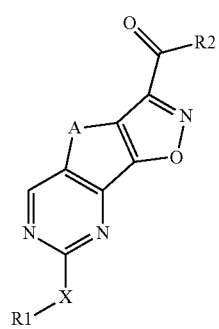

(Ia)

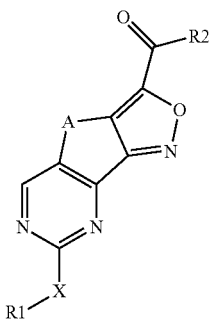

(Ib)

wherein R1, R2, X and A are as defined above.

The term aryl includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms selected from N, O and S.

Non limiting examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_3$-$C_7$ cycloalkyl", we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above R1, R2, R' and R" group may be optionally substituted, in any of their free positions, by one or more groups, for instance 1 to 6 groups, independently selected from: halogen atom, nitro, oxo groups (=O), cyano, $C_1$-$C_6$ alkyl, polyfluorinated alkyl, polyfluorinated alkoxy, alkenyl, alkynyl, hydroxyalkyl, aryl, arylalkyl, heterocyclyl, $C_3$-$C_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term halogen atom we intend a fluorine, chlorine, bromine or iodine atom.

With the term cyano we intend a —CN residue.

With the term nitro we intend a —$NO_2$ group.

With the term alkenyl or alkynyl we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term polyfluorinated alkyl or alkoxy we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term alkoxy, aryloxy, heterocyclyloxy and derivatives thereof we intend any of the above $C_1$-$C_6$ alkyl, aryl or heterocyclyl groups linked to the rest of the molecule through an oxygen atom (—O—).

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

Preferred compounds of the formula (I) are the compounds wherein:

X is O, S or NH;
R1 is an optionally substituted heterocyclyl or aryl, and
R2 is —NR'R" or OR' wherein R' and R" are, each independently, hydrogen or an optionally substituted group selected from straight or branched $C_1$-$C_6$ alkyl, $C_3$-$C_7$ cycloalkyl, cycloalkyl-alkyl, heterocyclyl, eterocyclylalkyl, aryl and arylalkyl, and
Y, Z and A are as defined above.

More preferred compounds of the formula (I) are the compounds wherein:

R1 is an optionally substituted aryl, and
Y, Z, X, R2 and A are as defined above.

A particularly preferred class of compounds of formula (I) are the compounds wherein:

R2 is NR'R", wherein R' and R" are independently hydrogen or an optionally substituted group selected from $C_1$-$C_6$ alkyl, cycloalkyl, aryl and heterocyclyl, and
Y, Z, X, R1 and A are as defined above.

Preferred specific compounds of the formula (I) are the compounds listed below:

1) N-(2,6-diethylphenyl)-8-{[2-methoxy-4-(4-methylpiperazin-1-yl)phenyl]amino}-4,5-dihydroisoxazolo[4,3-h]quinazoline-3-carboxamide,
2) 8-[(4-bromo-2-methoxyphenyl)amino]-N,N-dimethyl-4,5-dihydroisoxazolo[4,3-h]quinazoline-3-carboxamide,
3) ethyl 8-{[4-(4-methylpiperazin-1-yl)phenyl]amino}-4,5-dihydroisoxazolo[4,3-h]quinazoline-3-carboxylate,
4) 8-{[4-(4-methylpiperazin-1-yl)phenyl]amino}-4,5-dihydroisoxazolo[4,3-h]quinazoline-3-carboxamide,
5) N-(2,6-diethylphenyl)-8-{[4-(4-methylpiperazin-1-yl)phenyl]amino}-4,5-dihydroisoxazolo[4,3-h]quinazoline-3-carboxamide,
6) ethyl 8-[(4-bromo-2-methoxyphenyl)amino]-4,5-dihydroisoxazolo[4,3-h]quinazoline-3-carboxylate,
7) ethyl 8-amino-4,5-dihydroisoxazolo[4,3-h]quinazoline-3-carboxylate,
8) N-(2,6-diethylphenyl)-8-({4-[4-(2-hydroxyethyl)piperazin-1-yl]-2-methoxyphenyl}amino)-4,5-dihydroisoxazolo[4,3-h]quinazoline-3-carboxamide,
9) N-(2,6-diethylphenyl)-8-{[2-methoxy-4-(4-pyrrolidin-1-ylpiperidin-1-yl)phenyl]amino}-4,5-dihydroisoxazolo[4,3-h]quinazoline-3-carboxamide,
10) 8-[(4-bromo-2-methoxyphenyl)amino]-4,5-dihydroisoxazolo[4,3-h]quinazoline-3-carboxylic acid
11) ethyl 8-{[2-methoxy-4-(4-methylpiperazin-1-yl)phenyl]amino}-4,5-dihydroisoxazolo[4,3-h]quinazoline-3-carboxylate,
12) 8-{[2-methoxy-4-(4-methylpiperazin-1-yl)phenyl]amino}-4,5-dihydroisoxazolo[4,3-h]quinazoline-3-carboxamide,
13) ethyl 8-{[4-(tert-butoxycarbonyl)-2-methoxyphenyl]amino}-4,5-dihydroisoxazolo[4,3-h]quinazoline-3-carboxylate,
14) 4-{[3-(ethoxycarbonyl)-4,5-dihydroisoxazolo[4,3-h]quinazolin-8-yl]amino}-3-methoxybenzoic acid
15) 5,5-dimethyl-8-{[4-(4-methylpiperazin-1-yl)-2-(trifluoromethoxy)phenyl]amino}-4,5-dihydroisoxazolo[4,3-h]quinazoline-3-carboxamide,
16) 8-amino-4,5-dihydroisoxazolo[4,3-h]quinazoline-3-carboxamide,
17) N-(2,6-diethylphenyl)-8-[(4-{[2-(dimethylamino)ethyl]carbamoyl}-2-methoxyphenyl)amino]-4,5-dihydroisoxazolo[4,3-h]quinazoline-3-carboxamide,
18) N-(2,6-diethylphenyl)-8-[(4-{[4-(dimethylamino)piperidin-1-yl]carbonyl}-2-methoxyphenyl)amino]-4,5-dihydroisoxazolo[4,3-h]quinazoline-3-carboxamide,
19) N-(2,6-diethylphenyl)-8-[(2-methoxy-4-{[(2S)-2-(pyrrolidin-1-ylmethyl)pyrrolidin-1-yl]carbonyl}phenyl)amino]-4,5-dihydroisoxazolo[4,3-h]quinazoline-3-carboxamide,
20) ethyl 8-{[4-(4-methylpiperazin-1-yl)-2-(trifluoromethoxy)phenyl]amino}-4,5-dihydroisoxazolo[4,3-h]quinazoline-3-carboxylate,
21) N-(2,6-diethylphenyl)-8-[(2-methoxy-4-{[(2R)-2-(pyrrolidin-1-ylmethyl)pyrrolidin-1-yl]carbonyl}phenyl)amino]-4,5-dihydroisoxazolo[4,3-h]quinazoline-3-carboxamide,
22) N-(2,6-diethylphenyl)-8-{[4-(4-methylpiperazin-1-yl)-2-(trifluoromethoxy)phenyl]amino}-4,5-dihydroisoxazolo[4,3-h]quinazoline-3-carboxamide,
23) 8-[(4-bromo-2-methoxyphenyl)amino]-N-(2,6-diethylphenyl)-4,5-dihydroisoxazolo[4,3-h]quinazoline-3-carboxamide,
24) 8-{[4-(4-methylpiperazin-1-yl)-2-(trifluoromethoxy)phenyl]amino}-4,5-dihydroisoxazolo[4,3-h]quinazoline-3-carboxamide,
25) N-(2,6-diethylphenyl)-8-({4-[4-(dimethylamino)piperidin-1-yl]-2-methoxyphenyl}amino)-4,5-dihydroisoxazolo[4,3-h]quinazoline-3-carboxamide,
26) N-(2,6-diethylphenyl)-8-[(4-{[2-(dimethylamino)ethyl](methyl)amino}-2-methoxyphenyl)amino]-4,5-dihydroisoxazolo[4,3-h]quinazoline-3-carboxamide,
27) 5,5-dimethyl-8-{[4-(4-methylpiperazin-1-yl)phenyl]amino}-4,5-dihydroisoxazolo[4,3-h]quinazoline-3-carboxamide,
28) 5,5-dimethyl-8-{[4-(4-methylpiperazin-1-yl)phenyl]amino}-N-(pyridin-4-ylmethyl)-4,5-dihydroisoxazolo[4,3-h]quinazoline-3-carboxamide,
29) ethyl 8-({2-methoxy-4-[(1-methylpiperidin-4-yl)carbamoyl]phenyl}amino)-4,4-dimethyl-4,5-dihydroisoxazolo[4,3-h]quinazoline-3-carboxylate,
30) 8-({2-methoxy-4-[(1-methylpiperidin-4-yl)carbamoyl]phenyl}amino)-4,4-dimethyl-4,5-dihydroisoxazolo[4,3-h]quinazoline-3-carboxamide,
31) methyl 8-[(4-bromo-2-methoxyphenyl)amino]-4,5-dihydroisoxazolo[4,3-h]quinazoline-3-carboxylate
32) 8-({2-methoxy-4-[(1-methylpiperidin-4-yl)carbamoyl]phenyl}amino)-5,5-dimethyl-4,5-dihydroisoxazolo[4,3-h]quinazoline-3-carboxamide,
33) N-[(1S)-2-amino-1-phenylethyl]-8-({2-methoxy-4-[(1-methylpiperidin-4-yl)carbamoyl]phenyl}amino)-5,5-dimethyl-4,5-dihydroisoxazolo[4,3-h]quinazoline-3-carboxamide,
34) N-[(1S)-2-amino-1-phenylethyl]-8-({2-methoxy-4-[(1-methylpiperidin-4-yl)carbamoyl]phenyl}amino)-4,4-dimethyl-4,5-dihydroisoxazolo[4,3-h]quinazoline-3-carboxamide
35) tert-butyl [(2S)-2-({[8-({2-methoxy-4-[(1-methylpiperidin-4-yl)carbamoyl]phenyl}amino)-5,5-dimethyl-4,5-dihydroisoxazolo[4,3-h]quinazolin-3-yl]carbonyl}amino)-2-phenylethyl]carbamate,
36) tert-butyl [(2S)-2-({[8-({2-methoxy-4-[(1-methylpiperidin-4-yl)carbamoyl]phenyl}amino)-4,4-dimethyl-4,5-dihydroisoxazolo[4,3-h]quinazolin-3-yl]carbonyl}amino)-2-phenylethyl]carbamate, 37) ethyl 8-({2-methoxy-4-[(1-methylpiperidin-4-yl)carbamoyl]phenyl}amino)-5,5-dimethyl-4,5-dihydroisoxazolo[4,3-h]quinazoline-3-carboxylate,
38) 8-{[2-methoxy-4-(4-methylpiperazin-1-yl)phenyl]amino}-4,5-dihydroisoxazolo[4,3-h]quinazoline-3-carboxylic acid,
39) 8-[(4-bromo-2-methoxyphenyl)amino]-N-(2,6-diethylphenyl)-4,5-dihydroisoxazolo[4,5-h]quinazoline-3-carboxamide,
40) methyl 8-[(4-bromo-2-methoxyphenyl)amino]-4,5-dihydroisoxazolo[4,5-h]quinazoline-3-carboxylate,
41) N-(2,6-diethylphenyl)-8-{[2-methoxy-4-(4-methylpiperazin-1-yl)phenyl]amino}-4,5-dihydroisoxazolo[4,5-h]quinazoline-3-carboxamide,
42) 8-{[4-(4-methylpiperazin-1-yl)phenyl]amino}-4,5-dihydroisoxazolo[4,5-h]quinazoline-3-carboxamide,
43) N-(2,6-diethylphenyl)-8-{[2-methoxy-4-(4-pyrrolidin-1-ylpiperidin-1-yl)phenyl]amino}-4,5-dihydroisoxazolo[4,5-h]quinazoline-3-carboxamide,
44) 4-{[3-(ethoxycarbonyl)-4,5-dihydroisoxazolo[4,5-h]quinazolin-8-yl]amino}-3-methoxybenzoic acid,
45) ethyl 8-[(4-bromo-2-methoxyphenyl)amino]-4,5-dihydroisoxazolo[4,5-h]quinazoline-3-carboxylate,
46) N-(2,6-diethylphenyl)-8-({4-[4-(2-hydroxyethyl)piperazin-1-yl]-2-methoxyphenyl}amino)-4,5-dihydroisoxazolo[4,5-h]quinazoline-3-carboxamide,
47) N-(2,6-diethylphenyl)-8-({4-[4-(dimethylamino)piperidin-1-yl]-2-methoxyphenyl}amino)-4,5-dihydroisoxazolo[4,5-h]quinazoline-3-carboxamide,
48) ethyl 8-{[4-(tert-butoxycarbonyl)-2-methoxyphenyl]amino}-4,5-dihydroisoxazolo[4,5-h]quinazoline-3-carboxylate,
49) N-(2,6-diethylphenyl)-8-[(4-{[4-(dimethylamino)piperidin-1-yl]carbonyl}-2-methoxyphenyl)amino]-4,5-dihydroisoxazolo[4,5-h]quinazoline-3-carboxamide,
50) 5,5-dimethyl-8-{[4-(4-methylpiperazin-1-yl)phenyl]amino}-4,5-dihydroisoxazolo[4,5-h]quinazoline-3-carboxamide,
51) ethyl 5,5-dimethyl-8-{[4-(4-methylpiperazin-1-yl)phenyl]amino}-4,5-dihydroisoxazolo[4,5-h]quinazoline-3-carboxylate,
52) ethyl 8-{[4-(4-methylpiperazin-1-yl)-2-(trifluoromethoxy)phenyl]amino}-4,5-dihydroisoxazolo[4,5-h]quinazoline-3-carboxylate,
53) 8-{[4-(4-methylpiperazin-1-yl)-2-(trifluoromethoxy)phenyl]amino}-4,5-dihydroisoxazolo[4,5-h]quinazoline-3-carboxamide,
54) N-(2,6-diethylphenyl)-8-{[4-(4-methylpiperazin-1-yl)-2-(trifluoromethoxy)phenyl]amino}-4,5-dihydroisoxazolo[4,5-h]quinazoline-3-carboxamide,
55) 8-({2-methoxy-4-[(1-methylpiperidin-4-yl)carbamoyl]phenyl}amino)-5,5-dimethyl-4,5-dihydroisoxazolo[4,5-h]quinazoline-3-carboxamide,
56) ethyl 8-({2-methoxy-4-[(1-methylpiperidin-4-yl)carbamoyl]phenyl}amino)-5,5-dimethyl-4,5-dihydroisoxazolo[4,5-h]quinazoline-3-carboxylate,
57) N-[(1S)-2-amino-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide,
58) N-[2-(1H-imidazol-4-yl)ethyl]-5,5-dimethyl-8-{[4-(4-methylpiperazin-1-yl)phenyl]amino}-4,5-dihydroisoxazolo[4,5-h]quinazoline-3-carboxamide,
59) 5,5-dimethyl-8-{[4-(4-methylpiperazin-1-yl)phenyl]amino}-N-(pyridin-4-ylmethyl)-4,5-dihydroisoxazolo[4,5-h]quinazoline-3-carboxamide,
60) N-[(2R)-2-amino-2-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide,
61) N-[(1R)-2-amino-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide,
62) 5,5-dimethyl-8-{[4-(4-methylpiperazin-1-yl)-2-(trifluoromethoxy)phenyl]amino}-4,5-dihydroisoxazolo[4,5-h]quinazoline-3-carboxamide,
63) ethyl 8-{[2-methoxy-4-(4-methylpiperazin-1-yl)phenyl]amino}-4,5-dihydroisoxazolo[4,5-h]quinazoline-3-carboxylate,
64) ethyl 8-{[4-(4-methylpiperazin-1-yl)phenyl]amino}-4,5-dihydroisoxazolo[4,5-h]quinazoline-3-carboxylate,
65) 8-{[2-methoxy-4-(4-methylpiperazin-1-yl)phenyl]amino}-4,5-dihydroisoxazolo[4,5-h]quinazoline-3-carboxylic acid,
66) ethyl 8-(methylsulfanyl)-4,5-dihydroisoxazolo[4,5-h]quinazoline-3-carboxylate,
67) 8-(methylsulfanyl)-4,5-dihydroisoxazolo[4,5-h]quinazoline-3-carboxamide,
68) 8-[4-(4-methylpiperazin-1-yl)phenoxy]-4,5-dihydroisoxazolo[4,5-h]quinazoline-3-carboxamide,
69) 8-[4-(4-methylpiperazin-1-yl)phenoxy]isoxazolo[4,5-h]quinazoline-3-carboxamide,
70) ethyl 8-(methylsulfanyl)-4,5-dihydroisoxazolo[4,3-h]quinazoline-3-carboxylate,
71) 8-(methylsulfanyl)-4,5-dihydroisoxazolo[4,3-h]quinazoline-3-carboxamide,
72) 8-[4-(4-methylpiperazin-1-yl)phenoxy]-4,5-dihydroisoxazolo[4,3-h]quinazoline-3-carboxamide,
73) 8-(methylsulfonyl)-4,5-dihydroisoxazolo[4,5-h]quinazoline-3-carboxamide,
74) 8-(methylsulfonyl)-4,5-dihydroisoxazole[4,3-h]quinazoline-3-carboxamide,
75) 8-({2-methoxy-4-[(1-methylpiperidin-4-yl)carbamoyl]phenyl}amino)-5,5-dimethyl-4,5-dihydroisoxazolo[4,5-h]quinazoline-3-carboxylic acid,
76) 5,5-dimethyl-8-{[4-(4-methylpiperazin-1-yl)phenyl]amino}-4,5-dihydroisoxazolo[4,5-h]quinazoline-3-carboxylic acid and
77) N-[(2S)-2-amino-2-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide.

For a reference to any specific compound of the formula (I) of the invention, optionally in the form of a pharmaceutically acceptable salt, see the experimental section and claims.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The reported Scheme 1 shows the preparation of a compound of formula (I).

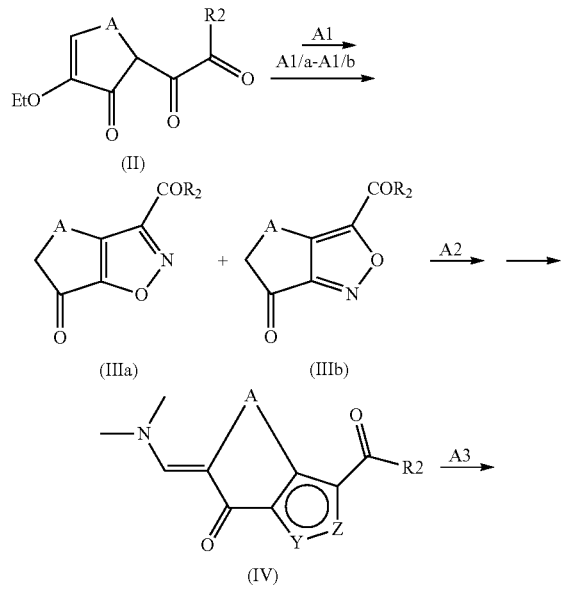

In the above scheme R2 is O—$C_1$-$C_4$ alkyl, A is a divalent group selected from —$(CH_2)_2$—, —$CH_2$—$C(CH_3)_2$— and —$C(CH_3)_2$—$CH_2$—; X is as defined above except $SO_2$, R1, Y and Z are as defined above.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises:
st.A1) reacting a compound of the formula (II):

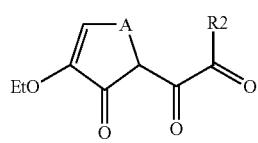

wherein R2 is O—$C_1$-$C_4$ alkyl, A is a divalent group selected from —$(CH_2)_2$—, —$CH_2$—$C(CH_3)_2$— and —$C(CH_3)_2$—$CH_2$—, with hydroxylamine HO—$NH_2$HCl, optionally in the presence of a $C_1$-$C_4$ alkyl alcohol, and separating the resultant compounds of formula (IIIa) and (IIIb):

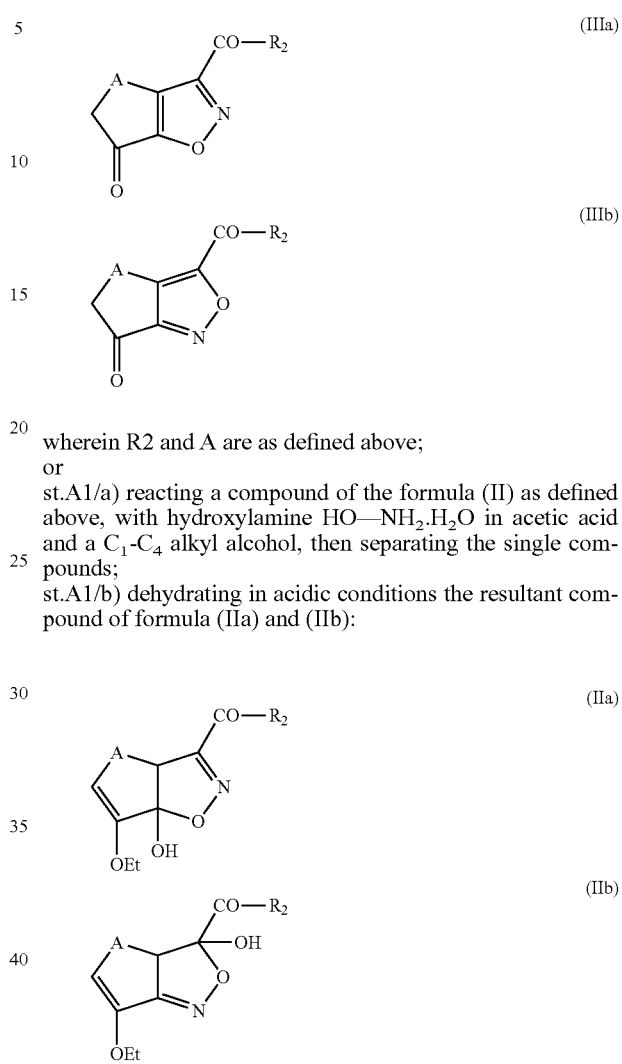

wherein R2 and A are as defined above;
or
st.A1/a) reacting a compound of the formula (II) as defined above, with hydroxylamine HO—$NH_2$.$H_2O$ in acetic acid and a $C_1$-$C_4$ alkyl alcohol, then separating the single compounds;
st.A1/b) dehydrating in acidic conditions the resultant compound of formula (IIa) and (IIb):

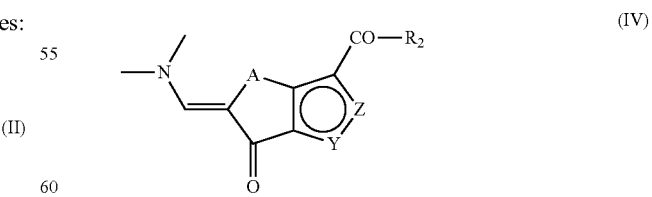

wherein R2 and A are as defined above, to give the compounds of formula (IIIa) and (IIIb) as defined above;
st.A2) reacting the compound of the formula (IIIa) or (IIIb), obtained in st.A1 or in st.A1/b, with an N—N-dimethylformamide derivative;
st.A3) reacting the resultant compound of the formula (IV):

wherein R2, A, Y and Z are as defined above, with a compound of the formula (V):

R1-X—C(=NH)$NH_2$    (V)

wherein X is as defined above except $SO_2$ and R1 is as defined above, to give a compound of the formula (I):

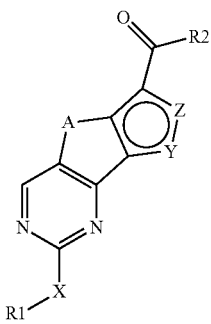

(I)

wherein R1, Y and Z are as defined above, R2 is O—C$_1$-C$_4$ alkyl, A is a divalent group selected from —(CH$_2$)$_2$—, —CH$_2$—C(CH$_3$)$_2$— and —C(CH$_3$)$_2$—CH$_2$—, and X is as defined above except SO$_2$, and optionally converting a compound of the formula (I) into another different compound of the formula (I), and, if desired, converting a compound of the formula (I) into a pharmaceutically acceptable salt thereof or converting a salt into the free compound (I).

A compound of formula (I) which is prepared according to the process object of the invention, can be conveniently converted into the corresponding compound of formula (I) by operating according to well-known synthetic conditions, the following being examples of possible conversions:

Conv.a) converting a compound of formula (I) wherein R2 is —OC$_1$-C$_4$ into the corresponding compound of formula (I) wherein R2 is a hydroxyl group or corresponding salt through an hydrolysis under acid or basic conditions;

Conv.b) converting a compound of formula (I) wherein R2 is —OH or corresponding salt into the corresponding compound of formula (I) wherein R2 is a group —NR'R", wherein R' and R" are as defined above, through reaction with an amine of formula R'R"—NH (VI) wherein R' and R" are as defined above, under basic conditions and in the presence of a suitable condensing agent;

Conv.c) converting a compound of formula (I) wherein R2 is —OC$_1$-C$_4$ into the corresponding compound of formula (I) wherein R2 is a group —NR'R", wherein R' and R" are as defined above, by treatment with an amine of formula R'R"—NH (VI), as defined above;

Conv.d) converting a compound of formula (I) wherein X is as defined above except SO$_2$, and R1 is an aryl, i.e. phenyl, substituted by bromine, into the corresponding compound of formula (I) wherein R1 is an aryl, i.e. phenyl, substituted by NR'R", by treatment with an amine of formula R'R"—NH (VI), wherein R' and R" are as defined above:

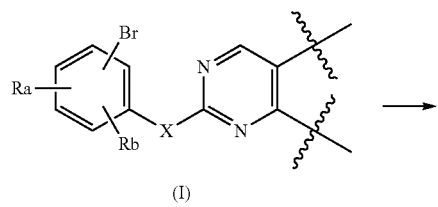

(I)

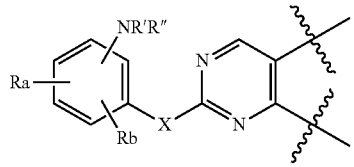

(I)

wherein Ra and Rb are independently halogen atom, except bromine, nitro, cyano, C$_1$-C$_6$ alkyl, polyfluorinated alkyl, polyfluorinated alkoxy, alkenyl, alkynyl, hydroxyalkyl, aryl, arylalkyl, heterocyclyl, C3-C7 cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

Conv.e) converting a compound of formula (I) wherein X is as defined in formula (I) and R1 is an aryl, i.e. phenyl, substituted by —COOPg, wherein Pg is a suitable protecting group, into the corresponding compound of formula (I) wherein R1 is an aryl, i.e. phenyl, substituted by —COOH, through conditions well known in the literature (see Teodora W. Green, Pere G. M. Wuts):

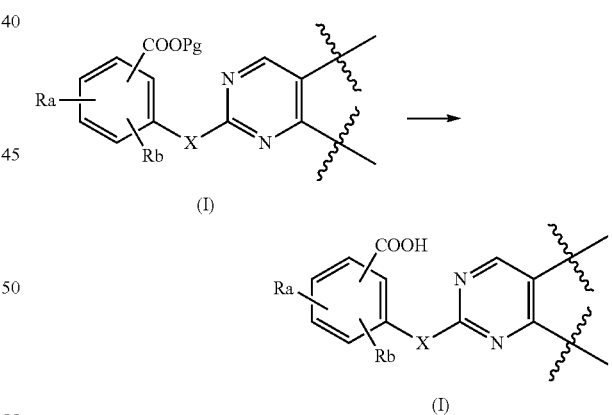

wherein Ra and Rb are independently halogen atom, nitro, cyano, C$_1$-C$_6$ alkyl, polyfluorinated alkyl, polyfluorinated alkoxy, alkenyl, alkynyl, hydroxyalkyl, aryl, arylalkyl, heterocyclyl, C3-C7 cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, dialkylamino, arylamino, diarylamino, heterocyclyamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate or alkylphosphonate;

Conv.f) converting a compound of formula (I) wherein X is as defined in formula (I) and R1 is an aryl, i.e. phenyl, substituted by —COOH, into the corresponding compound of formula (I) wherein R1 is an aryl, i.e. phenyl, substituted by —CONR'R", wherein R' and R" are as defined above, by treatment with an amine of formula R'R"—NH (VI), in the presence of the suitable condensing agents:

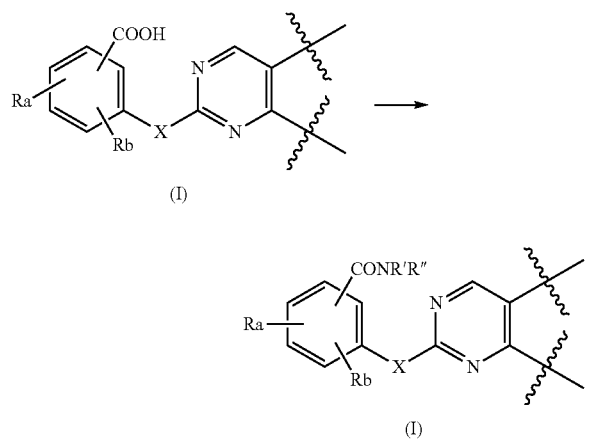

wherein Ra and Rb are as defined in Conv.e);

Conv.g) converting a compound of formula (I) wherein A is a —CH$_2$.CH$_2$— group into the corresponding compound of formula (I) wherein A is a —CH═CH— group, under dehydrogenating operative conditions in the presence of a Pd or Pt catalyst or with 2,3-dichloro-5,6-dicyanobenzoquinone (DDQ):

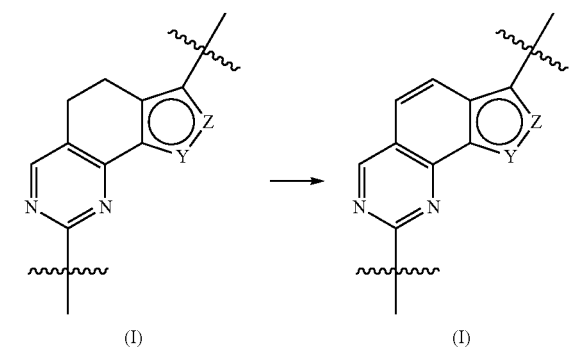

Conv.h) converting a compound of formula (I) wherein X is —S— and R1 is alkyl, e.g. methyl, into the corresponding compound of formula (I) wherein and X is SO$_2$, under oxidative condition:

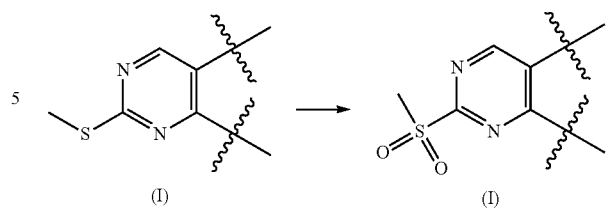

Conv.j) converting a compound of formula (I) wherein R2 is a group O—C$_1$-C$_4$ alkyl into the corresponding compound of formula (I) wherein R2 is a different group O—C$_1$-C$_4$ alkyl, by reacting with an alcohol of formula HO—C$_1$-C$_4$(VIII);

Conv.k) converting a compound of formula (I) wherein R1 is e.g. methyl and X is SO$_2$, into the corresponding compound of formula (I) wherein R1 is as defined above and X is —O—, by reacting the sulfonyl derivative with a compound of formula R1-OH (VII):

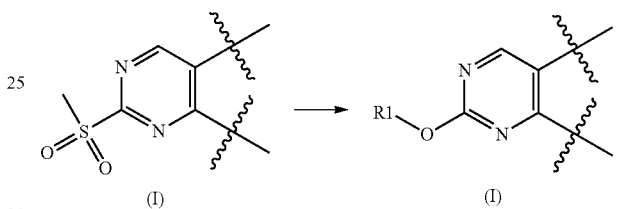

All the above processes, in any one of the aforementioned variants, are analogy processes which can be carried out according to well known methods and under suitable conditions known in the art.

According to step (st.A1) of the process, a compound of the formula (II) is reacted with HO—NH$_2$.HCl. Preferably, the above reaction is carried out in ethanol at a temperature ranging from room temperature to reflux, so as to obtain a mixture of both compounds of formula (IIIa) and (IIIb). Their separation into the single compounds (IIIa) and (IIIb) is carried out under conventional methods, for instance through preparative HPLC.

According to step (st A1/a) a compound of formula (II) is reacted with HO—NH$_2$.H$_2$O in acetic acid and a C$_1$-C$_4$ alkyl alcohol, preferably ethanol, at room temperature so to obtain a mixture of compounds of formula (IIa) and (IIb) which were separated into single compound under conventional methods, for instance through preparative HPLC.

According to step (st A1/b) single compounds (IIa) and (IIb) are reacted with an acid such as hydrochloric acid so to obtain respectively the compound (IIIa) or (IIIb). Preferably the above reaction is carried out in ethanol at a temperature ranging from room temperature to reflux.

According to step (st.A2) of the process, the compound of the formula (IIIa) or (IIIb) is reacted with N,N-dimethylformamide-di-tert-butylacetale, N,N-dimethylformamide-diisopropylacetale or N,N-dimethylformamide-diethylacetale in a suitable solvent such as, for instance, N,N-dimethylformamide or toluene, so as to get the compounds of the formula (IV) as defined above. Preferably, the reaction is carried out at a temperature ranging from room temperature to about 100° C.

According to step (st.A3) of the process, the compound of the formula (IV) as defined above is reacted with a compound of formula (V) as defined above so to obtain a compound of the formula (I) as defined above through pyrimidine ring formation. The reaction, is carried out in N,N-dimethylformamide or ethanol at a temperature ranging from 80° C. to reflux eventually in the presence of a base e.g. potassium carbonate.

According to conversion (con.a) of the process, a compound of the formula (I) wherein R2 is —OC$_1$-C$_4$, may be converted into the corresponding compound of the formula (I) wherein R2 is a hydroxyl group or its salt, by conditions widely known in the art and may comprise, for instance, the reaction with sodium or potassium hydroxide in the presence of a suitable solvent such as a lower alcohol, N,N-dimethylformamide or mixtures thereof; preferably the reaction is carried out with sodium hydroxide in a methanol/N,N-dimethylformamide mixture, at a temperature ranging from about 50° C. to about 100° C.

According to conversion (con.b) of the process, a compound of the formula (I) wherein R2 is hydroxyl or a salt thereof, may be converted into the corresponding compound of the formula (I) wherein R2 is a group —NR'R" by conditions widely known in the art. The reaction is carried out in the presence of an amine of formula (VI), under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may also be required.

According to conversion (con.c) of the process, a compound of the formula (I) wherein R2 is —OC$_1$-C$_4$, may be converted into the corresponding compound of the formula (I) wherein R2 is an amino group of formula —NR'R" according to methods well-known in the art to convert carboxyester groups (—COOR') into carboxamides (—CONH$_2$), N-substituted carboxamides (—CONHR') and N,N-disubstituted carboxamides (—CONR'R"). When R' and R" are hydrogen, preferably the reaction is carried out with ammonium hydroxide in a methanol/N,N-dimethylformamide mixture, at a temperature ranging from about 50° C. to about 100° C.

Analogous operative conditions are applied in the preparation of N-substituted carboxamides or N,N-disubstituted carboxamides wherein a suitable primary or secondary amine are used in place of ammonia or ammonium hydroxide.

Alternatively, carboxyester groups may be converted into carboxamide or N-substituted carboxamides or N,N-disubstituted carboxamides under basic conditions such as lithium bis-trimethylsilylamide 1 N in THF, using ammonium chloride or a suitable primary or secondary amine; preferably the reaction is carried out in tetrahydrofuran at a temperature ranging from 20° C. to reflux.

According to conversion (con.d) of the process, replacement of bromine with —NR'R" moiety was achieve reacting the starting material with an amine of the formula (VI) as defined above, in a suitable solvent such as tetrahydrofurane or dioxane, and in the presence of catalytic amounts preferably of tris(dibenzilideneacetone)dipalladium, 2-dicyclohexylphosphino-2'-(N,N-dimethylamino)-biphenyl and a base such as LiN(TMS)$_2$ at a temperature ranging from room temperature to reflux and for a time ranging from 1 to about 24 hours.

According to conversion (con.e) of the process, deprotection of the carboxylic residue into the corresponding acid can be achieved using procedure well known in the art e.g. by reaction in acidic condition for example with hydrochloric acid or trifluoric acid in a suitable solvent, for instance, tetrahydrofurane or dioxane, at a temperature ranging from room temperature to 60° C. and for a time ranging from about 1 to about 12 hours.

According to conversion (con.f) of the process, transformation of the acid residue into the corresponding amide derivatives —CONR'R", wherein R' and R" are as defined above, can be obtained by reaction of the acid derivatives with an amine of the formula (VI) as defined above, under basic conditions, preferably with N,N-diisopropyl-N-ethylamine or triethylamine, in a suitable solvent such as dichloromethane, N,N-dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required, at a temperature ranging from room temperature to 60° C. and for a time ranging from about 1 to about 24 hours.

According to conversion (con.g) of the process, a compound of the formula (I) wherein A represents a —CH$_2$—CH$_2$— group can undergo dehydrogenation in the presence of an optionally supported palladium or platinum catalyst or with 2,3-dichloro-5,6-dicyanobenzoquinone, so as to give rise to the corresponding aromatic derivative wherein A is —CH=CH—.

According to conversion (con.h) of the process, the transformation of alkylthio group into the alkylsulfonyl group can be obtained by reaction with an oxidant such as mCPBA in the presence of a suitable solvent preferably dichloromethane (DCM) at room temperature.

According to conversion (con.j) of the process, the transformation of alkyloxy group into another different alkyloxy group can be obtained by reaction with an alcohol of formula R2-OH at reflux temperature.

According to conversion (con.k) of the process, a compound of the formula (I) wherein R1 is as defined above and X is —O— may be easily obtained reacting the sulfonyl derivative with a phenol derivative of formula (VII) R1-OH. The reaction may be carried out in the presence of a base such as potassium or sodium carbonate, sodium or lithium hydroxide or the like, in a suitable solvent such as N,N-dimethylformamide or dimethylsulfoxide, and by working a temperature ranging from room temperature to about 100° C.

Interestingly, during this reaction a mixture of desired products of formula (I) were obtained, wherein A is a group —CH2-CH2-, or —CH=CH—. These two derivatives are then resolved from the reaction mixture according to conventional methods, for instance by chromatography or by preparative HPLC.

Needless to say, also any of the intermediates of the above described processes could be converted into a different intermediate, if wanted and necessary, by operating in an analogous way as in any one of the conversion reaction here above described.

From all of the above it is clear to the skilled person that any compound of the formula (I) bearing a functional group which can be further derivatized to another functional group, by working according to methods well known in the art thus leading to other compounds of the formula (I), is intended to be comprised within the scope of the present invention.

It is also clear to the skilled person that when necessary reactive groups that may be protected and then removed according to methods well known in the literature e.g. protective groups in organic synthesis.

According to any variant of the process for preparing the compounds of the formula (I), the starting materials and any other reactants are known or easily prepared according to known methods.

As an example, whilst the starting material of the compounds of the formula (II) are commercially available, the compounds of the formula (II) can be prepared as described in WO04/104007. Compounds of the formula (V) are either commercially available or can be prepared as described in WO04/104007, WO09/156,315 or in the experimental part below.

Compounds of the formula (VI) are either commercially available or can be prepared as described in the experimental part below.

Compounds of the formula (VII) can be prepared by known methods or as described in the experimental part below.

Compounds of the formula (VIII) are commercially available or can be prepared by known methods.

From all of the above, it is clear to the skilled person that when preparing the compounds of the formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of the formula (I) prepared according to the process described above are obtained as mixture of isomers, their separation using conventional techniques into the single isomers of the formula (I), is within the scope of the present invention.

Conventional techniques for racemate resolution include, for instance, partitioned crystallization of diastereoisomeric salt derivatives or preparative chiral HPLC.

In addition, the compounds of the formula (I) of the invention may be also prepared according to combinatorial chemistry techniques widely known in the art, for instance by accomplishing the aforementioned reactions between the several intermediates in a parallel and/or serial manner and by working under solid-phase-synthesis (SPS) conditions.

Pharmacology

The compounds of the formula (I) are active as protein kinase inhibitors and are therefore useful, for instance, to restrict the unregulated proliferation of tumour cells.

In therapy, they may be used in the treatment of various tumours, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The inhibiting activity of putative MPS1 and PERK inhibitors and the potency of selected compounds was determined through the assays below described.

The short forms and abbreviations used herein have the following meaning:

Ci Curie
DMSO dimethylsulfoxide
KDa kiloDalton
microCi microCurie
mg milligram
microg microgram
ng nanogram
L liter
mL milliliter
microL microliter
M molar
mM millimolar
microM micromolar
nM nanomolar
Et ethyl Cloning, Expression and Purification of Recombinant MPS1 Full Length Protein.

MPS1 full length (corresponding to residues 2-857 of the full length sequence, see Swiss-Prot accession number P33981) was PCR amplified from the full-length human MPS1 gene present in house as clone pGEX4t_MPS1.

Amplification was performed using the forward oligonucleotide:

5'ggggacaagtttgtacaaaaaagcaggcttactggaagttctgttccaggggcccgaatccgaggatttaagtggcagag3' and the reverse oligonucleotide:

5'ggggaccactttgtacaagaaagctgggttttattttttcccctttttttttcaaaagtcttggaggatgaag3'].

Both the oligonucleotides are described in WO2009/156315, published on 30 Dec. 2009.

For cloning purposes, the oligonucleotides included attB sites in order to obtain an attB-flanked PCR product suitable for cloning using the Gateway® technology (Invitrogen). Furthermore, for purification purposes, forward primer included a protease cleavage site. The resulting PCR product was cloned in the pDONR201 plasmid and then transferred in the baculovirus expression vector pVL1393GST (Invitrogen) Gateway®-modified. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 72 hours of infection at 21° C., cells were recovered, pelletted and freezed at −80° C. For purification of recombinant protein, pellet was thawed, resuspended in lysis buffer (PBS, NaCl 150 mM, Glycerol 10%, CHAPS 0.1%, DTT 20 mM, protease and phosphatase inhibitors) and lysed by Gaulin. Lysate was cleared by centrifugation and loaded on a GST affinity column. After extensive wash, recombinant protein was cleaved by a specific protease and eluted by incubation.

To get a fully activated enzyme, the protein was then subjected to auto-phosphorylation in presence of ATP 1 mM at 25° C. for 2 hours in kinase buffer (Hepes pH7.5 50 mM, MgCl2 2.5 mM, MnCl2 1 mM, DTT 1 mM, phosphatase inhibitors); ATP was then removed whit a desalting column.

Cloning, Expression and Purification of Recombinant PERK Cytoplasmic Domain Protein.

PERK cytoplasmic domain (corresponding to residues 540-1115; Swiss-Prot accession number Q9NZJ5) was PCR amplified using the following forward oligonucleotide:

[SEQ ID NO: 1]
5'ggggacaagtttgtacaaaaaagcaggcttactggaagttctgttccaggggccccgcaggcttttccatcctcatc3' and the following reverse oligonucleotide:

[SEQ ID NO: 2]
5'ggggaccactttgtacaagaaagctgggttttaattgcttggcaaagggctatgg3' (reverse).

The oligonucleotides included attB sites in order to obtain an attB-flanked PCR product suitable for cloning using the Gateway® technology (Invitrogen). The resulting PCR product was cloned in the pDONR221 plasmid and then transferred in the *Escherichia coli* expression vector pGEX Gateway® modified; the vector included the coding sequence for a his tag fused in frame with the 5' of GST coding sequence, in order to have a double affinity tag, useful for purification. The sequence coding for a protease cleavage site was included, in order to remove the tag. Cloning was performed according to the protocols described in the Gateway® manual.

Recombinant protein was produced in BL21(DE3)pLysS strain, in auto-induction medium, at 21° C. for 24 hours (see F. W. Studier, "Protein production by auto-induction in high density shaking cultures", Protein Expression and Purification (2005) vol. 41:207-234). The cells were recovered by centrifugation, and the pellet frozen at −80° C. For purification of recombinant protein, pellet was thawed, resuspended in lysis buffer (Tris-HCl 50 mM pH 7.6, NaCl 250 mM, Glycerol 10%, CHAPS 0.2%, Imidazole 5 mM, protease and phosphatase inhibitors) and lysed by Gaulin homogenizer. Lysate was cleared by centrifugation and loaded on a Ni-NTA and the eluate on a GST affinity column. After extensive wash, recombinant protein was cleaved by a specific protease and eluted. Recombinant PERK cytoplasmic domain obtained by this protocol was >85% pure by coomassie stained SDS-PAGE.

Biochemical Assay for Inhibitors of MPS1 and PERK Kinase Activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity.

Supernatant is subsequently withdrawn and transferred into a counting plate, then evaluated by β-counting.

Reagents/Assay Conditions
i. Dowex Resin Preparation 500 g of wet resin (SIGMA, custom prepared resin DOWEX 1×8 200-400 mesh, 2.5 Kg) are weighed out and diluted to 2 l in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00

The washed resin is stable for more than one week; the stock resin is kept at 4° C. before use.

ii. Kinase Buffer (KB)

The buffer for MPS1 assay was composed of HEPES 50 mM, at pH 7.5, with 2.5 mM $MgCl_2$, 1 mM $MnCl_2$, 1 mM DTT, 3 microM $Na_3VO_4$, 2 mM β-glycerophosphate and 0.2 mg/mL BSA.

The buffer for PERK assay was composed of HEPES 50 mM, at pH 7.5 with 3 mM $MgCl_2$, 1 mM DTT, 3 microM $Na_3VO_4$, and 0.2 mg/mL BSA iii. Assay Conditions The assay was run with a final concentration MPS1 of 5 nM, in the presence of 15 microM ATP and 1.5 nM $^{33}$P-γ-ATP; the substrate was P38-βtide, used at 200 microM.

The assay was run with a final concentration PERK of 8 nM, in the presence of 52 microM ATP and 2 nM $^{33}$P-γ-ATP; the substrate was eIF2alfa-tide, used at 300 microM.

Robotized Dowex Assay

The test mix consisted of:
1) 3× Enzyme mix (done in Kinase Buffer 3×), 5 microL/well
2) 3× substrate and ATP mix (done in ddH2O), together with $^{33}$P-γ-ATP, 5 microL/well
3) 3× test compounds (diluted into ddH2O—3% DMSO)—5 microL/well See below for compound dilution and assay scheme Compound Dilution and Assay Scheme is Defined Below:

i. Dilution of Compounds

Test compounds are received as a 1 mM solution in 100% DMSO, distributed into 96 or 384 well plates:

a) for percent inhibition studies (HTS), individual dilution plates at 1 mM are diluted at a 3× concentration (30 microM) in ddH2O (3% DMSO=final concentration) using a Beckman NX automated pipetting platform. The same instrument is used for distributing the diluted mother plates into the test plates.

b) for IC50 determination (KSS platform), 100 μl of each compound at 1 mM in 100% DMSO are transferred from the original plate into the first column of another 96 well plate (A1 to G1); well H1 is left empty for the internal standard inhibitor, usually staurosporine.

An automated station for serial dilutions (Biomek FX, Beckman) is used for producing 1:3 dilutions in 100% DMSO, from line A1 to A10, and for all the seven compounds in the column. Moreover, 4-5 copies of daughter plates are prepared by reformatting 5 microL of this first set of 100% DMSO dilution plates into 384 deep well-plates: one copy of the daughter plates with the serial dilutions of test compounds will be thaw the day of the experiments, reconstituted at a 3× concentration with water and used in the IC50 determination assays. In a standard experiment, the highest concentration (3×) of all compounds is 30 microM, while the lowest one is 1.5 nM.

Each 384 well-plate will contain reference wells (total enzyme activity vs. no enzymatic activity) for the Z' and signal to background evaluation.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×).

At the start of the run, the robot aspirates 5 microL of ATP mix, makes an air gap inside the tips (2 microL) and aspirates 5 microL of MPS1 mix or 5 microL of PERK mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

The resin suspension is very dense; in order to avoid tip clogging, wide bore tips are used to dispense it.

Another mixing cycle is performed after all the plates are stopped, this time using normal tips: the plates are then allowed to rest for about one hour in order to maximize ATP capture. At this point, 22 microL of the supernatant are transferred into 384-Optiplates (Perkin-Elmer), with 50 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for IC50 determination in the secondary assays/hit confirmation routines.

In Vitro Cell Proliferation Assay

A2780 human ovarian and MCF7 human breast cancer cells (1250 cells/well) were seeded in white 384 well-plates in complete medium (RPMI 1640 or EMEM plus 10% Fetal bovine serum) and treated with compounds dissolved in 0.1% DMSO, 24 h after seeding. The cells were incubated at 37° C. and 5% $CO_2$ and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly 25 µl/well reagent solution were added to each wells and after 5 minutes shacking microplates were red by Envision (PerkinElmer) luminometer. The luminescent signal was proportional to the number of cells present in culture.

Inhibitory activity was evaluated comparing treated versus control data using Assay Explorer (MDL) program. $IC_{50}$ was calculated using sigmoidal interpolation curve.

Given the above inhibition assays, the compounds of the formula (I) of the invention resulted to possess a good MPS1 and PERK inhibitory activity, typically with an $IC_{50}$ in the range between 0.001 and 5 microM.

Moreover, the compounds of the formula (I) of the invention show good cellular proliferation inhibitory activity, typically with an $IC_{50}$ in the range of from 0.010 to 1 µM in A2780 cells.

The following Table A reports the experimental data of some representative compounds of the invention of formula (I) being tested on the MPS1 and PERK enzymes in the specific in vitro kinase assay above described ($IC_{50}$ microM).

TABLE A

| Compound number | MPS1 $IC_{50}$ (microM) | PERK $IC_{50}$ (microM) |
|---|---|---|
| 30 | 0.68 | 0.40 |
| 55 | 3.44 | 0.51 |
| 61 | 0.36 | 0.24 |

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of the formula (I) may be used sequentially with known anticancer agents when a combination formulation is inappropriate.

The compounds of the formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of the formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of the formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

The synthetic preparation of some compounds of the formula (I) of the invention is described in the following examples.

The compounds of the present invention, as prepared according to the following examples, were also characterized by $^1$H NMR or by HPLC/MS analytical data; HPLC/MS data were collected following any one of methods 1, 2, 3 and 4.

HPLC/MS Analytic Method 1

The HPLC equipment consisted of a Waters Acquity™ UPLC system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 45° C. at a flow rate of 0.8 mL/min using a BEH C18 1.7 microm Waters Acquity UPLC (2.1×50 mm) column. Mobile phase A was formic acid 0.1% pH=3.3 buffer with acetonitrile (98:2), and mobile phase B was H$_2$O/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^-$); full scan, mass range from 100 to 800 amu was set up.

HPLC/MS Analytic Method 2

The HPLC equipment consisted of a Waters 2795 Alliance HT system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 30° C. at a flow rate of 1.0 mL/min using a C18, 3 microm Phenomenex (4.6×50 mm) column. Mobile phase A was ammonium acetate 5 mM pH=5.2 buffer with acetonitrile (95:5), and mobile phase B was H$_2$O/acetonitrile (5:95); the gradient was from 10 to 90% B in 8 minutes then ramp to 100% B in 1.0 minutes. The injection volume was 10 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^-$); full scan, mass range from 100 to 800 amu was set up.

HPLC/MS Analytic Method 3

The HPLC equipment consisted of a Waters Acquity™ UPLC system equipped with a 2996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 45° C. at a flow rate of 0.8 mL/min using a BEH C18 1.7 microm Waters Acquity UPLC (2.1×50 mm) column. Mobile phase A was ammonium hydroxide 0.05% pH=10 buffer with acetonitrile (95:5), and mobile phase B was H$_2$O/acetonitrile (5:95); the gradient was from 5 to 95% B in 2 minutes then hold 95% B 0.1 minutes. The injection volume was 2 microL. The mass spectrometer was operated in positive and in negative ion mode, the capillary voltage was set up at 3.5 KV (ES$^+$) and 28 V (ES$^-$); the source temperature was 120° C.; cone was 14 V (ES$^+$) and 2.8 KV (ES$^-$); full scan, mass range from 100 to 800 amu was set up.

HPLC/MS Analytical Method 4

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 1 mL/min using a RP18 Waters X Terra (3.0×20 mm) column. Mobile phase A was ammonium hydroxide 0.05% pH=10 buffer with acetonitrile (95:5), and Mobile phase B was H$_2$O/acetonitrile (5:95); the gradient was from 10 to 90% B in 4 minutes then hold 90% B 1 minutes. The injection volume was 10 microL. The mass spectrometer was operated in positive and in negative ion mode, the capillary voltage was set up at 2.5 KV; the source temperature was 120° C.; cone was 10 V; full scan, mass range from 100 to 800 amu was set up.

Several compounds of the invention of the formula (I), as prepared according to the following examples, were purified by preparative HPLC.

The operative conditions are defined below:

HPLC/MS Preparative Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters X Terra 10 microm (19×250 mm) column. Mobile phase A was ammonium hydroxide 0.05% pH=10 buffer with acetonitrile (95:5), and Mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.

HPLC/MS Preparative Method 2

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software.

HPLC was carried out at 25° C. at a flow rate of 20 mL/min using a RP18 Waters X Terra 10 microm (19×250 mm) column. Mobile phase A was 0.1% trifluoro acetic acid in water/acetonitrile (95:5), and mobile phase B was acetonitrile; the gradient was from 10 to 90% B in 15 minutes then hold 90% B 3 minutes. The injection volume was 10 microL.

The mass spectrometer was operated in positive and in negative ion mode, the capillary voltage was set up at 2.5 KV; the source temperature was 120° C.; cone was 10 V; full scan, mass range from 100 to 800 amu was set up.

MS Exact

Exact mass data ESI(+) were obtained on a Waters Q-T of Ultima directly connected with micro HPLC 1100 Agilent as previously described (M. Colombo, F. Riccardi-Sirtori, V. Rizzo, *Rapid Commun. Mass Spectrom.* 2004, 18, 511-517).

The examples below as well as throughout the application, the following abbreviations have the following meanings. If not defined, the terms have their generally accepted meanings.

| ABBREVIATIONS | |
|---|---|
| AcOEt | Ethyl acetate |
| AcOH | Acetic acid |
| DCM | Dichloromethane |
| DIPEA | N,N-diisopropyethylamine |
| DMF | N,N-dimethylformamide |
| DMSO | Dimethyl sulfoxide |
| EDCl | N-ethyl-N',N'-diisopropyl carbodiimide hydrochloride |
| Et$_2$O | Diethyl ether |
| EtOH | Ethanol |
| HCl | Hydrochloric acid |
| HOBt | 1H-benzotriazol-1-ol |
| HONH$_2$•H$_2$O | Hydroxylamine hydrate |
| HONH$_2$•HCl | Hydroxylamine hydrochloride |
| KOH | Potassium hydroxide |
| LiN(TMS)$_2$ | Lithium bis(trimethylsilyl)amide |
| mCPBA | m-Chloroperoxybenzoic acid |
| MeOH | Methanol |
| Na$_2$SO$_4$ | Sodium sulfate |
| NaHCO$_3$ | Sodium hydrogen carbonate |
| NaHMSD | Sodium hexamethyldisilazane |
| NaOH | Sodium hydroxide |
| Pd$_2$(dba)$_3$ | Tris(dibenzylideneacetone)dipalladium(0) |
| TBTU | O-(benzotriazol-1-yl)-N,N,N',N'-tetramethyluronium tetrafluoroborate |
| TFA | Trifluoro acetic acid |
| THF | Tetrahydrofurane |

Preparation A

Ethyl 7-oxo-4,5,6,7-tetrahydro-1,2-benzisoxazole-3-carboxylate st.A1

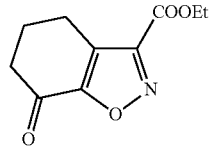

To a solution of ethyl (3-ethoxy-2-oxocyclohex-3-en-1-yl)(oxo)acetate 5.2 g (21.6 mmol) in 100 mL of EtOH, 1.5 g (21.6 mmol) of HONH$_2$.HCl was added. The mixture was stirred at 80° C. for 2 hours. After cooling the solvent was removed under reduced pressure and the crude solid was purified by flash chromatography on silica gel (eluant: DCM) to afford 1.47 g (33% yield) of the title compound as a white solid.

$^1$H NMR (DMSO-d$_6$) δ 1.34 (t, J=7.08 Hz, 3H) 2.14 (quin, J=6.29 Hz, 2H) 2.61-2.68 (m, 2H) 2.89 (m, 2H) 4.40 (q, J=7.08 Hz, 2H).

According to the same methodology, but employing suitable starting material, the following compound was prepared:

Ethyl 5,5-dimethyl-7-oxo-4,5,6,7-tetrahydro-1,2-benzisoxazole-3-carboxylate $^1$H NMR (400 MHz, DMSO-d$_6$) δ ppm 1.07 (s, 6H) 1.34 (t, J=7.14 Hz, 3H) 2.59 (s, 2H) 2.82 (s, 2H) 4.40 (q, J=7.14 Hz, 2H). [M+H]$^+$=239

Preparation B

Ethyl 7-oxo-4,5,6,7-tetrahydro-1,2-benzisoxazole-3-carboxylate and ethyl 7-oxo-4,5,6,7-tetrahydro-2,1-benzisoxazole-3-carboxylate st.A1/a Ethyl 7-ethoxy-7a-hydroxy-3a,4,5,7a-tetrahydro-1,2-benzisoxazole-3-carboxylate and ethyl 7-ethoxy-3-hydroxy-3,3a,4,5-tetrahydro-2,1-benzisoxazole-3-carboxylate

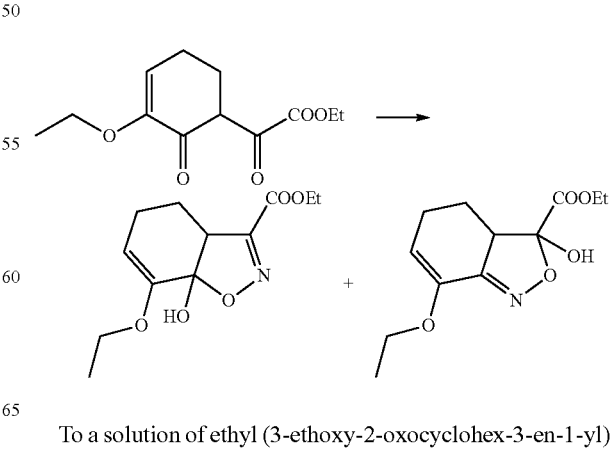

To a solution of ethyl (3-ethoxy-2-oxocyclohex-3-en-1-yl)(oxo)acetate 5.0 g (20.73 mmol) in 20 mL of EtOH and 5 mL of AcOH, 1.3 mL (20.78 mmol) of HONH$_2$.H$_2$O (50% wt/wt) was added. The mixture was stirred at room temperature for 4 hours. The solvent was removed under reduced pressure and the crude solid was purified by flash chromatography on silica gel (eluant: AcOEt/Hexane:3/7) to afford 1.35 g (25% yield) as a white solid of ethyl 7-ethoxy-7a-hydroxy-3a,4,5,7a-tetrahydro-1,2-benzisoxazole-3-carboxylate $^1$H NMR (401 MHz, DMSO-d6) δ ppm 1.24-1.32 (m, 6H) 1.87-2.37 (m, 4H) 3.11-3.20 (m, 1H) 3.64-3.75 (m, 2H) 4.22-4.36 (m, 2H) 4.86-5.08 (m, 1H) 7.26 (s, 1H);

MS calc: 256.1180. MS found: 256.1172.

And 3.18 g (60% yield) as a white solid of ethyl 7-ethoxy-3-hydroxy-3,3a,4,5-tetrahydro-2,1-benzisoxazole-3-carboxylate $^1$H NMR (401 MHz, DMSO-d6) δ ppm 1.21-1.29 (m, 6H) 1.55-1.72 (m, 1H) 1.71-1.84 (m, 1H) 2.23-2.43 (m, 2H) 3.58 (dd, J=13.67, 5.13 Hz, 1H) 3.72-3.94 (m, 2H) 4.20 (q, J=7.16 Hz, 2H) 5.44 (dd, J=6.23, 2.69 Hz, 1H) 7.66 (s, 1H);

MS calc: 256.1180. MS found: 256.1171.

According to the same methodology, but employing suitable starting material, the following compounds were prepared:

Ethyl 5,5-dimethyl-7-ethoxy-7a-hydroxy-3a,4,5,7a-tetrahydro-1,2-benzisoxazole-3-carboxylate $^1$H NMR (400 MHz, DMSO-d$_6$) δ ppm 1.03 (s, 3H) 1.04 (s, 3H) 1.08 (t, J=13.06 Hz, 1H) 1.28 (t, J=7.08 Hz, 3H) 1.89 (dd, J=13.06, 5.80 Hz, 1H) 3.34 (dd, J=13.06, 5.80 Hz, 1H) 3.50 (s, 3H) 4.23-4.33 (m, 2H) 4.76 (s, 1H) 7.39 (s, 1H).

MS calc: 270.1336. MS found: 270.1334.

Ethyl 5,5-dimethyl 7-ethoxy-3-hydroxy-3,3a,4,5-tetrahydro-2,1-benzisoxazole-3-carboxylate $^1$H NMR (400 MHz, DMSO-d$_6$) δ ppm 1.09 (s, 3H) 1.15 (s, 3H) 1.24 (t, J=7.08 Hz, 3H) 1.50-1.58 (m, 1H) 1.58-1.67 (m, 1H) 3.56 (s, 3H) 3.76 (dd, J=13.43, 5.61 Hz, 1H) 4.21 (q, J=7.08 Hz, 2H) 5.23 (s, 1H) 7.72 (s, 1H).

MS calc: 270.1336. MS found: 270.1325.

Ethyl 4,4-dimethyl-7-ethoxy-7a-hydroxy-3a,4,5,7a-tetrahydro-1,2-benzisoxazole-3-carboxylate MS calc: 270.1336. MS found: 270.1320.

Ethyl 4,4-dimethyl 7-ethoxy-3-hydroxy-3,3a,4,5-tetrahydro-2,1-benzisoxazole-3-carboxylate $^1$H NMR (400 MHz, DMSO-d$_6$) δ ppm 1.05 (s, 3H) 1.06 (s, 3H) 1.24 (t, J=7.08 Hz, 3H) 1.96 (dd, J=16.91, 6.71 Hz, 1H) 2.28 (dd, J=16.91, 2.14 Hz, 1H) 3.55 (s, 1H) 3.59 (s, 3H) 4.14-4.30 (m, 2H) 5.35 (dd, J=6.71, 2.14 Hz, 1H) 7.60 (s, 1H).

MS calc: 270.1336. MS found: 270.1329.

st.A1/b

Ethyl 7-oxo-4,5,6,7-tetrahydro-1,2-benzisoxazole-3-carboxylate

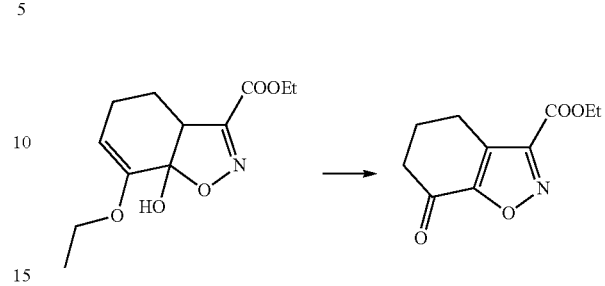

To a solution of ethyl 7-ethoxy-7a-hydroxy-3a,4,5,7a-tetrahydro-1,2-benzisoxazole-3-carboxylate 3.18 g (12.48 mmol) in 30 mL of EtOH, 3 mL of HCl 36% was added. The mixture was stirred at reflux for 48 hours. After cooling the solvent was removed under reduced pressure and the crude solid was purified by flash chromatography on silica gel (eluant: AcOEt/Hexane 3/7) to afford 1.3 g (50% yield) of the title compound as a white solid.

$^1$H NMR (DMSO-d$_6$) δ 1.34 (t, J=7.08 Hz, 3H) 2.14 (quin, J=6.29 Hz, 2H) 2.61-2.68 (m, 2H) 2.89 (t, J=6.10 Hz, 2H) 4.40 (q, J=7.16 Hz, 2H).

According to the same methodology, but employing suitable starting material, the following compounds were prepared:

Ethyl 5,5-dimethyl-7-oxo-4,5,6,7-tetrahydro-1,2-benzisoxazole-3-carboxylate $^1$H NMR (400 MHz, DMSO-d6) δ ppm 1.07 (s, 6H) 1.34 (t, J=7.14 Hz, 3H) 2.59 (s, 2H) 2.82 (s, 2H) 4.40 (q, J=7.14 Hz, 2H).

[M+H]$^+$=239

Ethyl 4,4-dimethyl-7-oxo-4,5,6,7-tetra hydro-1,2-benzisoxazole-3-carboxylate

[M+H]$^+$=239 st.A1/b

Ethyl 7-oxo-4,5,6,7-tetrahydro-2,1-benzisoxazole-3-carboxylate

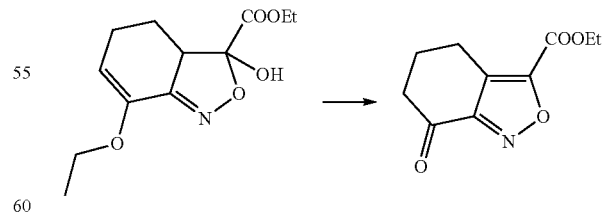

To a solution of ethyl 7-ethoxy-3-hydroxy-3,3a,4,5-tetrahydro-2,1-benzisoxazole-3-carboxylate 1.35 g (5.29 mmol) in 10 mL of EtOH, 1 mL of HCl 36% was added. The mixture was stirred at reflux for 2 hours. After cooling the solvent was removed under reduced pressure and the crude solid was purified by flash chromatography on silica gel (eluant: AcOEt/Hexane 2/8) to afford 0.380 g (35% yield) of the title compound as a white solid.

¹H NMR (401 MHz, DMSO-d6) δ ppm 1.34 (t, J=7.08 Hz, 3H) 2.09 (quin, J=6.32 Hz, 2H) 2.67-2.73 (m, 2H) 2.93 (t, J=6.32 Hz, 2H) 4.40 (q, J=7.08 Hz, 2H).

According to the same methodology, but employing suitable starting material, the following compounds were prepared:

Ethyl 5,5-dimethyl-7-oxo-4,5,6,7-tetrahydro-2,1-benzisoxazole-3-carboxylate

¹H NMR (401 MHz, DMSO-d₆) δ ppm 1.03 (s, 6H) 1.35 (t, J=7.14 Hz, 3H) 2.64 (s, 2H) 2.86 (s, 2H) 4.40 (q, J=7.14 Hz, 2H).

MS calc: 238.1074. MS found: 238.1071.

Ethyl 4,4-dimethyl-7-oxo-4,5,6,7-tetrahydro-2,1-benzisoxazole-3-carboxylate

¹H NMR (400 MHz, DMSO-d6) d ppm 1.27 (s, 6H) 1.38 (t, J=7.14 Hz, 3H) 1.62-1.71 (m, 2H) 2.71-6.78 m, 2H) 4.41 (q, J=7.14 Hz, 2H).

[M+H]⁺=239

Preparation C

Ethyl 6-[(dimethylamino)methylidene]-7-oxo-4,5,6,7-tetrahydro-1,2-benzisoxazole-3-carboxylate st.A2

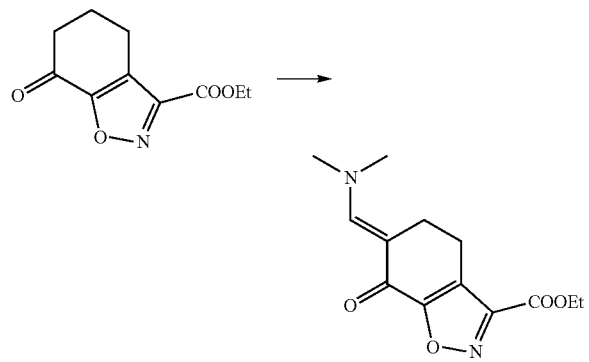

To a solution of ethyl 7-oxo-4,5,6,7-tetrahydro-1,2-benzisoxazole-3-carboxylate 1.47 g (7.0 mmol) in 15 mL of toluene, 1.45 mL (8.44 mmol, d 0.859) of N,N-dimethylformamide diethyl acetal was added. The mixture was stirred at 90° C. for 3 hours. After cooling the solvent was removed under reduced pressure and the crude solid was purified by flash chromatography on silica gel (eluant: AcOEt) to afford 1.41 g (76% yield) of the title compound.

¹H NMR (401 MHz, DMSO-d6) δ ppm 1.33 (t, J=7.08 Hz, 3H) 2.80 (t, J=7.08 Hz 2H) 2.99 (t, J=7.02 Hz 2H) 3.16 (s, 6H) 4.38 (q, J=7.08 Hz, 2H) 7.56 (s, 1H);

MS calc: 265.1183. MS found: 265.1183.

According to the same methodology, but employing suitable starting material, the following compounds were prepared:

Ethyl 5,5-dimethyl-6-[(dimethylamino)methylidene]-7-oxo-4,5,6,7-tetrahydro-2,1-benzisoxazole-3-carboxylate

[M+H]⁺=293

Ethyl-6-[(dimethylamino)methylidene]-4,4-dimethyl-7-oxo-4,5,6,7-tetrahydro-2,1-benzisoxazole-3-carboxylate ¹H NMR (400 MHz, DMSO-d₆) δ ppm 1.34 (t, J=7.08 Hz, 3H) 1.37 (s, 6H) 2.80 (s, 2H) 3.18 (s, 6H) 4.39 (q, J=7.08 Hz, 2H) 7.70 (s, 1H).

MS calc: 293.1496. MS found: 293.1495.

Preparation D

Ethyl 6-[(dimethylamino)methylidene]-7-oxo-4,5,6,7-tetrahydro-2,1-benzisoxazole-3-carboxylate st.A2

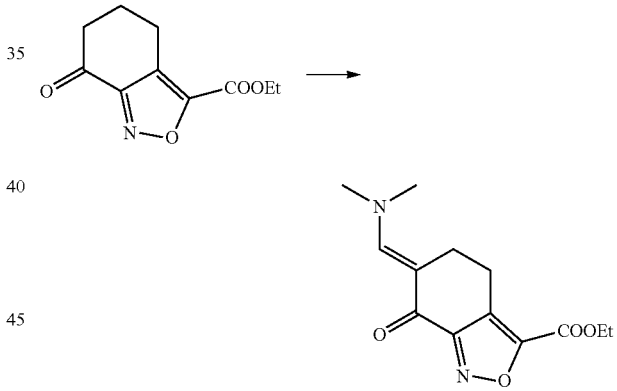

To a solution of ethyl 7-oxo-4,5,6,7-tetrahydro-2,1-benzisoxazole-3-carboxylate 1.20 g (5.7 mmol) in 20 mL of toluene, 1.45 mL (8.44 mmol, d 0.859) of N,N-dimethylformamide diethyl acetal was added. The mixture was stirred at 90° C. for 4 hours. After cooling the solvent was removed under reduced pressure and the crude solid was purified by flash chromatography on silica gel (eluant: AcOEt) to afford 0.90 g (60% yield) of the title compound.

¹H NMR (401 MHz, DMSO-d6) δ ppm 1.33 (t, J=7.08 Hz, 3H) 2.79-2.96 (m, 4H) 3.18 (s, 6H) 4.37 (q, J=7.08 Hz, 2H) 7.69 (s, 1H);

MS calc: 265.1183. MS found: 265.1177.

According to the same methodology, but employing suitable starting material, the following compounds were prepared:

Ethyl 5,5-dimethyl-6-[(dimethylamino)methylidene]-7-oxo-4,5,6,7-tetrahydro-1,2-benzisoxazole-3-carboxylate MS calc: 293.1496. MS found: 293.1488.

Ethyl-6-[(dimethylamino)methylidene]-4,4-dimethyl-7-oxo-4,5,6,7-tetrahydro-1,21-benzisoxazole-3-carboxylate

M+H]$^+$=293

Preparation E 1-(4-bromo-2-methoxyphenyl)guanidine

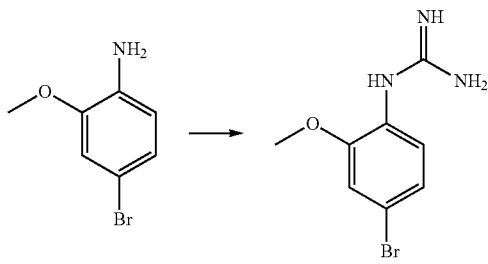

To a solution of 4-bromo-2-methoxyaniline 7.1 g (35.1 mmol) in HCl 25% m/v 20 mL, cyanamide 20.6 g (494.3 mmol) was added in portion (1.6 g every half hour). The reaction was stirred at 60° C. for 6 hours, then cooled down to room temperature, diluted with H$_2$O (20 mL), extracted with AcOEt (10 mL). NaOH 35% (30 mL) was added to pH>>14. The aqueous phase was extracted with AcOEt (3×50 mL), dried over Na$_2$SO$_4$ and concentrated to afford 8.5 g (quantitative yield) of the title compound.

$^1$H NMR (DMSO-d$_6$) δ ppm 3.70 (s, 3H) 5.21 (br. s., 4H) 6.71 (d, J=8.30 Hz, 1H) 6.93 (dd, J=8.30, 2.20 Hz, 1H) 7.00 (d, J=2.20 Hz, 1H);

MS calc: 244.0080. MS found: 244.0077.

Preparation F 4-(4-Methyl-piperazin-1-yl)-2-trifluoromethoxy-phenylamine

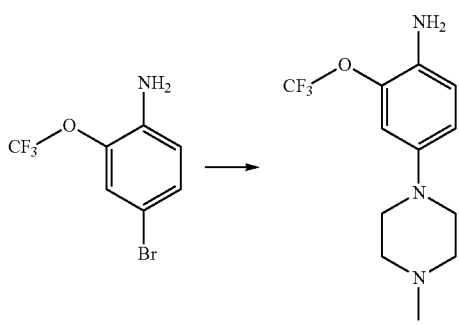 [SMILES: Nc1ccc(Br)cc1OC(F)(F)F ; CN1CCN(c2ccc(N)c(OC(F)(F)F)c2)CC1]

Pd$_2$(dba)$_3$ (1.1 g, 1.2 mmol), 2-dicyclohexylphosphino-2'-(N,N-dimethylamino)-biphenyl (0.94 g, 2.4 mmol), 5-bromo-2-trifluoromethoxy-phenylamine (30.7 g, 120 mmol) in THF (50 mL) were charged in a round-bottom flask flushed with argon. The flask was evacuated and backfilled with argon. LiN(TMS)$_2$ solution (1M in THF, 288 mL) and N-methylpiperazine (26.7 mL, 194 mmol) were added and the reaction refluxed for 1 hours. The reaction mixture was then allowed to cool to room temperature and filtered through a pad of celite. The organic phase was concentrated, the residue dissolved in DCM (200 mL) and washed with H$_2$O (1×100 mL). The organic phases were dried over anhydrous Na$_2$SO$_4$, the solvent evaporated in vacuo and the crude solid was purified by flash chromatography on silica gel (eluant: DCM/EtOH 90/10) to afford 23 g of 4-(4-methyl-piperazin-1-yl)-2-trifluoromethoxy-phenylamine (70% yield) as a light brown powder.

$^1$H NMR (401 MHz, DMSO-d6) δ ppm 2.22 (s, 3H), 2.44 (t, J=4.88 Hz, 4H), 2.94 (t, J=4.88 Hz, 4H) 4.77 (br.s., 2H) 6.66-6.69 (m, 1H) 6.73-6.80 (m, 2H);

MS calc: 276.1318. MS found: 276.1320.

According to this same methodology, but employing suitable substituted derivatives, the following compound was prepared:

4-(4-Methyl-piperazin-1-yl)-2-methoxy-phenylamine $^1$H NMR (400 MHz, DMSO-d6) δ ppm 2.83 (s., 3H) 3.05-3.19 (m, 4H) 3.46 (m., 4H) 3.91 (s, 3H) 6.62 (dd, J=8.54, 2.32 Hz, 1H) 6.80 (d, J=2.32 Hz, 1H) 7.27 (d, J=8.54 Hz, 1H) 9.77 (br. s., 2H);

MS calc: 222.1601. MS found: 222.1596.

Preparation G

N-[4-(4-Methyl-piperazin-1-yl)-2-trifluoromethoxy-phenyl]-guanidine

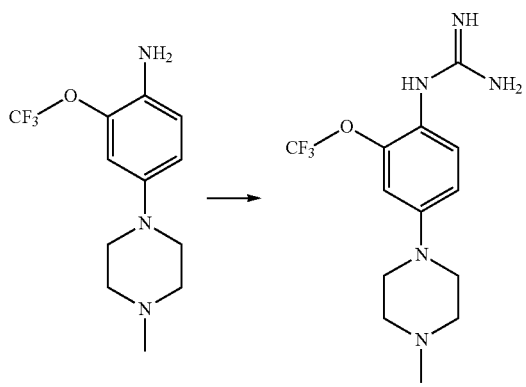 [SMILES: CN1CCN(c2ccc(N)c(OC(F)(F)F)c2)CC1 ; CN1CCN(c2ccc(NC(=N)N)c(OC(F)(F)F)c2)CC1]

To a solution of 4-(4-methyl-piperazin-1-yl)-2-trifluoromethoxy-phenylamine (275 mg, 1 mmol) in HCl 6N (1 mL), cyanamide (336 mg, 8.0 mmol) was added and the reaction was stirred at 60° C. for 1 hours. The mixture was cooled down to room temperature, diluted with H$_2$O (3 mL), extracted with DCM (10 mL). NaOH 2N was added to pH>11. The aqueous phase was extracted with Et$_2$O (3×10 mL), dried over Na$_2$SO$_4$ and concentrated. The residue was crystallized from Et$_2$O to give the title compound (240 mg, 76% yield) as a white solid.

$^1$H NMR (401 MHz, DMSO-d6) δ ppm 2.21 (s, 3H) 2.43 (t, J=4.55 Hz, 4H) 3.02 (t, J=4.55 Hz, 4H) 5.07 (br. s., 4H) 6.65-6.75 (m, 1H) 6.75-6.87 (m, 2H);

MS calc: 318.1536. MS found: 318.1526.

According to this same methodology, but employing suitable substituted derivatives, the following compounds were prepared:

N-[4-(4-Methyl-piperazin-1-yl)-2-methoxy-phenyl]-guanidine

¹H NMR (401 MHz, DMSO-d6) δ ppm 2.21 (s, 3H) 2.44 (t, J=4.50 Hz, 4H) 3.04 (t, J=4.50 Hz, 4H) 3.68 (s, 3H) 4.77-5.57 (br.s., 4H) 6.38 (dd, J=6.59, 2.44 Hz, 1H) 6.51 (d, J=2.44 Hz, 1H) 6.66 (d, J=6.59 Hz, 1H);
MS calc: 264.1819. MS found: 264.1817.

N-[4-(tert-butylcarboxamido)-2-methoxy-phenyl]-guanidine

¹H NMR (401 MHz, DMSO-d₆) δ ppm 1.53 (s, 9H) 3.73 (s, 3H) 5.20 (br. s., 4H) 6.75-6.90 (m, 1H) 7.34 (d, J=1.89 Hz, 1H) 7.38 (dd, J=8.11, 1.89 Hz, 1H);
MS calc: 266.1499. MS found: 266.1491.

Example 1

Ethyl 8-[(4-bromo-2-methoxyphenyl)amino]-4,5-dihydroisoxazolo[4,5-h]quinazoline-3-carboxylate st.A3

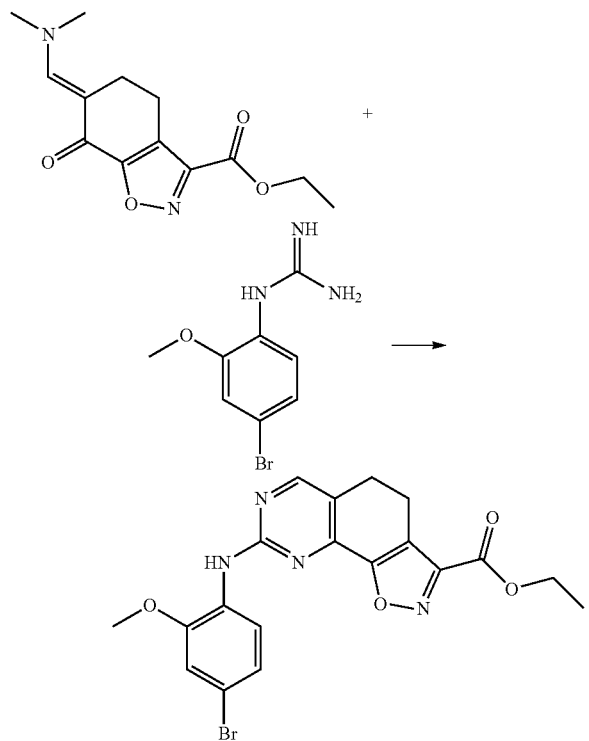

A solution of ethyl-6-[(dimethylamino)methylidene]-7-oxo-4,5,6,7-tetrahydro-1,2-benzisoxazole-3-carboxylate 0.5 g (1.89 mmol) and 1-(4-bromo-2-methoxyphenyl)guanidine 0.6 g (2.46 mmol) in 8 mL of EtOH was stirred at 80° C. for 4 hours. After cooling the yellow precipitate formed during the reaction was collected by filtration, washed with cold EtOH and dried, to give 0.603 g (71% yield) of the title compound.

¹H NMR (DMSO-d₆) δ 1.35 (t, J=7.14 Hz, 3H) 2.93-3.04 (m, 4H) 3.87 (s, 3H) 4.40 (q, J=7.14 Hz, 2H) 7.17 (dd, J=8.54, 2.20 Hz, 1H) 7.24 (d, J=2.20 Hz, 1H) 8.05 (d, J=8.54 Hz, 1H) 8.36 (s, 1H) 8.51 (s, 1H);
MS calc: 445.0506. MS found: 445.0504.

According to this same methodology, but employing suitable substituted derivatives, the following compounds were prepared:

Ethyl 8-{[4-(tert-butoxycarbonyl)-2-methoxyphenyl]amino}-4,5-dihydroisoxazolo[4,5-h]quinazoline-3-carboxylate ¹H NMR (401 MHz, DMSO-d6) δ ppm 1.36 (t, J=7.16 Hz, 3H) 1.56 (s, 9H) 3.00-3.04 (m, 4H) 3.94 (s, 3H) 4.41 (q, J=7.16 Hz, 2H) 7.49 (d, J=1.83 Hz, 1H) 7.60 (dd, J=8.54, 1.83 Hz, 1H) 8.43 (d, J=8.54 Hz, 1H) 8.44 (s, 1H) 8.60 (s, 1H)
MS calc: 467.1925. MS found: 467.1902.

Ethyl 8-{[4-(4-methylpiperazin-1-yl)-2-(trifluoromethoxy)phenyl]amino}-4,5-dihydroisoxazolo[4,5-h]quinazoline-3-carboxylate ¹H NMR (401 MHz, DMSO-d6) δ ppm 1.34 (t, J=7.14 Hz, 3H) 2.24 (s, 3H) 2.45-2.48 (m, 4H) 2.86-3.02 (m, 4H) 3.13-3.21 (m, 4H) 4.40 (q, J=7.14 Hz, 2H) 6.84-6.89 (m, 1H) 6.97 (dd, J=8.91, 2.69 Hz, 1H) 7.46 (d, J=8.91 Hz, 1H) 8.37 (s, 1H) 9.03 (s, 1H)
MS calc: 519.1962. MS found: 519.1962.

Ethyl 8-{[2-methoxy-4-(4-methylpiperazin-1-yl)phenyl]amino}-4,5-dihydroisoxazolo[4,5-h]quinazoline-3-carboxylate Ethyl 8-{[4-(4-methylpiperazin-1-yl)phenyl]amino}-4,5-dihydroisoxazolo[4,5-h]quinazoline-3-carboxylate Ethyl 5,5-dimethyl-8-{[4-(4-methylpiperazin-1-yl)phenyl]amino}-4,5-dihydroisoxazolo[4,5-h]quinazoline-3-carboxylate MS calc: 463.2452. MS found: 463.2472.

Ethyl 8-({2-methoxy-4-[(1-methylpiperidin-4-yl)carbamoyl]phenyl}amino)-5,5-dimethyl-4,5-dihydroisoxazolo[4,5-h]quinazoline-3-carboxylate ¹H NMR (400 MHz, DMSO-d₆) δ ppm 1.36 (t, J=7.16 Hz, 3H) 1.37 (s, 6H),1.59-1.73 (m, 2H) 1.80-1.89 (m, 2H) 2.30-2.41 (m, 5H) 2.95 (s, 2H) 2.96-3.04 (m, 1H), 3.82 (br. s., 1H) 3.93-3.95 (m, 3H) 4.41 (q, J=7.16 Hz, 2H) 7.51 (d, J=1.71 Hz, 1H) 7.56 (dd, J=8.42, 1.71 Hz, 1H) 8.17 (d, J=7.57 Hz, 1H) 8.36 (d, J=8.42 Hz, 1H) 8.42 (s, 1H) 8.69 (s, 1H).).
MS calc: 535.2664. MS found: 535.2669.

Example 2

8-[(4-bromo-2-methoxyphenyl)amino]-N-(2,6-diethylphenyl)-4,5-dihydroisoxazolo[4,5-h]quinazoline-3-carboxamide Conv.c

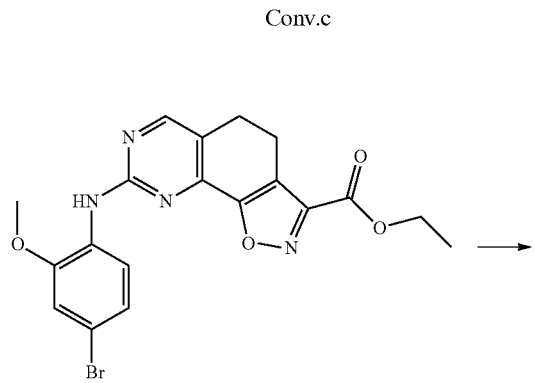

To a solution of ethyl 8-[(4-bromo-2-methoxyphenyl)amino]-4,5-dihydroisoxazolo[4,5-h]quinazoline-3-carboxylate 250 mg (0.562 mmol) and 2,6-diethylaniline 0.14 mL (0.843 mmol d 0.906) in 4 mL of anhydrous THF, 1.68 mL of NaHMDS solution (1.0 M in THF, 1.68 mmol) were added dropwise. The mixture was stirred at room temperature for 1 hours. H$_2$O was added and the mixture was extracted twice with DCM. The organic layer was dried over Na$_2$SO$_4$ and the solvent evaporated to dryness. The crude solid was purified by flash chromatography on silica gel (AcOEt/Hexane) to afford 190 mg (62% yield) of the title compound.

$^1$H NMR (DMSO-d6) δ 1.13 (t, J=7.57 Hz, 6H) 2.57 (q, J=7.57 Hz, 4H) 2.97-3.01 (m, 4H), 3.89 (s, 3H), 7.07-7.22 (m, 3H), 7.22-7.31 (m, 2H), 8.07 (d, J=8.67 Hz, 1H), 8.38 (s, 1H), 8.51 (s, 1H), 10.30 (s, 1H);

MS calc: 548.1292. MS found: 548.1299.

According to this same methodology, but employing suitable substituted derivatives, the following compound was prepared:

N-(2,6-diethylphenyl)-8-{[4-(4-methylpiperazin-1-yl)-2-(trifluoromethoxy)phenyl]amino}-4,5-dihydroisoxazolo[4,5-h]quinazoline-3-carboxamide $^1$H NMR (401 MHz, DMSO-d6) δ ppm 1.13 (t, J=7.57 Hz, 6H) 2.24 (s, 3H) 2.43-2.50 (m, 4H) 2.56 (q, J=7.57 Hz, 4H) 2.91-2.99 (m, 4H) 3.13-3.20 (m, 4H) 6.85-6.89 (m, 1H) 6.97 (dd, J=8.91, 2.75 Hz, 1H) 7.10-7.19 (m, 2H) 7.21-7.28 (m, 1H) 7.47 (d, J=8.91 Hz, 1H) 8.37 (s, 1H) 9.06 (s, 1H) 10.28 (s, 1H)

MS calc: 622.2748. MS found: 622.2757.

Example 3

N-(2,6-diethylphenyl)-8-({4-[4-(dimethylamino)piperidin-1-yl]-2-methoxyphenyl}amino)-4,5-dihydroisoxazolo[4,5-h]quinazoline-3-carboxamide Conv.d

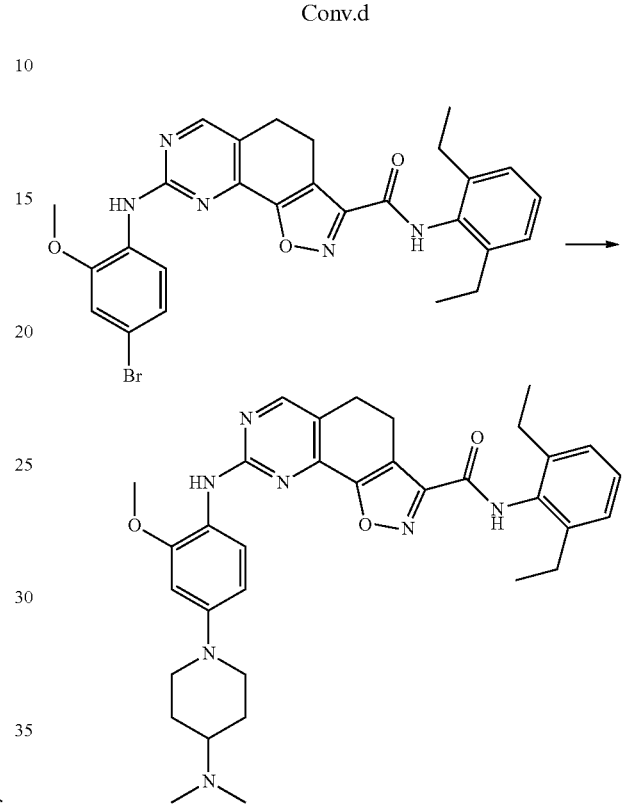

Pd$_2$(dba)$_3$, 1.7 mg (0.0018 mmol), 2-dicyclohexylphosphino-2'-(N,N-dimethylamino)-biphenyl 1.4 mg, (0.0036 mmol), 8-[(4-bromo-2-methoxyphenyl)amino]-N-(2,6-diethylphenyl)-4,5-dihydroisoxazolo[4,5-h]quinazoline-3-carboxamide 50 mg (0.091 mmol), 4-dimethylamine-piperidine 35 mg (1.3 mmol), in THF (0.5 mL) were charged in a round-bottom flask flushed with argon. The flask was evacuated and backfilled with argon. LiN(TMS)$_2$ solution (1M in THF, 0.73 mL) was added and the reaction mixture refluxed for 1 hours. The reaction mixture was then allowed to cool to room temperature. H$_2$O was added, and the mixture was extracted twice with DCM. The organic layer was dried over Na$_2$SO$_4$ and the solvent was evaporated to dryness. The crude solid was purified by flash chromatography on silica gel (eluant DCM/MeOH/(NH$_3$ 7 N in MeOH) 85/15/0.2) to afford 31 mg (57% yield) of the title compound.

$^1$H NMR (401 MHz, DMSO-d6) δ ppm 1.13 (t, J=7.57 Hz, 6H) 1.43-1.57 (m, 2H) 1.79-1.89 (m, 2H) 2.16-2.19 (m, 1H) 2.20 (s, 6H) 2.57 (q, J=7.57 Hz, 4H) 2.62-2.71 (m, 2H) 2.90-3.01 (m, 4H) 3.65-3.73 (m, 2H) 3.80 (s, 3H) 6.51 (dd, J=8.79, 2.45 Hz, 1H) 6.64 (d, J=2.45 Hz, 1H) 7.16 (d, J=7.60 Hz, 2H) 7.25 (t, J=7.60 Hz, 1H) 7.64 (d, J=8.79 Hz, 1H) 8.21 (s, 1H) 8.39 (s, 1H) 10.29 (s, 1H)

MS calc: 596.3344. MS found: 596.3332.

According to this same methodology, but employing suitable substituted derivatives, the following compounds were prepared:

N-(2,6-diethylphenyl)-8-{[2-methoxy-4-(4-pyrrolidin-1-ylpiperidin-1-yl)phenyl]amino}-4,5-dihydroisoxazolo[4,5-h]quinazoline-3-carboxamide $^1$H NMR (401 MHz, DMSO-d6) δ ppm 1.13 (t, J=7.57 Hz, 6H) 1.46-1.61 (m, 2H) 1.65-1.75 (m, 4H) 1.88-1.99 (m, 2H) 2.57 (q, J=7.57 Hz, 4H) 2.68-2.78 (m, 2H) 2.90-3.02 (m, 4H) 3.57-3.66 (m, 2H) 3.80 (s, 3H) 6.52 (dd, J=8.79, 2.44 Hz, 1H) 6.64 (d, J=2.44 Hz, 1H) 7.16 (d, J=7.60 Hz, 2H) 7.25 (t, J=7.60 Hz, 1H) 7.66 (d, J=8.79 Hz, 1H) 8.21 (s, 1H) 8.39 (s, 1H) 10.29 (s, 1H)

MS calc: 622.35. MS found: 622.3499.

N-(2,6-diethylphenyl)-8-({4-[4-(2-hydroxyethyl)piperazin-1-yl]-2-methoxyphenyl}amino)-4,5-dihydroisoxazolo[4,5-h]quinazoline-3-carboxamide $^1$H NMR (401 MHz, DMSO-d6) δ ppm 1.13 (t, J=7.57 Hz, 6H) 2.45 (t, J=6.23 Hz, 2H) 2.5-2.62 (m, 8H) 2.87-3.04 (m, 4H) 3.06-3.19 (m, 4H) 3.50-3.58 (m, 2H) 3.81 (s, 3H) 4.41 (t, J=5.37 Hz, 1H) 6.51 (dd, J=8.79, 2.44 Hz, 1H) 6.64 (d, J=2.44 Hz, 1H) 7.16 (d, J=7.60 Hz, 2H) 7.25 (t, J=7.60 Hz, 1H) 7.65 (d, J=8.79 Hz, 1H) 8.22 (s, 1H) 8.39 (s, 1H) 10.29 (s, 1H)

MS calc: 598.3137. MS found: 598.3128.

N-(2,6-diethylphenyl)-8-{[2-methoxy-4-(4-methylpiperazin-1-yl)phenyl]amino}-4,5-dihydroisoxazolo[4,5-h]quinazoline-3-carboxamide $^1$H NMR (401 MHz, DMSO-d6) δ ppm 1.13 (t, J=7.57 Hz, 6H) 2.25 (s, 3H) 2.46-2.51 (m, 4H) 2.56 (q, J=7.57 Hz, 3H) 2.85-3.01 (m, 4H) 3.09-3.19 (m, 4H) 3.81 (s, 3H) 6.51 (dd, J=8.67, 2.56 Hz, 1H) 6.64 (d, J=2.56 Hz, 1H) 7.05-7.21 (m, 1H) 7.20-7.37 (m, 1H) 7.65 (d, J=8.67 Hz, 1H) 8.22 (s, 1H) 8.39 (s, 1H) 10.29 (s, 1H)

MS calc.: 568.3031. MS found: 568.3027.

Example 4

4-{[3-(ethoxycarbonyl)-4,5-dihydroisoxazolo[4,5-h]quinazolin-8-yl]amino}-3-methoxybenzoic acid Conv.e

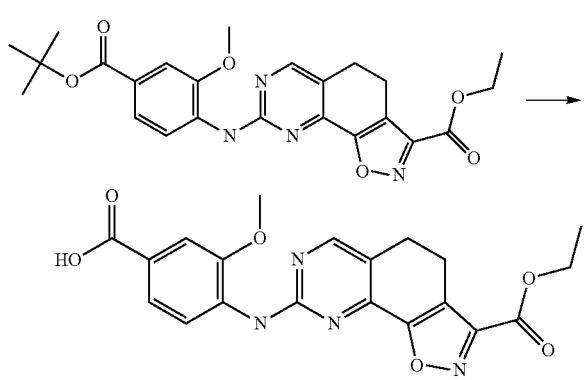

To a solution of ethyl 8-{[4-(tert-butoxycarbonyl)-2-methoxyphenyl]amino}-4,5-dihydroisoxazolo[4,5-h]quinazoline-3-carboxylate (45 mg, 0.0965 mmol) in DCM (0.4 mL), TFA (0.4 mL) was added. The mixture was stirred at room temperature for 2 hours. The organic solvent was evaporated to dryness to give the title compound in quantitative yield.

$^1$H NMR (401 MHz, DMSO-d6) δ ppm 1.36 (t, J=7.14 Hz, 3H) 2.99-3.05 (m, 4H) 3.95 (s, 3H) 4.41 (q, J=7.14 Hz, 2H) 7.54 (d, J=1.71 Hz, 1H) 7.63 (dd, J=8.54, 1.71 Hz, 1H) 8.44 (s, 1H) 8.43 (d, J=8.54 Hz, 1H) 8.60 (s, 1H)

MS calc: 411.1299. MS found: 411.13.

Example 5

N-(2,6-diethylphenyl)-8-[(4-{[4-(dimethylamino)piperidin-1-yl]carbonyl}-2-methoxyphenyl)amino]-4,5-dihydroisoxazolo[4,5-h]quinazoline-3-carboxamide Conv.f

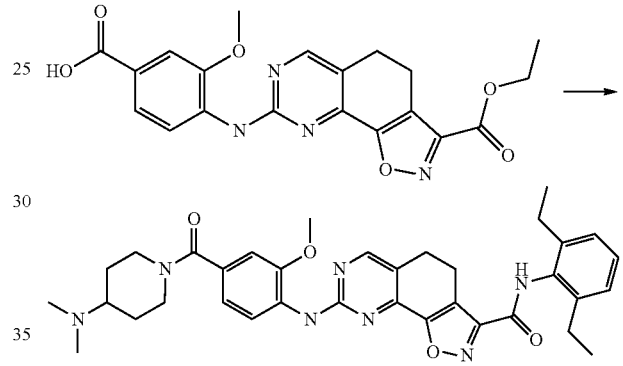

A solution of 4-{[3-(ethoxycarbonyl)-4,5-dihydroisoxazolo[4,5-h]quinazolin-8-yl]amino}-3-methoxybenzoic acid (38 mg, 0.093 mmol) in anhydrous DMF (0.5 mL) was treated with DIPEA (0.150 mL) and TBTU (45 mg, 0.139 mmol). The mixture was then treated with 4-dimethylamine-piperidine (014 mg, 0.111 mmol). The reaction was stirred at room temperature for 1 hours. The reaction was diluted with H$_2$O and extracted twice with DCM. The organic layer was dried over Na$_2$SO$_4$ and the solvent was evaporated to dryness. The residue was dissolved in 0.5 mL of anhydrous THF and 2,6-diethylaniline 0.021 mL (0.127 mmol) was added. Then NaHMDS solution, 0.25 mL (1.0 M in THF, 0.25 mmol), was added dropwise. The mixture was stirred at room temperature for 1 hours. Water was added and the mixture was extracted twice with DCM. The organic layer was dried over Na$_2$SO$_4$ and the solvent evaporated to dryness. The crude solid was purified by flash chromatography on silica gel (DCM/MeOH) to afford 23 mg (40% yield) of the title compound.

$^1$H NMR (401 MHz, DMSO-d6) δ ppm 1.14 (t, J=7.49 Hz, 6H) 1.30-1.46 (m, 2H) 1.71-1.86 (m, 2H) 2.23 (br. s., 6H) 2.57 (q, J=7.49 Hz, 4H) 2.86-2.98 (m, 1H) 2.96-3.08 (m, 4H) 3.69-3.86 (m, 4H) 3.91 (s, 3H) 7.03 (dd, J=8.18, 1.71 Hz, 1H) 7.07 (d, J=1.71 Hz, 1H) 7.16 (d, J=7.60 Hz, 2H) 7.26 (t, J=7.60 Hz, 1H) 8.26 (d, J=8.18 Hz, 1H) 8.39 (s, 1H) 8.55 (s, 1H) 10.31 (s, 1H)

MS calc: 624.3293. MS found: 624.3284.

Example 6

8-{[4-(4-methylpiperazin-1-yl)-2-(trifluoromethoxy)phenyl]amino}-4,5-dihydroisoxazolo[4,5-h]quinazoline-3-carboxamide Conv.b

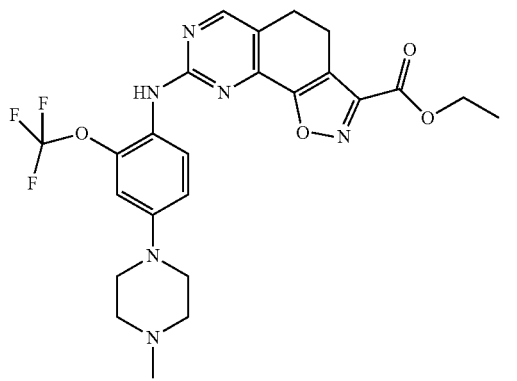

To a mixture of ethyl 8-{[4-(4-methylpiperazin-1-yl)-2-(trifluoromethoxy)phenyl]amino}-4,5-dihydroisoxazolo[4,5-h]quinazoline-3-carboxylate 15 mg (0.029 mmol) in MeOH, NH₃ solution (0.5 mL, 7N in MeOH) was added. The reaction was stirred for 20 minutes and then the solvent was evaporated to dryness, to give the title compound in quantitative yield.

$^1$H NMR (401 MHz, DMSO-d6) δ ppm 2.26 (s, 3H) 2.45-2.52 (m, 4H) 2.87-2.99 (m, 4H) 3.14-3.23 (m., 4H) 6.87 (d, J=2.75 Hz, 1H) 6.97 (dd, J=8.91, 2.75 Hz, 1H) 7.47 (d, J=8.91 Hz, 1H) 7.89 (br.s., 1H) 8.19 (br.s., 1H) 8.36 (s, 1H) 9.01 (s, 1H)

MS calc: 490.1809. MS found: 490.1812.

According to this same methodology, but employing suitable substituted derivatives, the following compounds were prepared:

8-{[4-(4-methylpiperazin-1-yl)phenyl]amino}-4,5-dihydroisoxazolo[4,5-h]quinazoline-3-carboxamide $^1$H NMR (401 MHz, DMSO-d6) δ ppm 2.27 (s, 3H) 2.54-2.63 (m, 4H), 2.90-3.01 (m, 4H) 3.03-3.13 (m, 4H) 6.84-6.94 (m, 2H) 7.57-7.63 (m, 2H) 7.90 (br.s., 1H) 8.19 (br.s., 1H) 8.44 (s, 1H) 9.55 (s, 1H)

MS calc: 406.1986. MS found: 406.1988.

8-({2-methoxy-4-[(1-methylpiperidin-4-yl)carbamoyl]phenyl}amino)-5,5-dimethyl-4,5-dihydroisoxazolo[4,5-h]quinazoline-3-carboxamide $^1$H NMR (400 MHz, DMSO-d₆) δ ppm 1.35 (s, 6H) 1.59-1.72 (m, 2H) 1.81 (m, 2H) 2.22-2.38 (m, 5H) 2.85-2.92 (m, 2H) 2.94 (s, 2H) 3.81 (m, 1H) 3.95 (s, 3H) 7.51 (d, J=1.71 Hz, 1H) 7.55 (dd, J=8.30, 1.71 Hz, 1H) 7.94 (br.s., 1H) 8.16 (m, 1H) 8.22 (br.s., 1H) 8.36 (d, J=8.30 Hz, 1H) 8.38 (s, 1H) 8.67 (s, 1H).

MS calc: 506.2511. MS found: 506.2516.

5,5-dimethyl-8-{[4-(4-methylpiperazin-1-yl)phenyl]amino}-4,5-dihydroisoxazolo[4,5-h]quinazoline-3-carboxamide $^1$H NMR (400 MHz, DMSO-d₆) δ ppm 1.32 (s, 6H) 2.23 (s, 3H) 2.45-2.49 (m, 4H) 2.91 (s, 2H) 3.02-3.10 (m, 4H) 6.83-6.96 (m, 2H) 7.57-7.65 (m, 2H) 7.92 (s, 1H) 8.19 (s, 1H) 8.55 (s, 1H) 9.60 (s, 1H).

MS calc: 434.2299. MS found: 434.2306.

5,5-dimethyl-8-{[4-(4-methylpiperazin-1-yl)-2-(trifluoromethoxy)phenyl]amino}-4,5-dihydroisoxazolo[4,5-h]quinazoline-3-carboxamide $^1$H NMR (400 MHz, DMSO-d₆) δ ppm 1.30 (s, 6H) 2.25 (s, 3H) 2.90 (s, 2H) 3.09-3.21 (m, 4H) 6.86 (s, 1H) 6.96 (dd, J=9.15, 2.69 Hz, 1H) 7.40-7.52 (m, 1H) 7.91 (s, 1H) 8.19 (s, 1H) 8.48 (s, 1H) 9.06 (s, 1H).

MS calc: 518.2122. MS found: 518.2116.

Example 7

8-({2-methoxy-4-[(1-methylpiperidin-4-yl)carbamoyl]phenyl}amino)-5,5-dimethyl-4,5-dihydroisoxazolo[4,5-h]quinazoline-3-carboxylic acid Conv.a

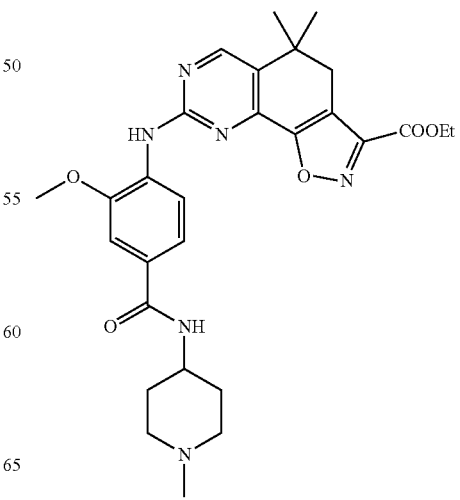

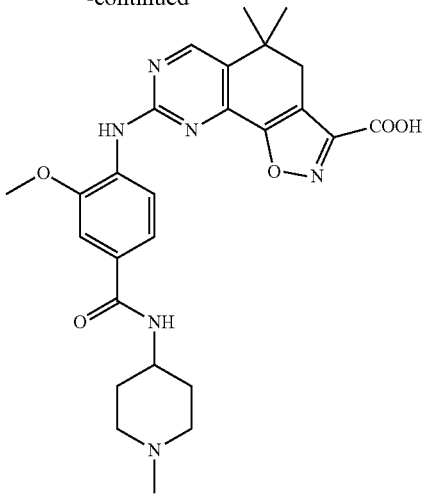

Ethyl 8-({2-methoxy-4-[(1-methylpiperidin-4-yl)carbamoyl]phenyl}amino)-5,5-dimethyl-4,5-dihydroisoxazolo[4,5-h]quinazoline-3-carboxylate (520 mg, 1 mmol) was suspended in EtOH (2 mL) and treated with a 1.5 M solution of KOH (2 mL, 3 eq.) at room temperature for 1 hour. Solvent was evaporated to dryness to yield the title compound as potassium salt that was used as such in the next step.

According to this same methodology, but employing suitable substituted derivatives, the following compound was prepared:

5,5-dimethyl-8-{[4-(4-methylpiperazin-1-yl)phenyl]amino}-4,5-dihydroisoxazolo[4,5-h]quinazoline-3-carboxylic acid Example 8

N-[(1S)-2-(1,3-dioxo-1,3-dihydro-2H-isoindol-2-yl)-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide Conv.b

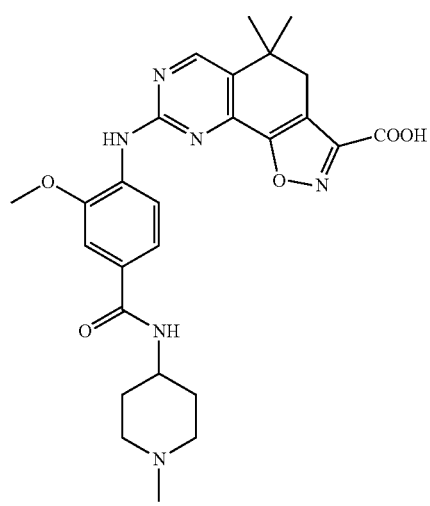

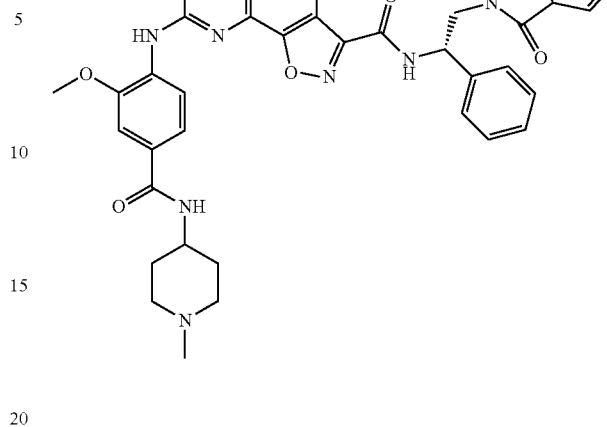

A suspension of potassium 8-({2-methoxy-4-[(1-methylpiperidin-4-yl)carbamoyl]phenyl}amino)-5,5-dimethyl-4,5-dihydroisoxazolo[4,5-h]quinazoline-3-carboxylic acid (70 mg, 0.127 mmol) in anhydrous DMF (3.0 mL) was treated with DIPEA (0.065 mL, 0.38 mmol), 2-[(2S)-2-amino-2-phenylethyl]-1H-isoindole-1,3(2H)-dione dihydrochloride (50 mg, 0.167 mmol) and TBTU (73 mg, 0.23 mmol). The reaction was stirred at room temperature overnight. The reaction was diluted with $H_2O$ and the resulting precipitate was collected by filtration. The crude solid was purified by flash chromatography on silica gel (DCM/MeOH) to afford 30 mg (32% yield) of the title compound.

$[M+H]^+$=755

According to this same methodology, but employing suitable substituted derivatives, the following compounds were prepared:

N-[(1R)-2-(1,3-dioxo-1,3-dihydro-2H-isoindol-2-yl)-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide $[M+H]^+$=755

N-[2-(1H-imidazol-4-yl)ethyl]-5,5-dimethyl-8-{[(4-methylpiperazin-1-yl)phenyl]amino}-5,5-dihydroisoxazolo[4,5-h]quinazoline-3-carboxamide $^1$H NMR (401 MHz, DMSO-$d_6$) δ ppm 1.32 (s, 6H) 2.28 (s, 3H) 2.54 (m, 4H) 2.78 (t, J=7.26 Hz, 2H) 2.90 (s, 2H) 3.03-3.14 (m, 4H) 3.51 (q, J=7.26 Hz, 2H) 6.85 (s, 1H) 6.88-6.94 (m, 2H) 7.57 (d, J=0.73 Hz, 1H) 7.59-7.65 (m, 2H) 8.56 (s, 1H) 8.91 (t, J=5.68 Hz, 1H) 9.61 (s, 1H).
MS calc: 528.2830. MS found: 528.2827.

5,5-dimethyl-8-{[4-(4-methylpiperazin-1-yl)phenyl]amino}-N-(pyridin-4-ylmethyl)-4,5-dihydroisoxazolo[4,5-h]quinazoline-3-carboxamide $^1$H NMR (400 MHz, DMSO-$d_6$) δ ppm 1.32 (s, 6H) 2.24 (br.s., 3H) 2.44-2.49 (m, 4H) 2.92 (s, 2H) 3.02-3.11 (m, 4H) 4.49 (d, J=6.16 Hz, 2H) 6.87-6.94 (m, 2H) 7.27-7.36 (m, 2H) 7.57-7.65 (m, 2H) 8.50-8.55 (m, 2H) 8.57 (s, 1H) 9.52 (t, J=6.16 Hz, 1H) 9.61 (s, 1H).
MS calc: 525.2721. MS found: 525.2726.

Example 9

N-[(1S)-2-amino-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide and N-[(2S)-2-amino-2-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide

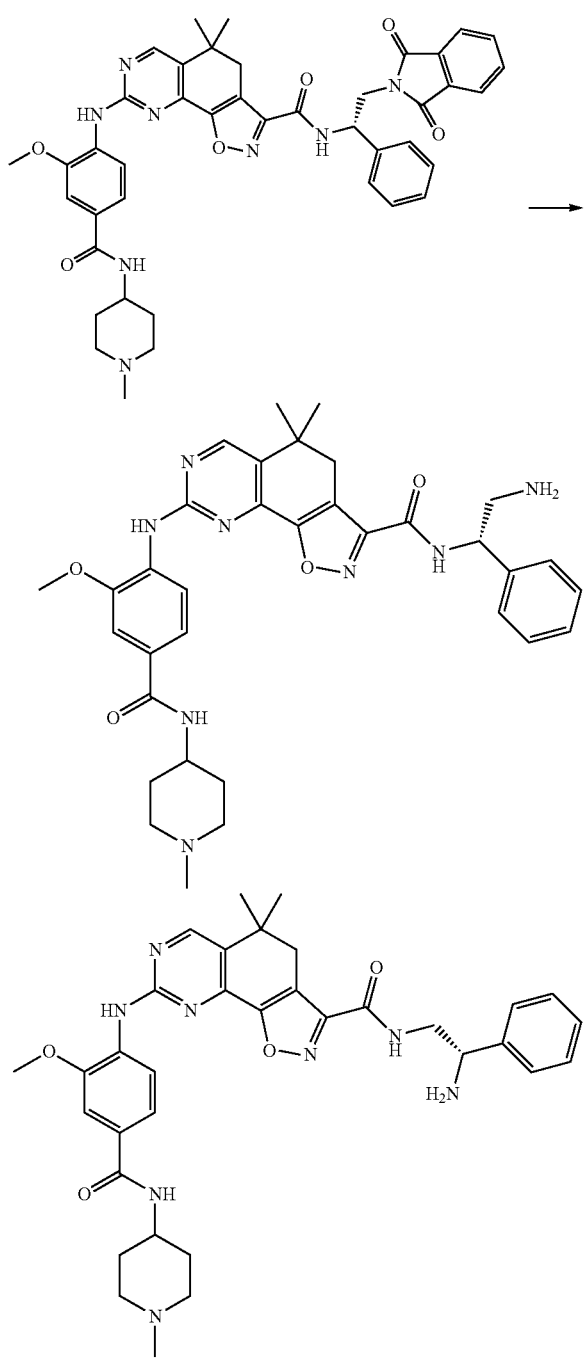

To a solution of N-[(1S)-2-(1,3-dioxo-1,3-dihydro-2H-isoindol-2-yl)-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide (60 mg, 0.079 mmol) in THF (3 mL), 35% hydrazine in water (0.07 mL) was added and the reaction was warmed at 70° C. for 24 hours. The reaction was cooled at room temperature diluted with $H_2O$ (20 mL) and extracted with DCM (2×20 mL). The organic layers were dried over $Na_2SO_4$ and the solvent evaporated to dryness to yield the crude solid that was purified by flash chromatography on silica gel (DCM/MeOH/$NH_3$ 7N in MeOH) to afford the title compounds.

N-[(1S)-2-amino-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide $^1$H NMR (400 MHz, DMSO-$d_6$) δ ppm 1.34 (s, 6H) 1.55-1.64 (m, 2H) 1.77 (m, 2H) 1.94 (m, 2H) 2.17 (s, 3H) 2.77-2.81 (m, 2H) 2.86-2.90 (m, 2H) 2.92 (m, 1H) 3.45-3.55 (m, 1H) 3.73 (m, 1H) 3.94 (m, 3H) 4.06-4.12 (m, 1H) 4.90-4.98 (m, 1H) 7.21-7.27 (m, 1H) 7.30-7.41 (m, 4H) 7.49-7-56 (m, 2H) 8.11 (d, J=7.69 Hz, 1H) 8.35 (d, J=8.42 Hz, 1H) 8.40 (m, 1H) 8.66 (s, 1H) 8.74 (m, 1H) 9.25 (br.s., 1H).

MS calc: 625.3246. MS found: 625.3255.

and

N-[(2S)-2-amino-2-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide MS calc: 625.3246. MS found: 625.3250.

According to this same methodology, but employing suitable substituted derivatives, the following compounds were prepared:

N-[(2R)-2-amino-2-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide $^1$H NMR (400 MHz, DMSO-$d_6$) δ ppm 1.34 (s, 6H) 1.50-1.66 (m, 2H) 1.72-1.83 (m, 2H) 1.90-2.01 (m, 2H) 2.18 (s, 3H) 2.73-2.83 (m, 2H) 2.87 (s, 2H) 3.44-3.58 (m, 1H) 3.66-3.80 (m, 1H) 3.92-3.96 (m, 3H) 4.04-4.15 (m, 1H) 7.21-7.27 (m, 1H) 7.30-7.36 (m, 2H) 7.39-7.42 (m, 2H) 7.51 (d, J=1.83 Hz, 1H) 7.54 (dd, J=8.42, 1.83 Hz, 1H) 8.11 (d, J=7.69 Hz, 1H) 8.35 (d, J=8.42 Hz, 1H) 8.38 (s, 1H) 8.67 (s, 1H) 8.76 (t, J=6.04 Hz, 1H).

MS calc: 625.3246. MS found: 625.3251.

N-[(1R)-2-amino-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide MS calc: 625.3246. MS found: 625.3242.

Example 10

Ethyl 8-[(4-bromo-2-methoxyphenyl)amino]-4,5-dihydroisoxazolo[4,3-h]quinazoline-3-carboxylate st.A3

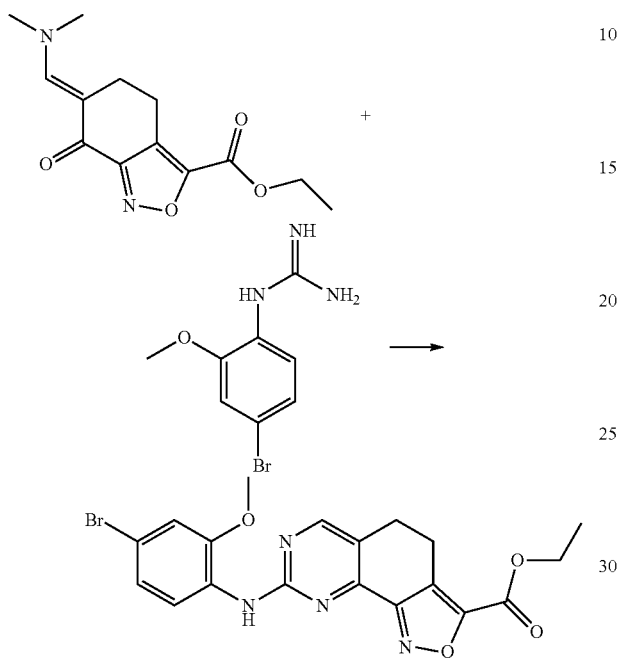

A solution of ethyl-6-[(dimethylamino)methylidene]-7-oxo-4,5,6,7-tetrahydro-2,1-benzisoxazole-3-carboxylate 0.40 g (1.51 mmol) and N-(4-Bromo-2-methoxy-phenyl)-guanidine 0.44 g (1.81 mmol) in 10 mL of EtOH was stirred at 80° C. for 3 hours. After cooling the yellow precipitate formed during the reaction was collected by filtration, washed with cold EtOH and dried, to give 0.360 g (54% yield) of the title compound.

$^1$H NMR (401 MHz, DMSO-d6) δ ppm 1.36 (t, J=7.14 Hz, 3H) 2.88-2.97 (m, 2H) 3.01-3.08 (m, 2H) 3.88 (s, 3H) 4.40 (q, J=7.14 Hz, 2H) 7.16 (dd, J=8.54, 2.20 Hz, 1H) 7.24 (d, J=2.20 Hz, 1H) 8.09 (d, J=8.54 Hz, 1H) 8.37 (s, 1H) 8.60 (s, 1H)

MS calc: 445.0506. MS found: 445.0511.

According to this same methodology, but employing suitable substituted derivatives, the following compounds were prepared:

Ethyl 8-{[4-(tert-butoxycarbonyl)-2-methoxyphenyl]amino}-4,5-dihydroisoxazolo[4,3-h]quinazoline-3-carboxylate $^1$H NMR (401 MHz, DMSO-d6) δ ppm 1.36 (t, J=7.08 Hz, 3H) 1.56 (s, 9H) 2.92-3.01 (m, 2H) 3.03-3.11 (m, 2H) 3.95 (s, 3H) 4.41 (q, J=7.08 Hz, 2H) 7.47-7.52 (m, 2H) 7.58 (dd, J=8.48, 1.77 Hz, 1H) 8.45-8.49 (m, 2H) 8.69 (S, 1H)

MS calc: 467.1925. MS found: 467.1919.

Ethyl 8-{[4-(4-methylpiperazin-1-yl)-2-(trifluoromethoxy)phenyl]amino}-4,5-dihydroisoxazolo[4,3-h]quinazoline-3-carboxylate $^1$H NMR (401 MHz, DMSO-d6) δ ppm 1.35 (t, J=7.14 Hz, 3H) 2.24 (s, 3H) 2.45-2.50 (m, 4H) 2.84-2.91 (m, 2H) 2.99-3.05 (m, 2H) 3.13-3.21 (m, 4H) 4.40 (q, J=7.14 Hz, 2H) 6.87 (d, J=2.69 Hz, 1H) 6.96 (dd, J=9.03, 2.69 Hz, 1H) 7.48 (d, J=9.03 Hz, 1H) 8.46 (s, 1H) 9.06 (s, 1H)

MS calc: 519.1962. MS found: 519.1975.

Ethyl 8-{[2-methoxy-4-(4-methylpiperazin-1-yl)phenyl]amino}-4,5-dihydroisoxazolo[4,3-h]quinazoline-3-carboxylate $^1$H NMR (401 MHz, DMSO-d6) δ ppm 1.35 (t, J=7.14 Hz, 3H) 2.26 (s, 3H) 2.83-2.93 (m, 2H) 2.98-3.06 (m, 2H) 3.10-3.19 (m, 4H) 3.80 (s, 3H) 4.40 (q, J=7.14 Hz, 2H) 6.50 (dd, J=8.79, 2.50 Hz, 1H) 6.64 (d, J=2.50 Hz, 1H) 7.69 (d, J=8.79 Hz, 1H) 8.21 (s, 1H) 8.48 (s, 1H)

MS calc: 465.2245. MS found: 465.2235.

Ethyl 8-{[4-(4-methylpiperazin-1-yl)phenyl]amino}-4,5-dihydroisoxazolo[4,3-h]quinazoline-3-carboxylate $^1$H NMR (401 MHz, DMSO-d6) δ ppm 1.36 (t, J=7.08 Hz, 3H) 2.24 (s, 3H) 2.45-2.50 (m, 4H) 2.84-2.93 (m, 2H) 3.01-3.06 (m, 2H) 3.05-3.10 (m, 4H) 4.40 (q, J=7.08 Hz, 2H) 6.75-6.98 (m, 2H) 7.62 (m, 2H) 8.54 (s, 1H) 9.61 (s, 1H)

MS calc: 435.2139. MS found: 435.2146.

Ethyl 8-amino-4,5-dihydroisoxazolo[4,3-h]quinazoline-3-carboxylate $^1$H NMR (401 MHz, DMSO-d6) δ ppm 1.35 (t, J=7.12 Hz, 3H) 2.72-2.86 (m, 2H) 2.89-3.06 (m, 2H) 4.39 (q, J=7.12 Hz, 2H) 6.82 (br.s., 2H) 8.37 (s, 1H)

MS calc: 261.0982. MS found: 261.0970.

Ethyl 8-({2-methoxy-4-[(1-methylpiperidin-4-yl)carbamoyl]phenyl}amino)-5,5-dimethyl-4,5-dihydroisoxazolo[4,3-h]quinazoline-3-carboxylate $^1$H NMR (401 MHz, DMSO-d6) δ ppm 1.33 (s, 6H) 1.36 (t, J=7.14 Hz, 3H) 1.55-1.70 (m, 2H) 1.76-1.84 (m, 2H) 2.01-2.15 (m, 2H) 2.25 (br. s., 3H) 2.80-2.93 (m, 2H) 2.98 (s, 2H) 3.71-3.86 (m, 1H) 3.95 (s, 3H) 4.42 (q, J=7.14 Hz, 2H) 7.51 (d, J=1.83 Hz, 1H) 7.55 (dd, J=8.54, 1.83 Hz, 1H) 8.14 (d, J=7.69 Hz, 1H) 8.40 (d, J=8.54 Hz, 1H) 8.42 (s, 1H) 8.80 (s, 1H)

MS calc: 535.2664. MS found: 535.2657.

Ethyl 8-({2-methoxy-4-[(1-methylpiperidin-4-yl)carbamoyl]phenyl}amino)-4,4-dimethyl-4,5-dihydroisoxazolo[4,3-h]quinazoline-3-carboxylate $^1$H NMR (401 MHz, DMSO-d$_6$) δ ppm 1-37 (t, J=6.96 Hz, 3H) 1.40 (s, 6H) 1.53-1.67 (m, 2H) 1.73-1.84 (m, 2H) 1.94-2.08 (m, 2H) 2.21 (br. s., 3H) 2.77-2.85 (m, 2H) 2.86 (s, 2H) 3.69-3.83 (m, 1H) 3.95 (s, 3H) 4.44 (q, J=6.96 Hz, 2H) 7.51 (d, J=1.71 Hz, 1H) 7.54 (dd, J=8.42, 1.71 Hz, 1H) 8.12 (d, J=7.81 Hz, 1H) 8.39 (s, 1H) 8.40 (d, J=8.42 Hz) 8.64 (s, 1H).

MS calc: 535.2664. MS found: 535.2656.

Example 11

8-[(4-bromo-2-methoxyphenyl)amino]-N-(2,6-diethylphenyl)-4,5-dihydroisoxazolo[4,3-h]quinazoline-3-carboxamide Conv.c

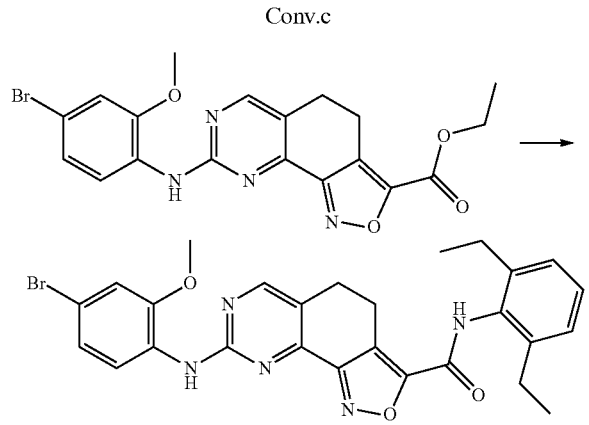

To a solution of ethyl 8-[(4-bromo-2-methoxyphenyl)amino]-4,5-dihydroisoxazolo[4,3-h]quinazoline-3-carboxylate 320 mg (0.72 mmol) and 2,6-diethylaniline 0.177 mL (0.1.08 mmol d 0.906) in 5 mL of anhydrous THF, 2.16 mL of NaHMDS solution (1.0 M in THF, 2.16 mmol) were added dropwise. The mixture was stirred at room temperature for 1 hours. Water was added and the mixture was extracted twice with DCM. The organic layer was dried over $Na_2SO_4$ and the solvent evaporated to dryness. The crude solid was purified by flash chromatography on silica gel (SP1 AcOEt/Hexane) to afford 123 mg (31% yield) of the title compound.

$^1$H NMR (401 MHz, DMSO-d6) δ ppm 1.13 (t, J=7.51 Hz, 6H) 2.55 (q, J=7.51 Hz, 4H) 2.87-2.98 (m, 2H) 3.00-3.11 (m, 2H) 3.89 (s, 3H) 7.13-7.20 (m, 3H) 7.23-7.30 (m, 2H) 8.12 (d, J=8.54 Hz, 1H) 8.39 (s, 1H) 8.60 (s, 1H) 10.35 (s, 1H)

MS calc: 548.1292. MS found: 548.1295.

According to this same methodology, but employing suitable substituted derivatives, the following compounds were prepared:

N-(2,6-diethylphenyl)-8-{[4-(4-methylpiperazin-1-yl)-2-(trifluoromethoxy)phenyl]amino}-4,5-dihydroisoxazolo[4,3-h]quinazoline-3-carboxamide $^1$H NMR (401 MHz, DMSO-d6) δ ppm 1.13 (t, J=7.57 Hz, 6H) 2.32 (br. s., 3H) 2.55 (q, J=7.57 Hz, 4H) 2.58 (br. s., 4H) 2.88 (t, J=7.20 Hz, 2H) 3.04 (t, J=7.20 Hz, 2H) 3.14-3.26 (m, 4H) 6.87-6.91 (m, 1H) 6.98 (dd, J=8.91, 2.75 Hz, 1H) 7.16 (d, J=7.60 Hz, 2H) 7.26 (t, J=7.60 Hz, 1H) 7.50 (d, J=8.91 Hz, 1H) 8.46 (s, 1H) 9.11 (s, 1H) 10.33 (s, 1H)

MS calc: 622.2748. MS found: 622.2751.

N-(2,6-diethylphenyl)-8-{[4-(4-methylpiperazin-1-yl)phenyl]amino}-4,5-dihydroisoxazolo[4,3-h]quinazoline-3-carboxamide $^1$H NMR (401 MHz, DMSO-d6) δ ppm 1.13 (t, J=7.57 Hz, 6H) 2.23 (s, 3H) 2.44-2.48 (m, 4H) 2.55 (q, J=7.57 Hz, 4H) 2.82-2.93 (m, 2H) 2.99-3.13 (m, 6H) 6.86-6.98 (m, 2H) 7.12-7.23 (m, 2H) 7.22-7.31 (m, 1H) 7.57-7.69 (m, 2H) 8.55 (s, 1H) 9.63 (s, 1H) 10.33 (s, 1H)

MS calc: 538.2925. MS found: 538.2925.

Example 12

N-(2,6-diethylphenyl)-8-({4-[4-(2-hydroxyethyl)piperazin-1-yl]-2-methoxyphenyl}amino)-4,5-dihydroisoxazolo[4,3-h]quinazoline-3-carboxamide Conv.d

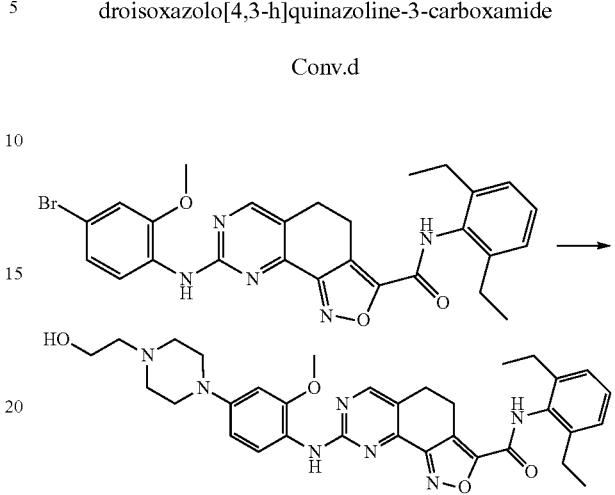

$Pd_2(dba)_3$ 1.3 mg (0.0015 mmol), 2-dicyclohexylphosphino-2'-(N,N-dimethylamino)-biphenyl 1.2 mg, (0.0029 mmol), 8-[(4-bromo-2-methoxyphenyl)amino]-N-(2,6-diethylphenyl)-4,5-dihydroisoxazolo[4,3-h]quinazoline-3-carboxamide 40 mg (0.091 mmol), 2-piperazin-1-yl-ethanol 23 mg (0.219 mmol), in THF (0.5 mL) were charged in a round-bottom flask flushed with argon. The flask was evacuated and backfilled with argon. LiN(TMS)$_2$ solution (1M in THF, 0.58 mL) was added and the reaction mixture refluxed for 1 hours. The reaction mixture was then allowed to cool to room temperature. Water was added, and the mixture was extracted twice with DCM. The organic layer was dried over $Na_2SO_4$ and the solvent was evaporated to dryness. The crude solid was purified by flash chromatography on silica gel (eluant DCM/MeOH/(NH$_3$ 7 N in MeOH) 90/5/0.5) to afford 29 mg (66% yield) of the title compound.

$^1$H NMR (401 MHz, DMSO-d6) δ ppm 1.13 (t, J=7.51 Hz, 6H) 2.45 (t, J=5.19 Hz, 2H) 2.55 (q, J=7.51 Hz, 4H) 2.57-2.64 (m, 4H) 2.82-2.92 (m, 2H) 2.99-3.07 (m, 2H) 3.07-3.19 (m, 4H) 3.50-3.58 (m, 2H) 3.81 (s, 3H) 4.42 (t, J=5.31 Hz, 1H) 6.50 (dd, J=8.67, 2.44 Hz, 1H) 6.64 (d, J=2.44 Hz, 1H) 7.17 (d, J=7.60 Hz, 2H) 7.26 (t, J=7.60 Hz, 1H) 7.69 (d, J=8.67 Hz, 1H) 8.23 (s, 1H) 8.48 (s, 1H) 10.33 (s, 1H)

MS calc: 598.3137. MS found: 598.3144.

According to this same methodology, but employing suitable substituted derivatives, the following compounds were prepared:

N-(2,6-diethylphenyl)-8-{[2-methoxy-4-(4-pyrrolidin-1-ylpiperidin-1-yl)phenyl]amino}-4,5-dihydroisoxazolo[4,3-h]quinazoline-3-carboxamide $^1$H NMR (401 MHz, DMSO-d6) δ ppm 1.13 (t, J=7.51 Hz, 6H) 1.46-1.60 (m, 2H) 1.63-1.75 (m, 4H) 1.88-1.99 (m, 2H) 2.08-2.18 (m, 1H) 2.55 (q, J=7.51 Hz, 4H) 2.66-2.77 (m, 2H) 2.88 (t, J=7.20 Hz, 2H) 3.04 (t, J=7.20 Hz, 2H) 3.57-3.66 (m, 2H) 3.81 (s, 3H) 6.51 (dd, J=8.67, 2.56 Hz, 1H) 6.64 (d, J=2.56 Hz, 1H) 7.17 (d, J=7.60 Hz, 2H) 7.26 (t, J=7.60 Hz, 1H) 7.68 (d, J=8.67 Hz, 1H) 8.22 (s, 1H) 8.48 (s, 1H) 10.33 (s, 1H)

MS calc: 622.35. MS found: 622.3503.

N-(2,6-diethylphenyl)-8-({4-[4-(dimethylamino)piperidin-1-yl]-2-methoxyphenyl}amino)-4,5-dihydroisoxazolo[4,3-h]quinazoline-3-carboxamide $^1$H NMR (401 MHz, DMSO-d6) δ ppm 1.13 (t, J=7.57 Hz, 6H) 1.44-1.60 (m, 2H) 1.81-1.92 (m, 2H) 2.25 (br. s., 1H) 2.30 (br. s., 6H) 2.1-2.72 (m, 2H) 2.88 (t, J=7.20 Hz, 2H) 3.04 (t, J=7.20 Hz, 2H) 3.65-3.75 (m, 2H) 3.81 (s, 3H) 6.51 (dd, J=8.67, 2.32 Hz, 1H) 6.65 (d, J=2.32 Hz, 1H) 7.17 (d, J=7.60 Hz, 2H) 7.26 (t, J=7.60 Hz, 1H) 7.68 (d, J=8.67 Hz, 1H) 8.23 (s, 1H) 8.48 (s, 1H) 10.33 (s, 1H)

MS calc: 596.3344. MS found: 596.3348.

N-(2,6-diethylphenyl)-8-[(4-{[2-(dimethylamino)ethyl](methyl)amino}-2-methoxyphenyl)amino]-4,5-dihydroisoxazolo[4,3-h]quinazoline-3-carboxamide $^1$H NMR (401 MHz, DMSO-d6) δ ppm 1.13 (t, J=7.57 Hz, 6H) 2.22 (br.s., 6H) 2.40-2.46 (m, 2H) 2.55 (q, J=7.57 Hz, 4H) 2.84-2.89 (m, 2H) 2.92 (s, 3H) 3.00-3.07 (m, 2H) 3.42 (t, J=7.14 Hz, 2H) 3.79 (s, 3H) 6.27 (dd, J=8.79, 2.44 Hz, 1H) 6.37 (d, J=2.44 Hz, 1H) 7.14-7.19 (m, 2H) 7.24-7.29 (m, 1H) 7.52 (d, J=8.79 Hz, 1H) 8.21 (s, 1H) 8.44 (s, 1H) 10.33 (s, 1H)

MS calc: 570.3187. MS found: 570.3181.

N-(2,6-diethylphenyl)-8-{[2-methoxy-4-(4-methylpiperazin-1-yl)phenyl]amino}-4,5-dihydroisoxazolo[4,3-h]quinazoline-3-carboxamide $^1$H NMR (401 MHz, DMSO-d6) δ ppm 1.13 (t, J=7.53 Hz, 6H) 2.24 (s, 3H) 2.46-2.49 (m, 4H) 2.55 (q, J=7.53 Hz, 4H) 2.84-2.92 (m, 2H) 2.99-3.07 (m, 2H) 3.11-3.17 (m, 4H) 3.81 (s, 3H) 6.50 (dd, J=8.67, 2.32 Hz, 1H) 6.65 (d, J=2.32 Hz, 1H) 7.14-7.19 (m, 2H) 7.24-7.30 (m, 1H) 7.69 (d, J=8.67 Hz, 1H) 8.23 (s, 1H) 8.48 (s, 1H) 10.34 (s, 1H)

MS calc.: 568.3031. MS found: 568.302.

Example 13

4-{[3-(ethoxycarbonyl)-4,5-dihydroisoxazolo[4,3-h]quinazolin-8-yl]amino}-3-methoxybenzoic acid Conv.e

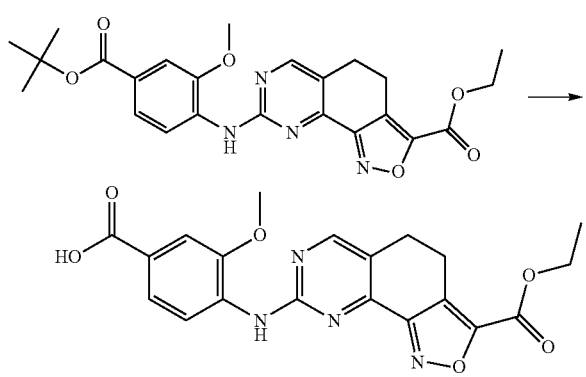

To a solution of 8 ethyl 8-{[4-(tert-butoxycarbonyl)-2-methoxyphenyl]amino}-4,5-dihydroisoxazolo[4,3-h]quinazoline-3-carboxylate (140 mg, 0.30 mmol) in DCM (1.0 mL), TFA (1.0 mL) was added. The mixture was stirred at room temperature for 2 hours. The organic solvent was evaporated to dryness to give the title compound in quantitative yield.

$^1$H NMR (401 MHz, DMSO-d6) δ ppm 1.36 (t, J=7.14 Hz, 3H) 2.96 (t, J=7.08 Hz, 2H) 3.07 (t, J=7.08 Hz, 2H) 3.95 (s, 3H) 4.41 (q, J=7.14 Hz, 2H) 7.54 (d, J=1.83 Hz, 1H) 7.62 (dd, J=8.42, 1.83 Hz, 1H) 8.45 (s, 1H), 8.47 (d, J=8.42 Hz, 1H), 8.69 (s, 1H), 11.95 (br.s., 1H)

MS calc: 411.1299. MS found: 411.1303.

Example 14

N-(2,6-diethylphenyl)-8-[(4-{[4-(dimethylamino)piperidin-1-yl]carbonyl}-2-methoxyphenyl)amino]-4,5-dihydroisoxazolo[4,3-h]quinazoline-3-carboxamide Conv.f

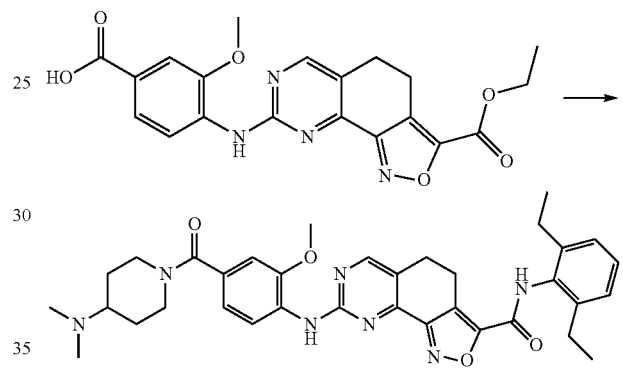

A solution of 4-{[3-(ethoxycarbonyl)-4,5-dihydroisoxazolo[4,3-h]quinazolin-8-yl]amino}-3-methoxybenzoic acid (40 mg, 0.098 mmol) in anhydrous DMF (0.5 mL) was treated with DIPEA (0.150 mL) and TBTU (47 mg, 0.146 mmol). The mixture was then treated with 4-dimethylamine-piperidine (15 mg, 1.26 mmol) and was stirred at room temperature for 1 hours. The reaction was diluted with water and extracted twice with DCM. The organic layer was dried over Na$_2$SO$_4$ and the solvent was evaporated to dryness. The residue was dissolved in 0.5 mL of anhydrous THF and 2,6-diethylaniline 0.024 mL (0.127 mmol) was added. Then NaHMDS solution, 0.300 mL (1.0 M in THF, 0.30 mmol), was added dropwise. The mixture was stirred at room temperature for 1 hours. H$_2$O was added and the mixture was extracted twice with DCM. The organic layer was dried over Na$_2$SO$_4$ and the solvent evaporated to dryness. The crude solid was purified by flash chromatography on silica gel (DCM/MeOH) to afford 15 mg (25% yield) of the title compound.

$^1$H NMR (401 MHz, DMSO-d6) δ ppm 1.13 (t, J=7.57 Hz, 6H) 1.29-1.45 (m, 2H) 1.78 (m, 2H) 2.20 (br.s., 6H) 2.33-2.45 (m, 1H) 2.56 (q, J=7.57 Hz, 4H) 2.92-2.98 (m, 2H) 3.04-3.11 (m, 2H) 3.26-3.32 (m, 4H) 3.91 (s, 3H) 7.02 (dd, J=8.18, 1.71 Hz, 1H) 7.07 (d, J=1.71 Hz, 1H) 7.14-7.20 (m, 2H) 7.23-7.30 (m, 1H) 8.30 (d, J=8.18 Hz, 1H) 8.40 (s, 1H) 8.64 (s, 1H) 10.35 (s, 1H)

MS calc: 624.3293. MS found: 624.3307.

According to this same methodology, but employing suitable substituted derivatives, the following compounds were prepared:

N-(2,6-diethylphenyl)-8-[(4-{[2-(dimethylamino)ethyl]carbamoyl}-2-methoxyphenyl)amino]-4,5-dihydroisoxazolo[4,3-h]quinazoline-3-carboxamide ¹H NMR (401 MHz, DMSO-d6) δ ppm 1.13 (t, J=7.57 Hz, 6H) 2.19 (s, 6H) 2.41 (t, J=6.96 Hz, 2H) 2.56 (q, J=7.57 Hz, 4H) 2.92-3.00 (m, 2H) 3.04-3.12 (m, 2H) 3.33-3.42 (m, 2H) 3.96 (s, 3H) 7.14-7.20 (m, 2H) 7.24-7.30 (m, 1H) 7.50-7.54 (m, 2H) 8.30 (t, J=5.61 Hz, 1H) 8.38 (d, J=8.60 Hz, 1H) 8.40 (s, 1H) 8.67 (s, 1H) 10.36 (s, 1H)

MS calc: 584.298. MS found: 584.299.

N-(2,6-diethylphenyl)-8-[(2-methoxy-4-{[(2S)-2-(pyrrolidin-1-ylmethyl)pyrrolidin-1-yl]carbonyl}phenyl)amino]-4,5-dihydroisoxazolo[4,3-h]quinazoline-3-carboxamide ¹H NMR (401 MHz, DMSO-d6) δ ppm 1.13 (t, J=7.57 Hz, 6H) 1.55-1.79 (m, 4H) 1.82-1.93 (m, 2H) 1.95-2.07 (m, 2H) 2.56 (q, J=7.57 Hz, 4H) 2.91-2.98 (m, 2H) 3.03-3.12 (m, 2H) 3.43-3.61 (m, 2H) 3.92 (s, 3H) 4.17-4.34 (br. s., 1H) 7.10-7.19 (m, 2H) 7.24-7.30 (m, 1H) 8.33 (d, J=8.18 Hz, 1H) 8.39 (s, 1H) 8.65 (s, 1H) 10.35 (s, 1H)

MS calc: 650.345. MS found: 650.3451.

N-(2,6-diethylphenyl)-8-[(2-methoxy-4-{[(2R)-2-(pyrrolidin-1-ylmethyl)pyrrolidin-1-yl]carbonyl}phenyl)amino]-4,5-dihydroisoxazolo[4,3-h]quinazoline-3-carboxamide ¹H NMR (401 MHz, DMSO-d6) δ ppm 1.13 (t, J=7.57 Hz, 6H) 1.54-1.79 (m, 4H) 1.82-1.93 (m, 2H) 1.94-2.08 (m, 2H) 2.56 (q, J=7.57 Hz, 4H) 2.91-2.98 (m, 2H) 3.03-3.12 (m, 2H) 3.43-3.61 (m, 2H) 3.92 (s, 3H) 4.16-4.34 (br. s., 1H) 7.10-7.19 (m, 2H) 7.24-7.30 (m, 1H) 8.33 (d, J=8.18 Hz, 1H) 8.39 (s, 1H) 8.65 (s, 1H) 10.35 (s, 1H)

MS calc: 650.345. MS found: 650.3465.

Example 15

8-{[4-(4-methylpiperazin-1-yl)-2-(trifluoromethoxy)phenyl]amino}-4,5-dihydroisoxazolo[4,3-h]quinazoline-3-carboxamide Conv.c

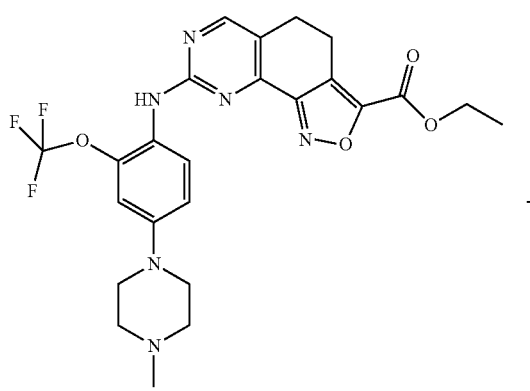

→

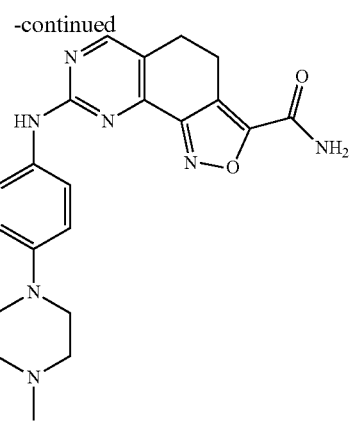

To a mixture of ethyl 8-{[4-(4-methylpiperazin-1-yl)-2-(trifluoromethoxy)phenyl]amino}-4,5-dihydroisoxazolo[4,3-h]quinazoline-3-carboxylate 15 mg (0.029 mmol) in MeOH, NH₃ solution, 0.5 mL (7N in MeOH) was added. The reaction was stirred for 20 minutes and then the solvent was evaporated to dryness, to give the title compound in quantitative yield.

¹H NMR (401 MHz, DMSO-d6) δ ppm 2.24 (s, 3H) 2.42-2.48 (m, 4H) 2.79-2.88 (m, 2H) 2.94-3.03 (m, 2H) 3.11-3.21 (m, 4H) 6.82-6.89 (m, 1H) 6.96 (dd, J=9.03, 2.69 Hz, 1H) 7.48 (d, J=9.03 Hz, 1H) 7.98 (br.s., 1H) 8.30 (br.s., 1H) 8.43 (s, 1H) 9.04 (s, 1H)

MS calc: 490.1809. MS found: 490.1811.

According to this same methodology, but employing suitable substituted derivatives, the following compounds were prepared:

8-{[2-methoxy-4-(4-methylpiperazin-1-yl)phenyl]amino}-4,5-dihydroisoxazolo[4,3-h]quinazoline-3-carboxamide ¹H NMR (401 MHz, DMSO-d6) δ ppm 2.24 (s, 3H) 2.44-2.49 (m, 4H) 2.79-2.87 (m, 2H) 2.94-3.03 (m, 2H) 3.09-3.18 (m, 4H) 3.80 (s, 3H) 6.50 (dd, J=8.67, 2.44 Hz, 1H) 6.64 (d, J=2.44 Hz, 1H) 7.69 (d, J=8.67 Hz, 1H) 7.98 (s, 1H) 8.18 (s, 1H) 8.30 (s, 1H) 8.46 (s, 1H)

MS calc: 436.2092. MS found: 436.2071.

8-{[4-(4-methylpiperazin-1-yl)phenyl]amino}-4,5-dihydroisoxazolo[4,3-h]quinazoline-3-carboxamide ¹H NMR (401 MHz, DMSO-d6) δ ppm 2.22 (s, 3H) 2.42-2.47 (m, 4H) 2.80-2.89 (m, 2H) 2.98-3.03 (m, 2H) 3.04-3.09 (m, 4H) 6.74-6.98 (m, 2H) 7.58-7.65 (m, 2H) 7.99 (br.s., 1H) 8.31 (br.s., 1H) 8.52 (s, 1H) 9.59 (s, 1H)

MS calc: 406.1986. MS found: 406.1983.

8-[(4-bromo-2-methoxyphenyl)amino]-N,N-dimethyl-4,5-dihydroisoxazolo[4,3-h]quinazoline-3-carboxamide ¹H NMR (401 MHz, DMSO-d6) δ ppm 2.78-2.87 (m, 2H) 2.93-3.00 (m, 2H) 3.05 (s, 3H) 3.13 (s, 3H) 3.88 (s, 3H) 7.17 (dd, J=8.54, 2.20 Hz, 1H) 7.24 (d, J=2.20 Hz, 1H) 8.09 (d, J=8.54 Hz, 1H) 8.26-8.37 (m, 1H) 8.50 (s, 1H)

MS calc: 444.0666. MS found: 444.0662.

8-amino-4,5-dihydroisoxazolo[4,3-h]quinazoline-3-carboxamide $^1$H NMR (401 MHz, DMSO-d6) δ ppm 2.78 (t, J=7.25 Hz, 2H) 2.97 (t, J=7.25 Hz, 2H) 6.79 (br.s., 1H) 7.96 (br.s., 1H) 8.29 (br.s., 1H) 8.35 (s, 1H)

MS calc: 232.0829. MS found: 232.0837.

8-({2-methoxy-4-[(1-methylpiperidin-4-yl)carbamoyl]phenyl}amino)-5,5-dimethyl-4,5-dihydroisoxazolo[4,3-h]quinazoline-3-carboxamide $^1$H NMR (400 MHz, DMSO-d$_6$) δ ppm 1.32 (s, 6H) 1.56-1.71 (m, 2H) 1.73-1.87 (m, 2H) 1.89-2.17 (m, 2H) 2.25 (br. s., 3H) 2.80-2.92 (m, 2H) 2.96 (s, 2H) 3.69-3.84 (m, 1H) 3.95 (s, 3H) 7.51 (d, J=1.71 Hz, 1H) 7.54 (dd, J=8.54 and 1.71 Hz, 1H) 8.04 (br.s., 1H) 8.14 (d, J=7.45 Hz, 1H) 8.34 (br.s., 1H) 8.39 (s, 1H) 8.40 (d, J=8.54 Hz, 1H) 8.78 (s, 1H).

MS calc: 506.2511. MS found: 506.2520.

8-({2-methoxy-4-[(1-methylpiperidin-4-yl)carbamoyl]phenyl}amino)-4,4-dimethyl-4,5-dihydroisoxazolo[4,3-h]quinazoline-3-carboxamide $^1$H NMR (400 MHz, DMSO-d$_6$) δ ppm 1.37 (s, 6H) 1.61 (d, J=15.14 Hz, 2H) 1.79 (d, J=9.28 Hz, 2H) 1.95-2.07 (m, 2H) 2.21 (br. s., 3H) 2.82 (s, 2H) 2.85 (br. s., 2H) 3.76 (br. s., 1H) 3.94-3.96 (m, 3H) 7.51 (d, J=1.71 Hz, 1H) 7.54 (dd, J=8.24, 1.77 Hz, 1H) 8.07 (s, 1H) 8.11 (d, J=7.69 Hz, 1H) 8.36 (s, 1H) 8.40 (d, J=8.42 Hz, 1H) 8.43 (s, 1H) 8.62 (s, 1H).

MS calc: 506.2511. MS found: 506.2525.

5,5-dimethyl-8-{[4-(4-methylpiperazin-1-yl)phenyl]amino}-4,5-dihydroisoxazolo[4,3-h]quinazoline-3-carboxamide $^1$H NMR (400 MHz, DMSO-d$_6$) δ ppm 1.30 (s, 6H) 2.27-2.44 (m, 2H) 2.56-2.76 (m, 4H) 2.94 (s, 2H) 3.03-3.19 (m, 2H) 6.91 (d, J=9.03 Hz, 1H) 7.64 (d, J=9.03 Hz, 1H) 8.02 (s, 1H) 8.31 (s, 1H) 8.66 (s, 1H) 9.66 (s, 1H).

MS calc: 434.2299. MS found: 434.2306.

5,5-dimethyl-8-{[4-(4-methylpiperazin-1-yl)-2-(trifluoromethoxy)phenyl]amino}-4,5-dihydroisoxazolo[4,3-h]quinazoline-3-carboxamide $^1$H NMR (401 MHz, DMSO-d$_6$) δ ppm 1.27 (s, 6H) 2.28-2.35 (m, 2H) 2.54-2.63 (m, 4H) 2.93 (s, 2H) 3.16-3.22 (m, 2H) 6.88 (d, J=2.69 Hz, 1H) 6.97 (dd, J=8.91, 2.69 Hz, 1H) 7.51 (d, J=8.91 Hz, 1H) 8.01 (br.s., 1H) 8.31 (br.s., 1H) 8.58 (s, 1H) 9.11 (s, 1H).

MS calc: 518.2122. MS found: 518.2120.

Example 16

8-[(4-bromo-2-methoxyphenyl)amino]-4,5-dihydroisoxazolo[4,3-h]quinazoline-3-carboxylic acid Conv.a

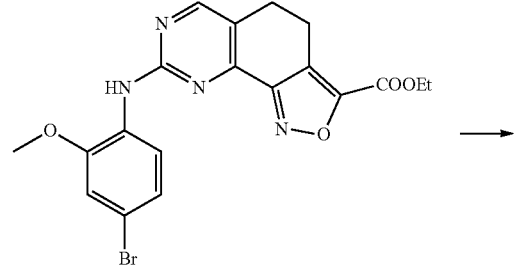

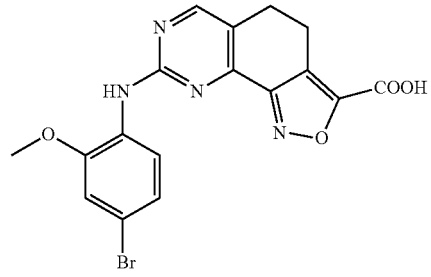

Ethyl 8-[(4-bromo-2-methoxyphenyl)amino]-4,5-dihydroisoxazolo[4,3-h]quinazoline-3-carboxylate (45 mg, 0.1 mmol) was suspended in anhydrous EtOH (2 mL) and treated with a 1.5 M solution of KOH (0.07 mL, 0.1 eq.) at room temperature for 1 hour. Solvent was evaporated to dryness and the residue dissolved in H$_2$O. After treatment with AcOH and the resulting precipitate was collected by filtration to give the title compound (30 mg, 70% yield).

$^1$H NMR (401 MHz, DMSO-d6) δ ppm 2.79-2.85 (m, 2H) 2.91-2.98 (m, 2H) 3.89 (s, 3H) 7.13 (br.s., 1H) 7.16 (dd, J=8.61, 2.20 Hz, 1H) 7.22 (d, J=2.20 Hz, 1H) 8.15-8.23 (m, 2H) 8.53 (s, 1H)

MS calculated: 417.0193. MS found: 417.0193.

According to this same methodology, but employing suitable substituted derivatives, the following compound was prepared:

8-{[2-methoxy-4-(4-methylpiperazin-1-yl)phenyl]amino}-4,5-dihydroisoxazolo[4,3-h]quinazoline-3-carboxylic acid Example 17

N-(2,6-diethylphenyl)-8-{[2-methoxy-4-(4-methylpiperazin-1-yl)phenyl]amino}-4,5-dihydroisoxazolo[4,3-h]quinazoline-3-carboxamide

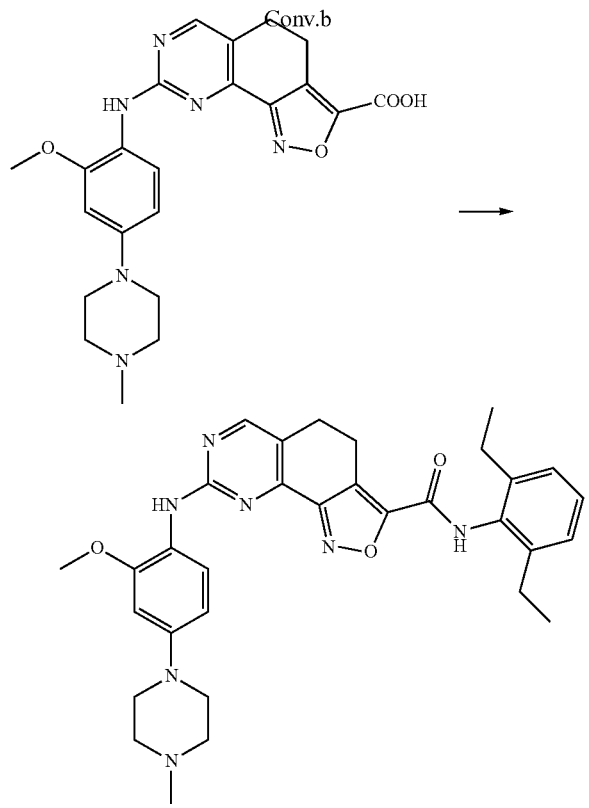

A suspension of potassium 8-{[2-methoxy-4-(4-methylpiperazin-1-yl)phenyl]amino}-4,5-dihydroisoxazolo[4,3-h]quinazoline-3-carboxylic acid (40 mg, 0.09 mmol) in anhydrous DMF (3.0 mL) was treated with DIPEA (0.026 mL, 0.15 mmol) and (EDCI) (38 mg, 0.20 mmol) and HOBt (27 mg, 0.20 mmol). The mixture was then treated with 2,6-diethylaniline (0.040 mL, 0.25 mmol). The reaction was stirred at room temperature overnight. The reaction was diluted with H$_2$O and the resulting precipitate was collected by filtration. The crude solid was purified by flash chromatography on silica gel (DCM/MeOH) to afford 15 mg (30% yield) of the title compound.

$^1$H NMR (401 MHz, DMSO-d6) δ ppm 1.13 (t, J=7.53 Hz, 6H) 2.24 (s, 3H) 2.46-2.49 (m, 4H) 2.55 (q, J=7.53 Hz, 4H) 2.84-2.92 (m, 2H) 2.99-3.07 (m, 2H) 3.11-3.17 (m, 4H) 3.81 (s, 3H) 6.50 (dd, J=8.67, 2.32 Hz, 1H) 6.65 (d, J=2.32 Hz, 1H) 7.14-7.19 (m, 2H) 7.24-7.30 (m, 1H) 7.69 (d, J=8.67 Hz, 1H) 8.23 (s, 1H) 8.48 (s, 1H) 10.34 (s, 1H)

MS calc.: 568.3031. MS found: 568.302.

According to this same methodology, but employing suitable substituted derivatives, the following compounds were prepared:

Tert-butyl [(2S)-2-({[8-({2-methoxy-4-[(1-methylpiperidin-4-yl)carbamoyl]phenyl}amino)-5,5-dimethyl-4,5-dihydroisoxazolo[4,3-h]quinazolin-3-yl]carbonyl}amino)-2-phenylethyl]carbamate $^1$H NMR (401 MHz, DMSO-d$_6$) δ ppm 1.29 (s, 3H) 1.31 (s, 3H) 1.34 (s, 9H) 1.53-1.67 (m, 2H) 1.73-1.83 (m, 2H) 1.90-2.04 (m, 2H) 2.18 (s, 3H) 2.74-2.85 (m, 2H) 2.94 (s, 2H) 3.35-3.49 (m, 2H) 3.62-3.82 (m, 1H) 3.95 (s, 3H) 5.09-5.19 (m, 1H) 7.05 (t, J=6.10 Hz, 1H) 7.26 (m, 1H) 7.34 (t, J=7.51 Hz, 2H) 7.38-7.45 (m, 2H) 7.50-7.59 (m, 2H) 8.12 (d, J=7.57 Hz, 1H) 8.37 (d, J=8.18 Hz, 1H) 8.41 (s, 1H) 8.77 (s, 1H) 9.35 (d, J=8.30 Hz, 1H).

MS calc: 725.377. MS found: 725.378.

Tert-butyl [(2S)-2-({[8-({2-methoxy-4-[(1-methylpiperidin-4-yl)carbamoyl]phenyl}amino)-4,4-dimethyl-4,5-dihydroisoxazolo[4,3-h]quinazolin-3-yl]carbonyl}amino)-2-phenylethyl]carbamate $^1$H NMR (401 MHz, DMSO-d$_6$) δ ppm 1.26 (s, 6H) 1.35 (s, 9H) 1.55-1.68 (m, 2H) 1.72-1.83 (m, 2H) 1.95-2.08 (m, 2H) 2.21 (s, 3H) 2.80 (s, 2H) 2.80-2.86 (m, 2H) 3.68-3.82 (m, 1H) 3.95 (s, 3H) 5.13-5.23 (m, 1H) 6.98 (t, J=5.98 Hz, 1H) 7.27 (t, J=6.71 Hz, 1H) 7.32-7.42 (m, 4H) 7.50-7.56 (m, 2H) 8.12 (d, J=7.69 Hz, 1H) 8.33-8.42 (m, 2H) 8.62 (s, 1H) 9.44 (d, J=8.30 Hz, 1H).

MS calc: 725.377. MS found: 725.3779.

5,5-dimethyl-8-{[4-(4-methylpiperazin-1-yl)phenyl]amino}-N-(pyridin-4-ylmethyl)-4,5-dihydroisoxazolo[4,3-h]quinazoline-3-carboxamide $^1$H NMR (400 MHz, DMSO-d$_6$) δ ppm 1.30 (s, 6H) 2.82-2.93 (m, 5H) 2.96 (s, 2H) 3.09-3.25 (m, 2H) 3.47-3.62 (m, 2H) 3.68-3.82 (m, 2H) 4.54 (d, J=6.10 Hz, 1H) 6.91-7.02 (m, 2H) 7.09 (s, 1H) 7.22 (s, 1H) 7.44 (d, J=5.98 Hz, 2H) 7.65-7.74 (m, 2H) 8.58 (d, J=5.98 Hz, 2H) 8.69 (s, 1H) 9.62 (t, J=6.10 Hz, 1H) 9.74 (s, 1H).

MS calc: 525.2721. MS found: 525.2730.

Example 18

Methyl 8-[(4-bromo-2-methoxyphenyl)amino]-4,5-dihydroisoxazolo[4,3-h]quinazoline-3-carboxylate Conv.j

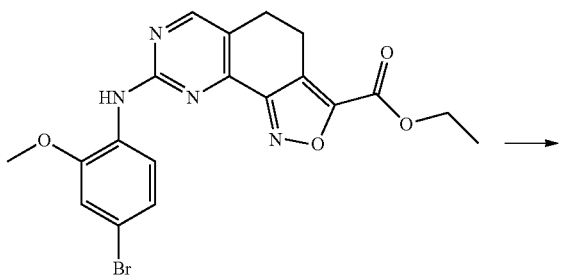

-continued

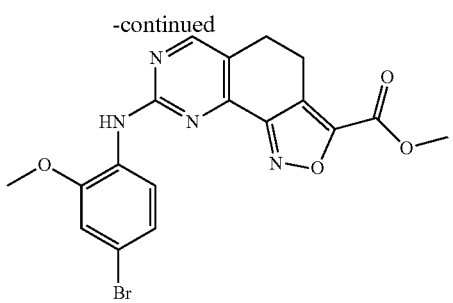

To a mixture of ethyl 8-[(4-bromo-2-methoxyphenyl)amino]-4,5-dihydroisoxazolo[4,3-h]quinazoline-3-carboxylate 40 mg (0.090 mmol) in MeOH, was added was stirred for 20 minutes and then the solvent was evaporated to dryness, to give the title compound in quantitative yield.

$^1$H NMR (401 MHz, DMSO-d6) δ ppm 2.88-2.95 (m, 2H) 3.01-3.08 (m, 2H) 3.88 (s, 3H) 3.94 (s, 3H) 7.16 (dd, J=8.67, 2.20 Hz, 1H) 7.24 (d, J=2.20 Hz, 1H) 8.09 (d, J=8.67 Hz, 1H) 8.37 (s, 1H) 8.60 (s, 1H)

MS calc: 431.035. MS found: 431.0355.

Example 19

8-{[2-methoxy-4-(4-methylpiperazin-1-yl)phenyl]amino}-4,5-dihydroisoxazolo[4,5-h]quinazoline-3-carboxylic acid Conv.a

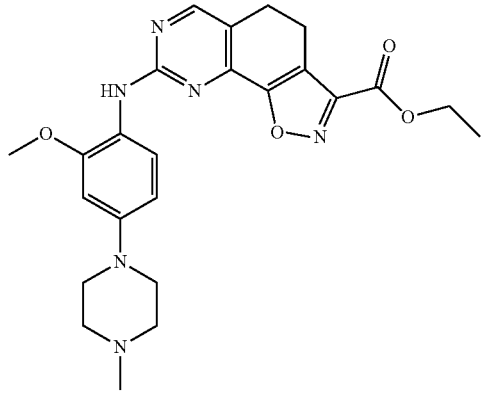

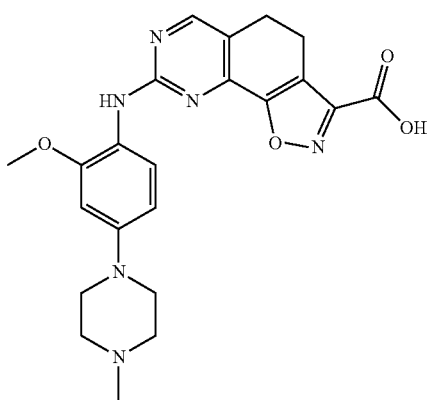

Ethyl 8-{[4-(4-methylpiperazin-1-yl)phenyl]amino}-4,5-dihydroisoxazolo[4,5-h]quinazoline-3-carboxylate (90 mg, 0.2 mmol) was suspended in EtOH (5 mL) and treated with a 0.1 M solution of NaOH (2.0 mL, 0.2 mmol.) at room temperature for 0.5 hour. Solvent was evaporated to dryness and the residue dissolved in H$_2$O. After treatment with AcOH and the resulting precipitate was collected by filtration to give the title compound (85 mg, 98% yield).

M+H]$^+$=437

Example 20

N-(2,6-diethylphenyl)-8-{[2-methoxy-4-(4-methylpiperazin-1-yl)phenyl]amino}-4,5-dihydroisoxazolo[4,5-h]quinazoline-3-carboxamide Conv.b

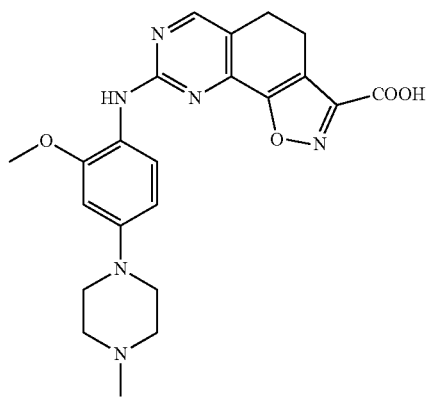

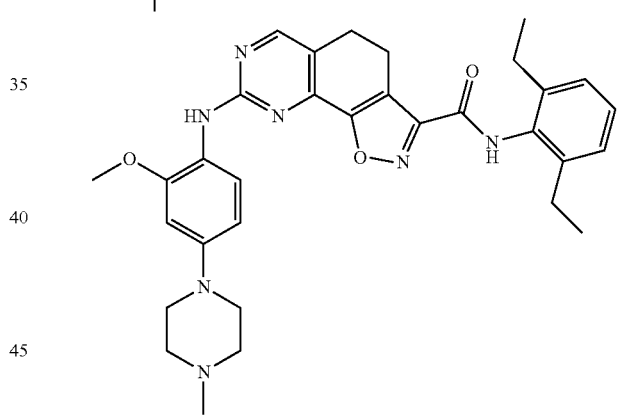

A suspension of potassium 8-{[2-methoxy-4-(4-methylpiperazin-1-yl)phenyl]amino}-4,5-dihydroisoxazolo[4,5-h]quinazoline-3-carboxylic acid (85 mg, 0.20 mmol) in anhydrous DMF (4.0 mL) was treated with DIPEA (0.052 mL, 0.30 mmol) and EDCI (75 mg, 0.40 mmol) and 1-hydroxybenzotriazole (54 mg, 0.40 mmol). The mixture was then treated with 2,6-diethylaniline (0.078 mL, 0.50 mmol). The reaction was stirred at room temperature for 48 hours. The reaction was diluted with H$_2$O and the resulting precipitate was collected by filtration. The crude solid was purified by flash chromatography on silica gel (DCM/MeOH) to afford 50 mg (45% yield) of the title compound.

$^1$H NMR (401 MHz, DMSO-d6) δ ppm 1.13 (t, J=7.57 Hz, 6H) 2.25 (s, 3H) 2.46-2.51 (m, 4H) 2.56 (q, J=7.57 Hz, 3H) 2.85-3.01 (m, 4H) 3.09-3.19 (m, 4H) 3.81 (s, 3H) 6.51 (dd, J=8.67, 2.56 Hz, 1H) 6.64 (d, J=2.56 Hz, 1H) 7.05-7.21 (m, 1H) 7.20-7.37 (m, 1H) 7.65 (d, J=8.67 Hz, 1H) 8.22 (s, 1H) 8.39 (s, 1H) 10.29 (s, 1H)

MS calc.: 568.3031. MS found: 568.3027.

Example 21

Methyl 8-[(4-bromo-2-methoxyphenyl)amino]-4,5-dihydroisoxazolo[4,5-h]quinazoline-3-carboxylate Conv.j

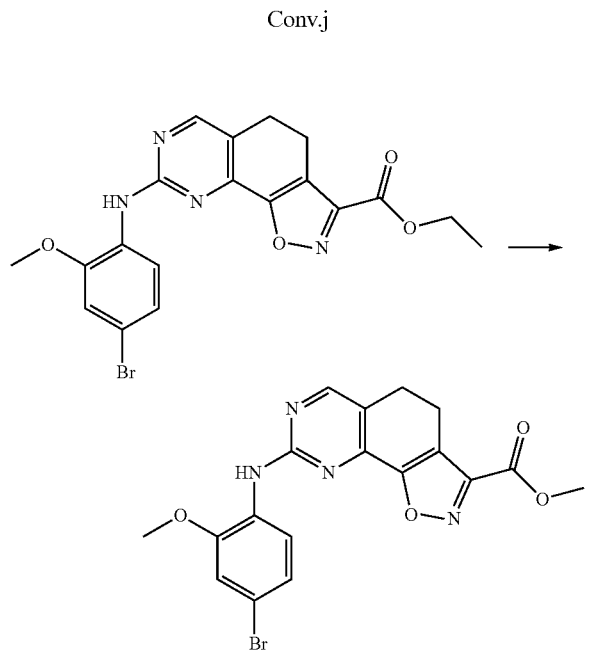

To a mixture of ethyl 8-[(4-bromo-2-methoxyphenyl)amino]-4,5-dihydroisoxazolo[4,5-h]quinazoline-3-carboxylate 10 mg (0.002 mmol) in MeOH, was added was stirred for 30 minutes and then the solvent was evaporated to dryness, to give the title compound in quantitative yield.

$^1$H NMR (401 MHz, DMSO-d6) δ ppm 2.97-3.00 (m, 4H) 3.88 (s, 3H) 3.94 (s, 3H) 7.09-7.20 (m, 1H) 7.24 (d, J=2.20 Hz, 1H) 8.05 (d, J=8.54 Hz, 1H) 8.35 (s, 1H) 8.51 (s, 1H)

MS calc: 431.035. MS found: 431.0356.

Example 22

N-[(1S)-2-amino-1-phenylethyl]-8-({2-methoxy-4-[(1-methylpiperidin-4-yl)carbamoyl]phenyl}amino)-5,5-dimethyl-4,5-dihydroisoxazolo[4,3-h]quinazoline-3-carboxamide

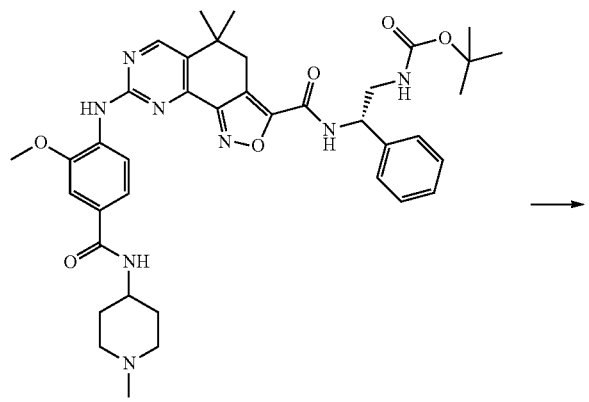

To a mixture of tert-butyl [(2S)-2-({[8-({2-methoxy-4-[(1-methylpiperidin-4-yl)carbamoyl]phenyl}amino)-5,5-dimethyl-4,5-dihydroisoxazolo[4,3-h]quinazolin-3-yl]carbonyl}amino)-2-phenylethyl]carbamate 110 mg (0.151 mmol) in MeOH (1 mL), 0.378 mL of 4 N HCl in dioxane was added. The reaction was stirred at room temperature for 12 h, the solvent was evaporated to dryness and the solid treated with Et$_2$O (20 mL) and the precipitated collected by filtration to give the title compound as a pale yellow solid (96 mg; 91% yield).

$^1$H NMR (400 MHz, DMSO-d$_6$) δ ppm 1.31 (s, 6H) 1.81-2.08 (m, 4H) 2.69-2.81 (m, 3H) 2.97 (s, 2H) 3.03-3.16 (m, 4H) 3.96 (s, 3H) 3.99-4.10 (m, 1H) 5.26-5.46 (m, 1H) 7.28-7.52 (m, 5H) 7.54-7.59 (m, 2H) 8.14 (br. s., 3H) 8.36-8.39 (m, 1H) 8.40-8.49 (m, 2H) 8.79 (s, 1H) 9.62 (d, J=8.54 Hz, 1H) 10.27 (br. s., 1H).

MS calc: 625.3246. MS found: 625.3262.

According to this same methodology, but employing suitable substituted derivatives, the following compound was prepared:

N-[(1S)-2-amino-1-phenylethyl]-8-({2-methoxy-4-[(1-methylpiperidin-4-yl)carbamoyl]phenyl}amino)-4,4-dimethyl-4,5-dihydroisoxazolo[4,3-h]quinazoline-3-carboxamide $^1$H NMR (400 MHz, DMSO-d$_6$) δ ppm 1.29 (s, 3H) 1.40 (s, 3H) 1.82-1.96 (m, 2H) 1.97-2.08 (m, 2H) 2.71-2.76 (m, 3H) 2.82 (s, 2H) 3.02-3.15 (m, 2H) 3.40-3.52 (m, 2H) 3.96 (s, 3H) 3.99-4.12 (m, 1H) 5.31-5.42 (m, 1H) 7.34 (t, J=6.84 Hz, 1H) 7.39-7.44 (m, 2H) 7.44-7.48 (m, 2H) 7.54-7.59 (m, 2H) 8.14 (br. s., 3H) 8.35-8.47 (m, 3H) 8.64 (s, 1H) 9.67 (d, J=8.54 Hz, 1H) 10.22 (br. s., 1H)

MS calc: 625.3246. MS found: 625.3262.

Example 23

Ethyl 8-(methylsulfanyl)-4,5-dihydroisoxazolo[4,5-h]quinazoline-3-carboxylate st.A3

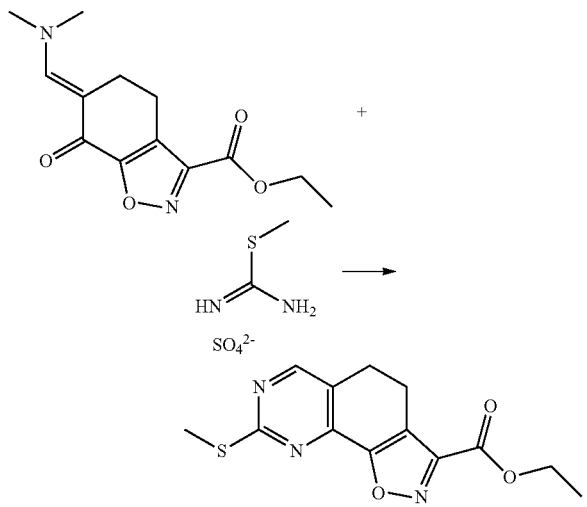

A solution of ethyl-6-[(dimethylamino)methylidene]-7-oxo-4,5,6,7-tetrahydro-1,2-benzisoxazole-3-carboxylate 1.53 g (5.8 mmol), S-methyl isothiourea sulphate 1.76 g (6.3 mmol) and potassium acetate 1.25 g (12.7 mmol) in 30 mL of DMF was stirred at 85° C. for 3 hours.

After cooling, the reaction was worked up with $H_2O$ and AcOEt. The pooled organic extracts were washed with brine, dried over $Na_2SO_4$ and evaporated down. The crude material was purified by silica/flash column chromatography (eluant: Hexane/AcOEt 3/2) to give the clean product in 74% yield.

$^1$H NMR (DMSO-d$_6$) δ 1.35 (t, J=7.14 Hz, 3H), 2.56 (s, 3H), 2.95-3.13 (m, 4H), 4.41 (q, J=7.14 Hz, 2H), 8.68 (s, 1H)

MS calc: 292.0751. MS found: 292.0741.

Example 24

8-(methylsulfanyl)-4,5-dihydroisoxazolo[4,5-h]quinazoline-3-carboxamide

Conv.b

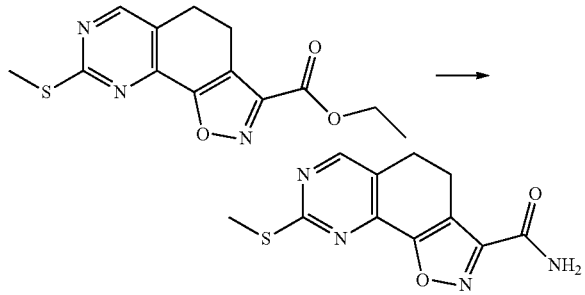

To a suspension of ethyl 8-(methylsulfanyl)-4,5-dihydroisoxazolo[4,5-h]quinazoline-3-carboxylate 60 mg (0.22 mmol) in MeOH, $NH_3$ 7N in MeOH (0.5 mL) was added. The mixture was reacted for 2 hours in a sealed vial at 90° C.; the solvent was then evaporated to dryness, to give the title compound in quantitative yield.

$^1$H NMR (DMSO-d$_6$) δ 2.56 (s, 3H), 2.92-3.09 (m, 4H), 7.92 (s, 1H), 8.24 (s, 1H), 8.66 (s, 1H).

MS calc: 263.0597. MS found: 263.059.

Preparation H 4-(4-methylpiperazin-1-yl)phenol

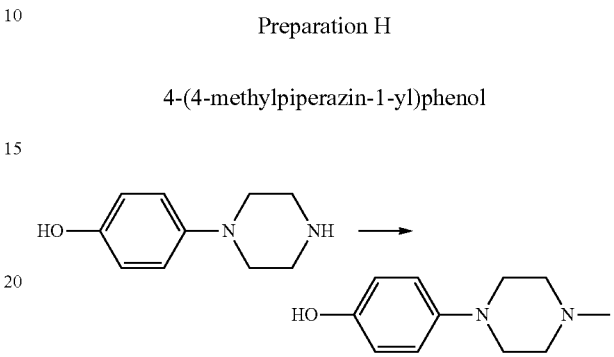

4-(piperazin-1-yl)phenol 2 g (11.24 mmol) and formaldehyde 4.5 mL (37% in water, 56 mmol) were suspended in a mixture of THF/AcOH 5/1 and let under stirring at room temperature. After 30 minutes sodium triacetoxyborohydride 4.7 g (22.5 mmol) was added portion-wise. The reaction was let stir a few hours and evaporated down. The crude was purified on silica gel with AcOEt/EtOH/(NH$_3$ 7 N in MeOH) 8/2/0.2 to give 2.3 g of pink solid as a free base.

$^1$H NMR (DMSO-d$_6$) δ 2.20 (s, 3H) 2.38-2.45 (m, 4H) 2.89-2.98 (m, 4H) 6.58-6.67 (m, 2H) 6.72-6.80 (m, 2H) 8.76 (s, 1H)

MS calc: 193.1336 MS found: 193.1328.

Example 25

8-(methylsulfonyl)-4,5-dihydroisoxazolo[4,5-h]quinazoline-3-carboxamide

Conv.h

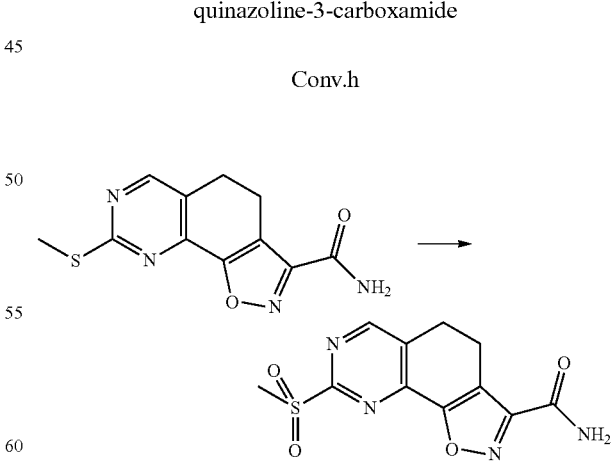

8-(methylsulfanyl)-4,5-dihydroisoxazolo[4,5-h]quinazoline-3-carboxamide 0.1 g (0.38 mmol) was suspended in 10 mL of DCM and reacted with mCPBA 0.26 g (1.52 mmol) for 3 hours. $H_2O$ and $NaHCO_3$ were added and the mixture extracted with AcOEt. The organic layer was dried over

Example 26

8-[4-(4-methylpiperazin-1-yl)phenoxy]-4,5-dihydroisoxazolo[4,5-h]quinazoline-3-carboxamide trifluoroacetate and 8-[4-(4-methylpiperazin-1-yl)phenoxy]isoxazolo[4,5-h]quinazoline-3-carboxamide trifluoroacetate Conv.k

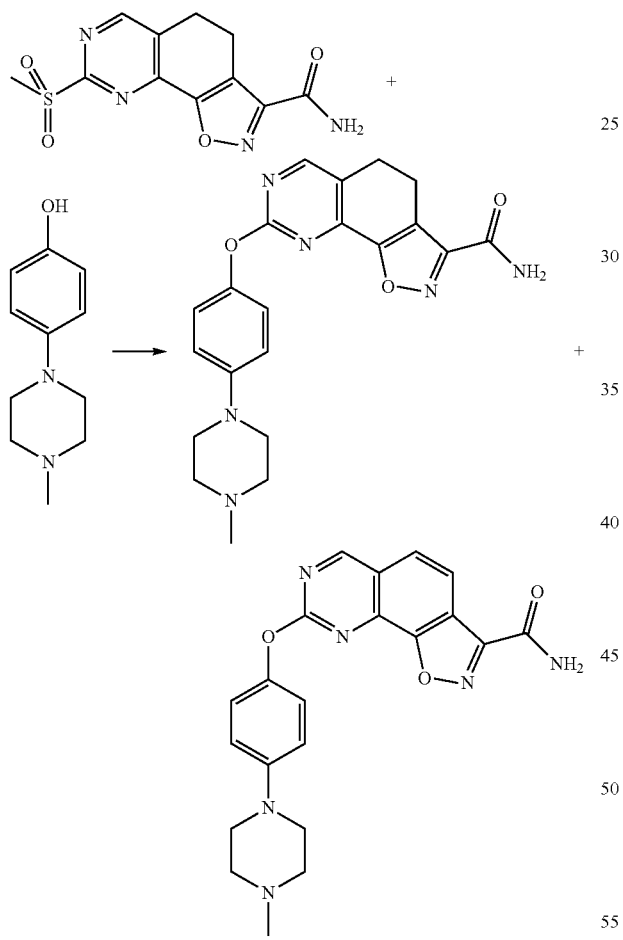

8-(methylsulfonyl)-4,5-dihydroisoxazolo[4,5-h]quinazoline-3-carboxamide 0.07 g (0.24 mmol) and 4-(4-methylpiperazin-1-yl)phenol 0.05 g (0.26 mmol) were reacted in 5 mL of anhydrous DMF in the presence of $K_2CO_3$ 0.1 g (0.78 mmol) at 70° C. for 2 hours. After cooling, the reaction was dried under vacuum with a spoon of silica and quickly eluted by flash chromatography (DCM/MeOH/$NH_3$ 7N in MeOH 9/1/0.4%) to give the mixture 1:1 of the two compounds. Each product was then isolated as trifluoroacetate salt by preparative HPLC.

8-[4-(4-methylpiperazin-1-yl)phenoxy]-4,5-dihydroisoxazolo[4,5-h]quinazoline-3-carboxamide trifluoroacetate $^1$H NMR (DMSO-$d_6$) δ 2.82 (br. s., 3H), 2.96-3.05 (m, 4H), 7.02-7.09 (m, 2H), 7.10-7.16 (m, 2H), 7.93 (s, 1H), 8.22 (s, 1H), 8.59 (s, 1H), 9.64 (br. s., 1H)

MS calc: 407.1826. MS found: 407.1823.

and

8-[4-(4-methylpiperazin-1-yl)phenoxy]isoxazolo[4,5-h]quinazoline-3-carboxamide trifluoroacetate $^1$H NMR (DMSO-$d_6$) δ 2.81 (br. s., 3H), 7.09-7.14 (m, 2H), 7.23-7.28 (m, 2H), 8.07-8.11 (m, 1H), 8.12-8.15 (m, 1H), 8.17 (s, 1H), 8.52 (s, 1H), 9.75 (s, 1H).

MS calc: 405.167. MS found: 405.1663.

Example 27

Ethyl 8-(methylsulfanyl)-4,5-dihydroisoxazolo[4,3-h]quinazoline-3-carboxylate st.A3

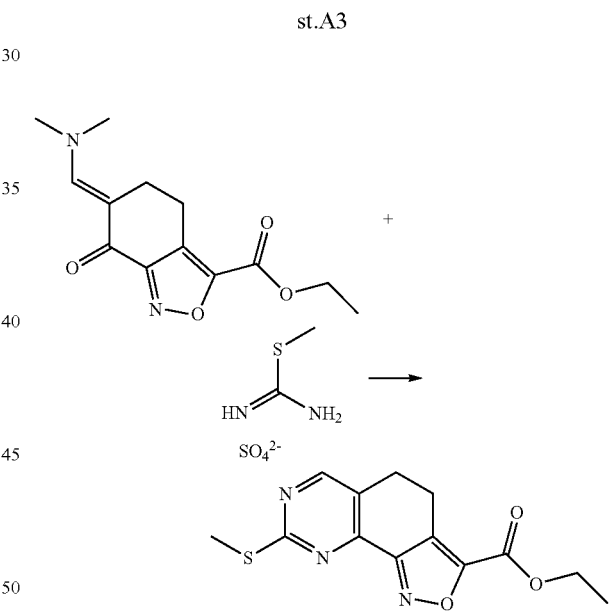

A solution of ethyl-6-[(dimethylamino)methylidene]-7-oxo-4,5,6,7-tetrahydro-2,1-benzisoxazole-3-carboxylate 0.5 g (1.90 mmol), S-methyl isothiourea sulphate 0.53 g (1.90 mmol) and potassium acetate 0.37 g (3.8 mmol) in 10 mL of DMF was stirred at 85° C. for 2 hours. After cooling, the reaction was worked up with $H_2O$ and AcOEt. The pooled organic extracts were washed with brine, dried over $Na_2SO_4$ and evaporated down. The crude material was purified by silica/flash column chromatography (Hexane/AcOEt 1/1) to give the clean product in 85% yield.

$^1$H NMR (DMSO-$d_6$) δ 1.36 (t, J=7.08 Hz, 3H), 2.57 (s, 3H), 2.95-3.02 (m, 2H), 3.03-3.12 (m, 2H), 4.41 (q, J=7.08 Hz, 2H), 8.77 (s, 1H)

MS calc: 292.0751. MS found: 292.07461.

Example 28

8-(methylsulfanyl)-4,5-dihydroisoxazolo[4,3-h]quinazoline-3-carboxamide

Conv.c

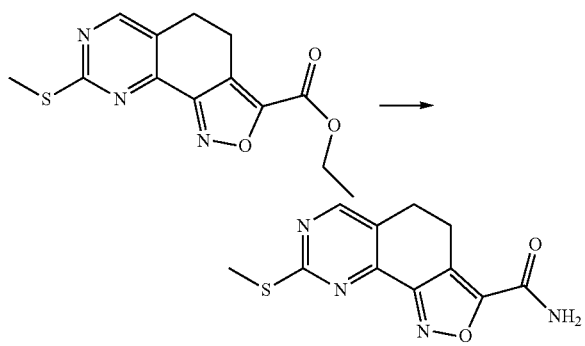

In a sealed vial, 0.4 g of ethyl 8-(methylsulfanyl)-4,5-dihydroisoxazolo[4,3-h]quinazoline-3-carboxylate were suspended in 5 mL of MeOH and 3 mL of $NH_3$ 7M in MeOH were added. The mixture was irradiated in the microwave at 100° C. for 30 minutes. After evaporation, the title compound was provided quantitatively.

$^1$H NMR (DMSO-$d_6$) δ 2.57 (s, 3H), 2.92-2.99 (m, 2H), 3.00-3.08 (m, 2H), 8.02 (br. s., 1H), 8.35 (s, 1H), 8.75 (s, 1H)
MS calc: 263.0597. MS found: 263.0587.

Example 29

8-(methylsulfonyl)-4,5-dihydroisoxazole[4,3-h]quinazoline-3-carboxamide

Conv.h

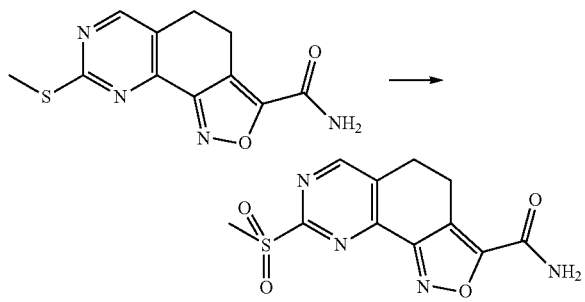

8-(methylsulfanyl)-4,5-dihydroisoxazolo[4,3-h]quinazoline-3-carboxamide 0.1 g (0.38 mmol) was suspended in 10 mL of DCM and reacted with mCPBA 0.26 g (1.52 mmol) for 3 hours. $H_2O$ and $NaHCO_3$ were added and the mixture extracted with AcOEt. The organic layer was dried over $Na_2SO_4$, the solvent was evaporated to dryness; the product was submitted to the next step without characterization.

Example 30

8-[4-(4-methylpiperazin-1-yl)phenoxy]-4,5-dihydroisoxazolo[4,3-h]quinazoline-3-carboxamide Conv.k 8-(methylsulfonyl)-4,5-dihydroisoxazole[4,3-h]quinazoline-3-carboxamide 0.11 g (0.38 mmol) and 4-(4-methylpiperazin-1-yl)phenol 0.80 g (0.41 mmol) were reacted in 5 mL of anhydrous DMF in the presence of $K_2CO_3$ 0.16 g (1.13 mmol) at 70° C. for 2 hours. After cooling, the reaction was dried under vacuum and purified by flash chromatography (DCM/MeOH/$NH_3$ 7M in MeOH 9/1/0.4) to give the title compound in 70% yield $^1$H NMR (DMSO-$d_6$) δ 2.25 (s, 3H), 2.47-2.52 (m, 4H), 2.93-2.99 (m, 2H), 3.01-3.07 (m, 2H), 3.14 (br. s., 4H), 6.96-7.01 (m, 2H), 7.03-7.10 (m, 2H), 8.02 (s, 1H), 8.34 (s, 1H), 8.69 (s, 1H).
MS calc: 407.1826. MS found: 407.1826.

---

The invention claimed is:

1. A compound of formula (I):

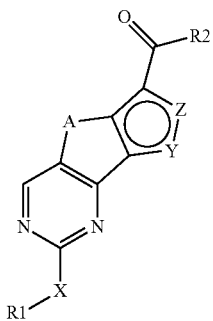

wherein:
Y is O and Z is N, or Y is N and Z is O;
X is NH;
R1 is a phenyl that is optionally substituted with a first 1 to 6 groups, independently selected from: $C_1$-$C_6$ alkyl, polyfluorinated alkyl, polyfluorinated alkoxy, hydroxyalkyl, heterocyclyl, $C_3$-$C_7$ cycloalkyl, hydroxy, alkoxy, amino, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, heterocyclylaminocarbonyl, alkylcarbonyl, cycloalkylcarbonyl, and heterocyclylcarbonyl, wherein heterocyclyl is a 3 to 7 membered saturated carbocyclic ring wherein 1 to 3 carbon atoms are replaced with nitrogen, wherein the first 1 to 6 groups is further optionally substituted with a second 1 to 6 groups independently selected from $C_1$-$C_6$ alkyl, polyfluorinated alkyl, polyfluorinated alkoxy, hydroxyalkyl, heterocyclyl, $C_3$-$C_7$ cycloalkyl, hydroxy, alkoxy, amino, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, heterocyclylaminocarbonyl, alkylcarbonyl, cycloalkylcarbonyl, and heterocyclylcarbonyl, wherein heterocyclyl is a 3 to 7 membered saturated carbocyclic ring wherein 1 to 3 carbon atoms are replaced with nitrogen;
R2 is —NR'R", wherein R' is hydrogen and R" is hydrogen or a group, selected from straight or branched $C_1$-$C_6$ alkyl and phenyl, that is optionally substituted with 1 to 6 groups, independently selected from: $C_1$-$C_6$ alkyl, phenyl, amino, alkylamino and dialkylamino;
A is a divalent group selected from —$(CH_2)_2$—, —$CH_2$—$C(CH_3)_2$—, and —$C(CH_3)_2$—$CH_2$—;
and the pharmaceutically acceptable salts thereof.

2. A compound of formula (I) or a pharmaceutically acceptable salt thereof as defined in claim 1 which is selected from the group consisting of:
N-(2,6-diethylphenyl)-8-{[2-methoxy-4-(4-methylpiperazin-1-yl)phenyl]amino}-4,5-dihydroisoxazolo[4,3-h]quinazoline-3-carboxamide,
8-{[4-(4-methylpiperazin-1-yl)phenyl]amino}-4,5-dihydroisoxazolo[4,3-h]quinazoline-3-carboxamide,
N-(2,6-diethylphenyl)-8-{[4-(4-methylpiperazin-1-yl)phenyl]amino}-4,5-dihydroisoxazolo[4,3-h]quinazoline-3-carboxamide,
N-(2,6-diethylphenyl)-8-({4-[4-(2-hydroxyethyl)piperazin-1-yl]-2-methoxyphenyl}amino)-4,5-dihydroisoxazolo[4,3-h]quinazoline-3-carboxamide,
N-(2,6-diethylphenyl)-8-{[2-methoxy-4-(4-pyrrolidin-1-ylpiperidin-1-yl)phenyl]amino}-4,5-dihydroisoxazolo[4,3-h]quinazoline-3-carboxamide,
8-{[2-methoxy-4-(4-methylpiperazin-1-yl)phenyl]amino}-4,5-dihydroisoxazolo[4,3-h]quinazoline-3-carboxamide,
5,5-dimethyl-8-{[4-(4-methylpiperazin-1-yl)-2-(trifluoromethoxy)phenyl]amino}-4,5-dihydroisoxazolo[4,3-h]quinazoline-3-carboxamide,
N-(2,6-diethylphenyl)-8-[(4-{[2-(dimethylamino)ethyl]carbamoyl}-2-methoxyphenyl)amino]-4,5-dihydroisoxazolo[4,3-h]quinazoline-3-carboxamide,
N-(2,6-diethylphenyl)-8-[(4-{[4-(dimethylamino)piperidin-1-yl]carbonyl}-2-methoxyphenyl)amino]-4,5-dihydroisoxazolo[4,3-h]quinazoline-3-carboxamide,
N-(2,6-diethylphenyl)-8-[(2-methoxy-4-{[(2S)-2-(pyrrolidin-1-ylmethyl)pyrrolidin-1-yl]carbonyl}phenyl)amino]-4,5-dihydroisoxazolo[4,3-h]quinazoline-3-carboxamide,
N-(2,6-diethylphenyl)-8-[(2-methoxy-4-{[(2R)-2-(pyrrolidin-1-ylmethyl)pyrrolidin-1-yl]carbonyl}phenyl)amino]-4,5-dihydroisoxazolo[4,3-h]quinazoline-3-carboxamide,
N-(2,6-diethylphenyl)-8-{[4-(4-methylpiperazin-1-yl)-2-(trifluoromethoxy)phenyl]amino}-4,5-dihydroisoxazolo[4,3-h]quinazoline-3-carboxamide,
8-{[4-(4-methylpiperazin-1-yl)-2-(trifluoromethoxy)phenyl]amino}-4,5-dihydroisoxazolo[4,3-h]quinazoline-3-carboxamide,
N-(2,6-diethylphenyl)-8-({4-[4-(dimethylamino)piperidin-1-yl]-2-methoxyphenyl}amino)-4,5-dihydroisoxazolo[4,3-h]quinazoline-3-carboxamide,
N-(2,6-diethylphenyl)-8-[(4-{[2-(dimethylamino)ethyl](methyl)amino}-2-methoxyphenyl)amino]-4,5-dihydroisoxazolo[4,3-h]quinazoline-3-carboxamide, 5,5-dimethyl-8-{[4-(4-methylpiperazin-1-yl)phenyl] amino}-4,5-dihydroisoxazolo[4,3-h]quinazoline-3-carboxamide, 8-({2-methoxy-4-[(1-methylpiperidin-4-yl)carbamoyl] phenyl}amino)-4,4-dimethyl-4,5-dihydroisoxazolo[4,3-h]quinazoline-3-carboxamide, 8-({2-methoxy-4-[(1-methylpiperidin-4-yl)carbamoyl] phenyl}amino)-5,5-dimethyl-4,5-dihydroisoxazolo[4,3-h]quinazoline-3-carboxamide, N-[(1S)-2-amino-1-phenylethyl]-8-({2-methoxy-4-[(1-methylpiperidin-4-yl)carbamoyl]phenyl}amino)-5,5-dimethyl-4,5-dihydroisoxazolo[4,3-h]quinazoline-3-carboxamide, N-[(1S)-2-amino-1-phenylethyl]-8-({2-methoxy-4-[(1-methylpiperidin-4-yl)carbamoyl]phenyl}amino)-4,4-dimethyl-4,5-dihydroisoxazolo[4,3-h]quinazoline-3-carboxamide, N-(2,6-diethylphenyl)-8-{[2-methoxy-4-(4-methylpiperazin-1-yl)phenyl]amino}-4,5-dihydroisoxazolo[4,5-h]quinazoline-3-carboxamide, 8-{[4-(4-methylpiperazin-1-yl)phenyl]amino}-4,5-dihydroisoxazolo[4,5-h]quinazoline-3-carboxamide, N-(2,6-diethylphenyl)-8-{[2-methoxy-4-(4-pyrrolidin-1-ylpiperidin-1-yl)phenyl]amino}-4,5-dihydroisoxazolo[4,5-h]quinazoline-3-carboxamide, N-(2,6-diethylphenyl)-8-({4-[4-(2-hydroxyethyl)piperazin-1-yl]-2-methoxyphenyl}amino)-4,5-dihydroisoxazolo[4,5-h]quinazoline-3-carboxamide, N-(2,6-diethylphenyl)-8-({4-[4-(dimethylamino)piperidin-1-yl]-2-methoxyphenyl}amino)-4,5-dihydroisoxazolo[4,5-h]quinazoline-3-carboxamide, N-(2,6-diethylphenyl)-8-[(4-{[4-(dimethylamino)piperidin-1-yl]carbonyl}-2-methoxyphenyl)amino]-4,5-dihydroisoxazolo[4,5-h]quinazoline-3-carboxamide, 5,5-dimethyl-8-{[4-(4-methylpiperazin-1-yl)phenyl] amino}-4,5-dihydroisoxazolo[4,5-h]quinazoline-3-carboxamide, 8-{[4-(4-methylpiperazin-1-yl)-2-(trifluoromethoxy)phenyl]amino}-4,5-dihydroisoxazolo[4,5-h]quinazoline-3-carboxamide, N-(2,6-diethylphenyl)-8-{[4-(4-methylpiperazin-1-yl)-2-(trifluoromethoxy)phenyl]amino}-4,5-dihydroisoxazolo[4,5-h]quinazoline-3-carboxamide, 8-({2-methoxy-4-[(1-methylpiperidin-4-yl)carbamoyl] phenyl}amino)-5,5-dimethyl-4,5-dihydroisoxazolo[4,5-h]quinazoline-3-carboxamide, N-[(2R)-2-amino-2-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide, N-[(1R)-2-amino-1-phenylethyl]-8-({2-methoxy-4-[(1-methylpiperidin-4-yl)carbamoyl]phenyl}amino)-5,5-dimethyl-4,5-dihydroisoxazolo[4,5-h]quinazoline-3-carboxamide and 5,5-dimethyl-8-{[4-(4-methylpiperazin-1-yl)-2-(trifluoromethoxy)phenyl]amino}-4,5-dihydroisoxazolo[4,5-h]quinazoline-3-carboxamide.

3. A process for preparing a compound of formula (I) or the pharmaceutically acceptable salts thereof, as defined in claim 1, which process comprises:

st.A1) reacting a compound of the formula (II):

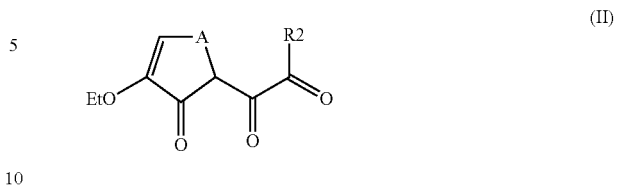

(II)

wherein R2 is O—($C_1$-$C_4$ alkyl), A is a divalent group selected from —($CH_2$)$_2$—, —$CH_2$—C($CH_3$)$_2$— and —C($CH_3$)$_2$—$CH_2$—, with hydroxylamine HO—$NH_2$HCl, optionally in the presence of a $C_1$-$C_4$ alkyl alcohol, and separating the resultant compounds (IIIa) and (IIIb):

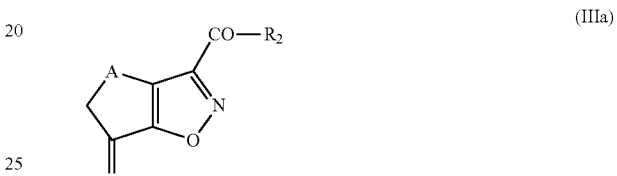

(IIIa)

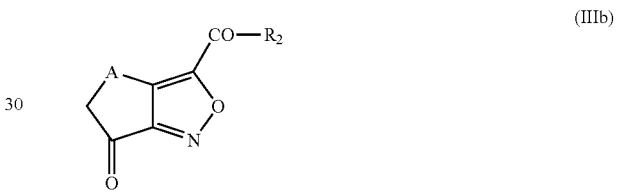

(IIIb)

wherein R2 and A are as defined above;

or st.A1/a) reacting a compound of the formula (II-) as defined above, with hydroxylamine HO—$NH_2$.$H_2O$ in acetic acid and a $C_1$-$C_4$ alkyl alcohol, then separating the single compounds, (IIa) and (IIb);

st.A1/b) dehydrating in acidic conditions the resultant compound of formula (IIa) and (IIb):

(IIa)

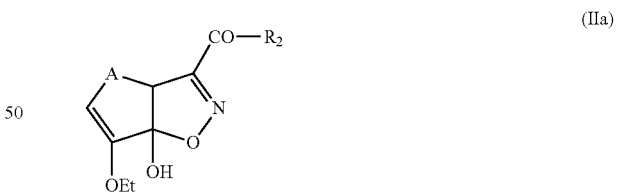

(IIb)

wherein R2 and A are as defined above, to give the compound of formula (IIIa) and (IIIb) as defined above;

st.A2) reacting the compound of the formula (IIIa) or (IIIb), obtained in st.A1 or in st.A1/b, with an N—N-dimethylformamide derivative;

st.A3) reacting the resultant compound of the formula (IV):

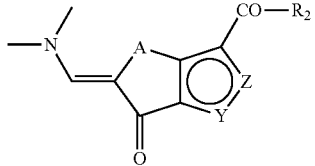

(IV)

wherein Y and Z are as defined in claim 1, and R2 and A are as defined above, with a compound of the formula (V):

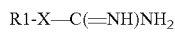

R1-X—C(=NH)NH$_2$ (V)

wherein R1 is as defined in claim 1, and X is as defined in claim 1, through pyrimidine ring formation carried out in N,N-dimethylformamide or ethanol at a temperature to give a compound of the formula:

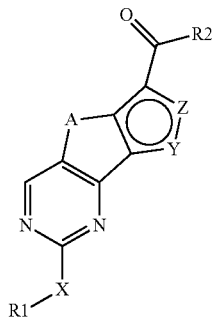

(I)' wherein R1, Y and Z are as defined above, R2 is O—(C$_1$-C$_4$ alkyl), A is a divalent group selected from —(CH$_2$)$_2$—, —CH$_2$—C(CH$_3$)$_2$— and —C(CH$_3$)$_2$—CH$_2$—, and X is as defined above, and converting a compound of the formula (I)' as defined above into a compound of the formula (I) as defined in claim 1, and, optionally, converting a compound of the formula (I) as defined in claim 1 into a pharmaceutically acceptable salt thereof or converting a salt into the free compound of formula (I) as defined in claim 1.

4. A process for preparing a compound of formula (I), as defined in claim 1 which is carried out with the following methods:
either
Conv.a) converting a compound of formula (I)', wherein R1, X, A, Y and Z are as defined in claim 1, into the corresponding carboxylic acid or salt through ester hydrolysis under acid or basic conditions:

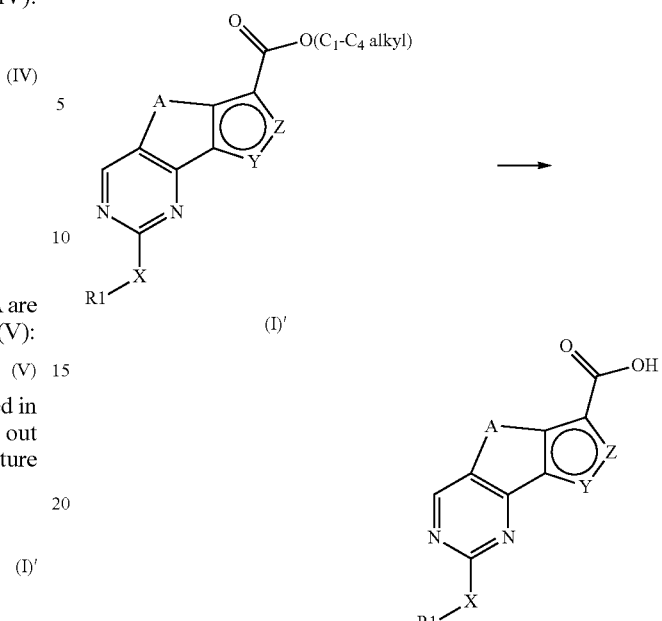

then
Conv.b) converting the obtained product into the corresponding compound of formula (I) as defined in claim 1, through reaction with an amine of formula R'R"—NH (VI) wherein R' and R" are as defined in claim 1, under basic conditions and in the presence of a suitable condensing agent;
or
Conv.c) converting a compound of formula (I)', as defined in conv.a) into the corresponding compound of formula (I) as defined in claim 1, by treatment with an amine of formula R'R"—NH (VI), as defined in conv.b).

5. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

6. A pharmaceutical composition according to claim 5 further comprising one or more chemotherapeutic agents.

7. A kit comprising a compound of formula (I) or a pharmaceutically acceptable salt thereof, as defined in claim 1, or pharmaceutical compositions thereof and one or more chemotherapeutic agents, as a combined preparation for simultaneous, separate or sequential use in anticancer therapy.

* * * * *